US009462802B2

(12) United States Patent
Fishman et al.

(10) Patent No.: US 9,462,802 B2
(45) Date of Patent: Oct. 11, 2016

(54) SYSTEMS AND METHODS FOR EX VIVO LUNG CARE

(75) Inventors: Robert Fishman, Boston, MA (US); Robert Havener, Lynnfield, MA (US); Ihab Abdel Fattah, Andover, MA (US); Anas Abdelazim, North Andover, MA (US); Scott Newell, Ipswich, MA (US); Tom Bishop, Wenham, MA (US); Tamer Khayal, North Andover, MA (US); Stanley Kyi, Andover, MA (US); Ron Taylor, Chester, NH (US); Doug Harriott, Melrose, MA (US); Matthew De Remer, Allston, MA (US); Paul Murray, Groton, MA (US); John Sullivan, Groton, MA (US); Mark Anderson, Danvers, MA (US); Richard Bringham, North Andover, MA (US); Michael Van Driel, Mirandola (IT); Waleed Hassanein, North Andover, MA (US)

(73) Assignee: TRANSMEDICS, INC., Andover, MA (US)

( * ) Notice: Subject to any disclaimer, the term of this patent is extended or adjusted under 35 U.S.C. 154(b) by 1349 days.

(21) Appl. No.: 12/099,725

(22) Filed: Apr. 8, 2008

(65) Prior Publication Data

US 2009/0197324 A1 Aug. 6, 2009

Related U.S. Application Data

(60) Provisional application No. 61/024,976, filed on Jan. 31, 2008.

(51) Int. Cl.
*A01N 1/02* (2006.01)

(52) U.S. Cl.
CPC .............. *A01N 1/02* (2013.01); *A01N 1/0247* (2013.01)

(58) Field of Classification Search
CPC ............................. A01N 1/0247; A01N 1/02
USPC ........................................................ 435/284.1
See application file for complete search history.

(56) References Cited

U.S. PATENT DOCUMENTS

| 3,253,595 A | 5/1966 | Murphy et al. |
| 3,388,803 A | 6/1968 | Scott |

(Continued)

FOREIGN PATENT DOCUMENTS

| CN | 1232723 A | 10/1999 |
| DE | 4201259 A1 | 7/1993 |

(Continued)

OTHER PUBLICATIONS

PCT/US09/032619 International search report mailed Jun. 4, 2009 (3 pages).

(Continued)

*Primary Examiner* — Jonathan Hurst
(74) *Attorney, Agent, or Firm* — Wilmer Cutler Pickering Hale and Dorr LLP

(57) ABSTRACT

Methods and systems of maintaining, evaluating, and providing therapy to a lung ex vivo. The methods and systems involve positioning the lung in an ex vivo perfusion circuit; circulating a perfusion fluid through the lung, the fluid entering the lung through a pulmonary artery interface and leaving the lung through a left atrial interface; and ventilating the lung by flowing a ventilation gas through a tracheal interface. Maintaining the lung for extended periods involves causing the lung to rebreath a captive volume of air, and reaching an equilibrium state between the perfusion fluid and the ventilation gas. Evaluating the gas exchange capability of the lung involves deoxygenating the perfusion fluid and measuring a time taken to reoxygenate the perfusion fluid by ventilating the lung with an oxygenation gas.

23 Claims, 36 Drawing Sheets

(56) References Cited

U.S. PATENT DOCUMENTS

| | | |
|---|---|---|
| 3,406,531 A | 10/1968 | Swenson et al. |
| 3,468,136 A | 9/1969 | Swenson et al. |
| 3,537,956 A | 11/1970 | Falcone |
| 3,545,221 A | 12/1970 | Swenson et al. |
| 3,545,605 A | 12/1970 | Robins |
| 3,587,567 A | 6/1971 | Schiff |
| 3,607,646 A | 9/1971 | de Roissart |
| 3,632,473 A | 1/1972 | Belzer et al. |
| 3,639,084 A | 2/1972 | Goldhaber |
| 3,654,085 A | 4/1972 | Norr et al. |
| 3,738,914 A | 6/1973 | Thorne et al. |
| 3,772,153 A | 11/1973 | De Roissart |
| 3,777,507 A | 12/1973 | Burton et al. |
| 3,843,455 A | 10/1974 | Bier |
| 3,851,646 A * | 12/1974 | Sarns .................... 604/93.01 |
| 3,881,990 A | 5/1975 | Burton et al. |
| 3,995,444 A | 12/1976 | Clark et al. |
| 4,186,565 A | 2/1980 | Toledo-Pereyra |
| 4,231,354 A | 11/1980 | Kurtz et al. |
| 4,415,556 A | 11/1983 | Bretschneider et al. |
| 4,598,697 A | 7/1986 | Numazawa et al. |
| 4,605,644 A | 8/1986 | Foker |
| 4,666,425 A | 5/1987 | Fleming |
| 4,719,201 A | 1/1988 | Foker |
| 4,723,939 A | 2/1988 | Anaise |
| 4,745,759 A | 5/1988 | Bauer et al. |
| 4,759,371 A | 7/1988 | Franetzki |
| 4,847,470 A | 7/1989 | Bakke |
| 4,920,044 A | 4/1990 | Bretan, Jr. |
| 5,051,352 A | 9/1991 | Martindale et al. |
| 5,066,578 A | 11/1991 | Wikman-Coffelt |
| 5,141,847 A | 8/1992 | Sugimachi et al. |
| 5,145,771 A | 9/1992 | Lemasters et al. |
| 5,157,930 A | 10/1992 | McGhee et al. |
| 5,200,398 A | 4/1993 | Strasberg et al. |
| 5,217,860 A | 6/1993 | Fahy et al. |
| 5,285,657 A | 2/1994 | Bacchi et al. |
| 5,306,711 A | 4/1994 | Andrews |
| 5,326,706 A | 7/1994 | Yland et al. |
| 5,338,662 A | 8/1994 | Sadri |
| 5,356,593 A | 10/1994 | Heiberger et al. |
| 5,356,771 A | 10/1994 | O'Dell |
| 5,362,622 A | 11/1994 | O'Dell et al. |
| 5,370,989 A | 12/1994 | Stern et al. |
| 5,381,510 A | 1/1995 | Ford et al. |
| 5,385,821 A | 1/1995 | O'Dell et al. |
| 5,395,314 A | 3/1995 | Klatz et al. |
| 5,405,742 A | 4/1995 | Taylor |
| 5,407,669 A | 4/1995 | Lindstrom et al. |
| 5,407,793 A | 4/1995 | Del Nido et al. |
| 5,472,876 A | 12/1995 | Fahy |
| 5,473,791 A | 12/1995 | Holcomb et al. |
| 5,494,822 A | 2/1996 | Sadri |
| 5,498,427 A | 3/1996 | Menasche et al. |
| 5,505,709 A | 4/1996 | Funderburk et al. |
| 5,514,536 A | 5/1996 | Taylor |
| 5,552,267 A | 9/1996 | Stern et al. |
| 5,554,123 A | 9/1996 | Herskowitz |
| 5,554,497 A | 9/1996 | Raymond |
| 5,571,801 A | 11/1996 | Segall et al. |
| 5,584,804 A | 12/1996 | Klatz et al. |
| 5,586,438 A | 12/1996 | Fahy |
| 5,588,816 A | 12/1996 | Abbott et al. |
| 5,599,173 A | 2/1997 | Chen et al. |
| 5,599,659 A | 2/1997 | Brasile et al. |
| 5,613,944 A | 3/1997 | Segall et al. |
| 5,643,712 A | 7/1997 | Brasile |
| 5,656,420 A | 8/1997 | Chien |
| 5,679,565 A | 10/1997 | Mullen et al. |
| 5,693,462 A | 12/1997 | Raymond |
| 5,698,536 A | 12/1997 | Segall et al. |
| 5,699,793 A | 12/1997 | Brasile |
| 5,702,881 A | 12/1997 | Brasile et al. |
| 5,716,378 A | 2/1998 | Minten et al. |
| 5,723,281 A | 3/1998 | Segall et al. |
| 5,733,894 A | 3/1998 | Segall et al. |
| 5,747,071 A | 5/1998 | Segall et al. |
| 5,752,929 A | 5/1998 | Klatz et al. |
| 5,770,149 A | 6/1998 | Raible |
| 5,776,063 A | 7/1998 | Dittrich et al. |
| 5,786,136 A | 7/1998 | Mayer et al. |
| 5,787,544 A | 8/1998 | Meade |
| 5,807,737 A | 9/1998 | Schill et al. |
| 5,823,799 A | 10/1998 | Tor et al. |
| 5,843,024 A | 12/1998 | Brasile |
| 5,856,081 A | 1/1999 | Fahy |
| 5,882,328 A | 3/1999 | Levy et al. |
| 5,965,433 A | 10/1999 | Gardetto et al. |
| 5,998,240 A | 12/1999 | Hamilton et al. |
| 6,024,698 A | 2/2000 | Brasile |
| 6,034,109 A | 3/2000 | Ramasamy et al. |
| 6,042,550 A | 3/2000 | Haryadi et al. |
| 6,046,046 A | 4/2000 | Hassanein |
| 6,050,987 A * | 4/2000 | Rosenbaum .................... 604/533 |
| 6,100,082 A | 8/2000 | Hassanein |
| 6,110,139 A | 8/2000 | Loubser |
| 6,110,504 A | 8/2000 | Segall et al. |
| 6,144,444 A | 11/2000 | Haworth et al. |
| 6,168,877 B1 | 1/2001 | Pedicini et al. |
| 6,365,338 B1 | 4/2002 | Bull et al. |
| 6,375,611 B1 | 4/2002 | Voss et al. |
| 6,375,613 B1 | 4/2002 | Brasile |
| 6,389,308 B1 | 5/2002 | Shusterman |
| 6,475,716 B1 | 11/2002 | Seki et al. |
| 6,490,880 B1 | 12/2002 | Walsh |
| 6,492,103 B1 | 12/2002 | Taylor |
| 6,492,745 B1 | 12/2002 | Colley, III et al. |
| 6,524,785 B1 | 2/2003 | Cozzone et al. |
| 6,569,615 B1 | 5/2003 | Thatte et al. |
| 6,582,953 B2 * | 6/2003 | Brasile ........................ 435/284.1 |
| 6,600,941 B1 | 7/2003 | Khuri |
| 6,609,987 B1 | 8/2003 | Beardmore |
| 6,631,830 B2 | 10/2003 | Ma et al. |
| 6,642,045 B1 | 11/2003 | Brasile |
| 6,673,594 B1 | 1/2004 | Owen et al. |
| 6,696,238 B2 | 2/2004 | Murphy et al. |
| 6,783,328 B2 | 8/2004 | Lucke et al. |
| 6,792,309 B1 | 9/2004 | Noren |
| 6,794,124 B2 | 9/2004 | Steen et al. |
| 6,811,965 B2 | 11/2004 | Vodovotz et al. |
| 6,878,339 B2 | 4/2005 | Akiyama et al. |
| 6,925,324 B2 | 8/2005 | Shusterman |
| 6,953,655 B1 | 10/2005 | Hassanein et al. |
| 6,974,436 B1 * | 12/2005 | Aboul-Hosn et al. ............ 604/9 |
| 7,001,354 B2 | 2/2006 | Suzuki et al. |
| 7,008,380 B1 | 3/2006 | Rees et al. |
| 7,238,165 B2 | 7/2007 | Vincent et al. |
| 7,316,666 B1 | 1/2008 | Entenman et al. |
| 7,452,711 B2 | 11/2008 | Daykin |
| 7,572,622 B2 | 8/2009 | Hassanein et al. |
| 7,651,835 B2 | 1/2010 | Hassanein et al. |
| 8,304,181 B2 | 11/2012 | Hassanein et al. |
| 8,409,846 B2 | 4/2013 | Hassanein et al. |
| 8,420,380 B2 | 4/2013 | Fishman et al. |
| 8,465,970 B2 | 6/2013 | Hassanein et al. |
| 8,535,934 B2 | 9/2013 | Hassanein et al. |
| 8,585,380 B2 | 11/2013 | Hassanein et al. |
| 9,215,867 B2 | 12/2015 | Hassanein et al. |
| 2001/0003652 A1 | 6/2001 | Freeman |
| 2002/0012988 A1 | 1/2002 | Brasile |
| 2002/0102720 A1 | 8/2002 | Steen |
| 2002/0132220 A1 | 9/2002 | Berens et al. |
| 2002/0151950 A1 | 10/2002 | Okuzumi |
| 2002/0164795 A1 | 11/2002 | Gen |
| 2002/0177117 A1 | 11/2002 | Wolf |
| 2003/0011604 A1 | 1/2003 | Capers |
| 2003/0040665 A1 | 2/2003 | Khuri et al. |
| 2003/0050689 A1 | 3/2003 | Matson |
| 2003/0053998 A1 | 3/2003 | Daemen et al. |
| 2003/0073227 A1 | 4/2003 | Hull et al. |
| 2003/0074760 A1 | 4/2003 | Keller |
| 2003/0086830 A1 | 5/2003 | Haywood et al. |
| 2003/0111604 A1 | 6/2003 | Quek |
| 2003/0135152 A1 | 7/2003 | Kollar et al. |

(56) References Cited

U.S. PATENT DOCUMENTS

| | | |
|---|---|---|
| 2003/0147466 A1 | 8/2003 | Liang |
| 2004/0015042 A1 | 1/2004 | Vincent et al. |
| 2004/0017658 A1 | 1/2004 | Lo et al. |
| 2004/0018966 A1 | 1/2004 | Segall et al. |
| 2004/0029096 A1 | 2/2004 | Steen |
| 2004/0038192 A1 | 2/2004 | Brasile |
| 2004/0058432 A1 | 3/2004 | Owen et al. |
| 2004/0082057 A1 | 4/2004 | Alford et al. |
| 2004/0086578 A1 | 5/2004 | Segall et al. |
| 2004/0102415 A1 | 5/2004 | Thatte et al. |
| 2004/0102678 A1 | 5/2004 | Haindl |
| 2004/0106958 A1 | 6/2004 | Mathis et al. |
| 2004/0110800 A1 | 6/2004 | Bril et al. |
| 2004/0115689 A1* | 6/2004 | Augello et al. |
| 2004/0138542 A1 | 7/2004 | Khuri et al. |
| 2004/0168341 A1 | 9/2004 | Petersen et al. |
| 2004/0170950 A1 | 9/2004 | Prien |
| 2004/0171138 A1 | 9/2004 | Hassanein et al. |
| 2004/0202993 A1 | 10/2004 | Poo et al. |
| 2004/0224298 A1 | 11/2004 | Brassil et al. |
| 2004/0235142 A1 | 11/2004 | Schein et al. |
| 2004/0236170 A1 | 11/2004 | Kim |
| 2004/0248281 A1 | 12/2004 | Wright et al. |
| 2005/0010118 A1 | 1/2005 | Toyoda et al. |
| 2005/0019917 A1 | 1/2005 | Toledo-Pereyra et al. |
| 2005/0142532 A1 | 6/2005 | Poo et al. |
| 2005/0147958 A1 | 7/2005 | Hassanein et al. |
| 2005/0153271 A1 | 7/2005 | Wenrich |
| 2005/0170019 A1 | 8/2005 | Roth |
| 2005/0182349 A1 | 8/2005 | Linde et al. |
| 2005/0187469 A1 | 8/2005 | Phillips |
| 2006/0039870 A1 | 2/2006 | Turner |
| 2006/0074470 A1 | 4/2006 | Bartels et al. |
| 2006/0121438 A1 | 6/2006 | Toledo-Pereyra et al. |
| 2006/0124130 A1 | 6/2006 | Bonassa |
| 2006/0134073 A1 | 6/2006 | Naka et al. |
| 2006/0148062 A1 | 7/2006 | Hassanein et al. |
| 2006/0154357 A1 | 7/2006 | Hassanein et al. |
| 2006/0154359 A1 | 7/2006 | Hassanein et al. |
| 2006/0160204 A1 | 7/2006 | Hassanein et al. |
| 2006/0292544 A1 | 12/2006 | Hassanein et al. |
| 2007/0196461 A1 | 8/2007 | Weers |
| 2008/0017194 A1 | 1/2008 | Hassanein et al. |
| 2008/0234768 A1 | 9/2008 | Hassanein et al. |
| 2008/0286746 A1* | 11/2008 | Poo .......................... A01N 1/02 435/1.1 |
| 2009/0142830 A1 | 6/2009 | Yamashiro et al. |
| 2009/0143417 A1 | 6/2009 | Smith et al. |
| 2009/0197240 A1 | 8/2009 | Fishman et al. |
| 2009/0197292 A1 | 8/2009 | Fishman et al. |
| 2009/0197325 A1 | 8/2009 | Fishman et al. |
| 2009/0215022 A1 | 8/2009 | Page et al. |
| 2009/0312724 A1 | 12/2009 | Pipkin et al. |
| 2011/0136096 A1 | 6/2011 | Hassanein et al. |
| 2011/0190572 A1 | 8/2011 | Brophy et al. |
| 2011/0212431 A1 | 9/2011 | Bunegin et al. |
| 2013/0011823 A1 | 1/2013 | Hassanein et al. |
| 2013/0078710 A1 | 3/2013 | Hassanein et al. |
| 2013/0157248 A1 | 6/2013 | Fishman et al. |
| 2013/0295552 A1 | 11/2013 | Hassanein et al. |

FOREIGN PATENT DOCUMENTS

| | | |
|---|---|---|
| DE | 10121159 A1 | 11/2002 |
| DK | 4201259 | 7/1993 |
| EP | 0347923 | 12/1989 |
| EP | 0376763 | 7/1990 |
| JP | 02-306901 A | 12/1990 |
| JP | 04-099701 A | 3/1992 |
| JP | 2001061956 A | 3/2001 |
| JP | 2001516768 A | 10/2001 |
| JP | 2004513889 A | 5/2004 |
| JP | 2004525290 A | 8/2004 |
| JP | 2004529938 | 9/2004 |
| WO | WO-8805261 | 7/1988 |
| WO | WO-9531897 | 11/1995 |
| WO | WO-9618293 | 6/1996 |
| WO | WO-9629865 | 10/1996 |
| WO | WO-9746091 | 12/1997 |
| WO | WO-9915011 | 4/1999 |
| WO | WO-0060936 A1 | 10/2000 |
| WO | WO-2004026031 A2 | 4/2004 |
| WO | WO-2006042138 A2 | 4/2006 |
| WO | WO-2006076590 A2 | 7/2006 |
| WO | WO-2006124820 | 11/2006 |
| WO | WO-2007079185 | 7/2007 |
| WO | WO-2007124044 A2 | 11/2007 |
| WO | WO-2008106724 A1 | 9/2008 |

OTHER PUBLICATIONS

PCT/US98/19912 International search report mailed May 3, 1999 (4 pages).

Hardesty et al. Original Communications, "Autoperfusion of the heart and lungs for preservation during distant procurement," J. Thorac. Cardiovasc. Surg., 93: 11-18 (1987) (8 pages).

Hülsmann et al. "Loss of cardiac contractility and severe morphologic changes by acutely lowering the pH of the perfusion medium: protection by fatty acids," Bragen 20256, Biochimica et Biophysica Acta., 1033:214-218 (1990) (5 pages).

Probst et al. "Carbohydrate and fatty acid metabolism of cultured adult cardiac myocytes," Am. J. Physiol. 250 (Heart, Circ. Physiol. 19):H853-H860 (1986) (8 pages).

Grynberg et al. "Fatty acid oxidation in the heart," Journal of Cardiovascular Pharmacology, 28(Suppl. 1):S11-S17 (1996) (8 pages).

"http://dictionary.reference.com/browse/synchrony," Random House Unabridged Dictionary (2006) (1 page).

Brandes et al. "Influence of high molecular dextrans on lung function in an ex Vivo porcine lung model," J. of Surgical Research, 101:2, 225-231 (Dec. 2001) (7 pages).

Macchiarini et al. "Ex vivo lung model of pig-to-human hyperacute xenograft rejection," J. of Thoracic and Cardiovascular Surgery, 114:3, 315-325 (Sep. 1997) (9 pages).

PCT/US07/009652 International search report mailed Apr. 18, 2008 (7 pages).

Voiglio et al. "Rat multiple organ blocks: microsurgical technique of removal for ex vivo aerobic organ preservation using a fluorocarbon emulsion," Microsurgery 20: 109-115 (2000) (7 pages).

Wright et al. "A porcine ex vivo paracorporeal model of lung transplantation," Laboratory Animals, 34: 56-62 (2000) (7 pages).

Imber et al. "Advantages of Normothermic Perfusion Over Cold Storage in Liver Preservation," Transplantation, 73(5):701-09 (2002) (9 pages).

Barinov, et al. "Hormonal-metabolic disturbances during biological preservation of the heart," Fiziol. ZH., (Kiev), 29(3):293-299 (1983) (7 pages).

"2002 Design & Engineering Awards, Portable Organ Preservation System," Science (2002).

Ahmad, et al., "A Pathophysiologic Study of the Kidney Tubule to Optimize Organ Preservation Solutions," Kidney Int. 66(1):77-90 (2004).

Anathaswamy, "Machine Keeps Organs Alive for Longer," New Scientist.com (2002).

Aoki, M. et al. "Anti-CD18 Attenuates Deleterious Effects of Cardiopulmonary Bypass and Hypothermic Circulatory Arrest in Piglets," J. Card. Surg. 10:407-17 (1995).

Bando, et al., "Oxygenated Perfluorocarbon, Recombinant Human Superoxide Dismutase, and Catalase Ameliorate Free Radical Incuded Myocardial Injury During Heart Preservation and Transplantation," J. Thorac Cardiovasc Surb. 96:930-8 (Dec. 1988).

Belzer, "Formula for Belzer MPS Solution," University of Wisconsin-Madison Organ Preservation (internet reference) (2003).

Benichou, et al., "Canine and Human Liver Preservation for 6 to 18 Hours by Cold Infusion," Transplation, 24(6):407-411 (Dec. 1977).

Birkett et al., "The Fatty Acid Content and Drug Binding Characteristics of Commercial Albumin Preparations," Clin. Chem. Acta. 85:253-58 (1978).

(56) References Cited

OTHER PUBLICATIONS

Blanchard, et al., "Techniques for Perfusion and Storage of Heterotopic Heart Transplants in Mice," Microsurgery, 6:169-174 (1985).
Boggi, et al., "Pancreas Preservation with University of Wisconsin and Celsior Solutions," Transplant Proc. 36(3):563-5 (2004).
Boggi, et al., "Pancreas Preservation with University of Wisconsin and Celsior Solutions: A Single-Center Prospective, Randomized Pilot Study," Transplantation 27:77(8):1186-90 (2004).
Boyle, Jr. et al., "Ischemia-Reperfusion Injury," Ann. Thorac. Surg. 64:524-30 (1997).
Burt, et al, "Myocardial Function After Preservation for 24 Hours," Jour. Thorac. and Cardiovascular Surg., 92(2):238-46 (1986).
Brasile, et al., "Organ Preservation Without Extreme Hypothermia Using an Oxygen Supplemented Perfusate," Art. Cells. Blood Subs. and Immob. Biotech., 22(4):1463-68 (1994).
Calhoon, et al., "Twelve-Hour Canine Heart Preservation With a Simple, Portable Hypothermic Organ Perfusion Device," Ann. Thorac. Surg., 62:91-3 (1996).
Canelo R., et al., "Experience with Hystidine Tryptophan Ketoglutarate Versus University Wisconsin Preservation Solutions in Transplatation," Int. Surg. 88(3):145-51 (2003).
"CELSIOR Cold Storage Solution," Sangstat Medical Corporation (internet reference) (1999).
Chambers, et al., "Long-Term Preservation of the Heart: The Effect of Infusion Pressure During Continuous Hypothermic Cardioplegia," Jour. of Heart and Lung Transp., 11(4):665-75 (1992).
Chen, et al., "Development of New Organ Preservation Solutions in Kyoto University," Yonsei Medical Journal, 46(6):1107-40 (2004).
Chien, et al., "A Simple Technique for Multiorgan Preservation," Jour. of Thor. and Card. Surg., 95(1):55-61 (1988).
Chien, et al., Canine Lung Transplantation After More Than Twenty-four Hours of Normothermic Preservation, J. Heart Lung Transplant, 16:3340-51 (1997).
Chien, et al., "Functional Studies of the Heart During a 24-Hour Preservation Using a New Autoperfusion Preparation," The Journal of Heart and Lung Transplantation, 10(3):401-8 (1991).
Cimino, Adria, "Doctor Develops Device to Preserve Donated Organs," Mass High Tech (2001).
Christophi, et al., "A Comparison of Standard and Rapid Infusion Methods of Liver Preservation During Multi-Organ Procurement," Aust. N.Z.J. Surg., 61(9):692-94 (1991).
Collins, B.H., "Organ Transplantatin: What is the State of the Art?," Ann. Surg., 238(6 Suppl):S72-89 (2003).
Cronin, et al., "Liver Transplantation at the University of Chicago," Clin. Transpl. 231-8 (1999).
Daemen, et al., "Short-Term Outcome of Kidney Transplants Fron Non-Heart-Beating Donors After Preservation by Machine Perfusion," Transpl. Int. 9(Supp 1):S76-S80 (1996).
Demertzis et al., "University of Wisconsin Versus St. Thomas' Hospital Solution for Human Donor Heart Preservation," Ann. Thorac. Surg. 55:1131-7 (1993).
Den Butter, et al., "Comparison of Solutions for Preservation of the Rabbit Liver as Tested by Isolated Perfusion," Transpl. Int. 8(6):466-71 (1995).
Denham, et al., "Twenty-Four Hour Canine Renal Preservation by Pulsatile Perfusion, Hypothermic Storage, and Combinations of the Two Methods," Transplant Proc. 9(3):1553-56 (1977).
Dobrian, et al., "In vitro formation of oxidatively-modified and reassembled human low-density lipoproteins," Biochimica et Biophysica Acta (BBA) 1169:12-24 (1993).
Drexler et al., "Effect of L-Arginine on Coronary Endothelial Function in Cardiac Transplant Recipients," Circulation. 89(4):1615-23 (1994).
Eiseman, et al., "A Disposable Liver Perfusion Chamber," Surgery 6:1163-66 (1966).
Engelman et al. "Influence of Steroids on Complement and Cytokine Generation After Cardiopulmonary Bypass," Ann. Thorac. Surg. 60(3):801-04 (1995).

Fabregas, Luis, "UPMC Tests Machine to Aid Heart Transplants," Pittsburg Tribune-Review (2002).
Faggian, et al., "Donor Organ Preservation in High-Risk Cardiac Transplantation," Transplant Proc. 36:617-19 (2004).
Fehrenberg, et al., "Protective Effects of B2 Preservation Solution in Comparison to a Standard Solution (Histidine-Tryptophan-Ketoglutarate/Bretschneider) in a Model of Isolated Autologous Hemoperfused Porcine Kidney," Nephron. Physiol. 96:52-58 (2004).
Ferrera et al., "Comparison of Different Techniques of Hypothermic Pig Heart Preservation," Ann. Thorac. Surg. 57(5):1233-39 (1994).
Finn et al., Effects of Inhibition of Complement Activation Using Recombinant Soluble Complement Receptor 1 on Neutrophil CD11B/CD18 and L-Selectin Expression and Release of Interleukin-8 and Elastase in Simulated Cardiopulmonary Bypass. J. Thorac. Cardiovasc. Surg. 111(2):451-49 (1996).
Fourcade, et al., "A New Method of Kidney Preservation with Collins' Solution," Biomed. 21(7):308-11 (1974).
Fraser, et al., "Evaluation of Current Organ Preservation Methods for Heart-Lung Transplantation," Transplant. Proc. 20(1 Suppl. 1):987-90 (1988).
Guarrera, et al., "Pulsatile Machine Perfusion with Vasosol Solution Improves Early Graft Function After Cadaveric Renal Transplantation," Transplantation 77(8):1264-68 (2004).
Gundry et al., "Successful Transplantation of Hearts Harvested 30 Minutes After Death From Exsanguination," Ann. Thorac. Surg. 53(5):772-75 (1992).
Habazetti et al., "Improvement in Functional Recovery of the Isolated Guinea Pig Heart After Hyperkalemic Reperfusion with Adenosine," J. Thorac. Cardiovasc. Surg. 111(1):74-84 (1996).
Hachida, et al., Abstract "Efficacy of Myocardial Preservation using HTK Solution in Continuous 120 Min. Cross-Clamping Method—A Comparative Study with GIK Method," Nippon Kyobu Geka Gakkai Zasshi 41(9):1495-1501 (1993).
Hartman, J.C. "The Role of Bradykinin and Nitric Oxide in the Cardioprotective Action of ACE Inhibitors," Ann Thor. Surg. 60:789-92 (1995).
Hassanein, et al., "A Novel Approach for 12-Hour Donor Heart Preservation, Presented at the 70th Scientific Session of The American Heart Association," Abstract was published in Circulation (1977).
Hassanein, et al., "Continuous Perfusion of Donor Hearts in the Beating State Extends Preservation Time and Improves Recovery of Function," The Journal of Thoracic and Cardiovascular Surgery, pp. 821-830 (1988).
"Heart Kept Beating Outside Body," Associated Press, CNN.com (2001).
Heil, et al., "A Controlled Comparison of Kidney Preservation by Two Methods: Machine Perfusion and Cold Storage," Transplant. Proc. 19(1):2046 (1987).
History of Transplantation and Organ Preservation, Barr Laboratories,Inc. (internet reference) (2004).
"Human Heart Beats on its own Outside Body," USA Today (2001).
"Human Heart Kept Alive Outside Body for First Time in Study of Portable Organ Preservation System™ at University of Pittsburgh Medical Center," UPMC, McGowan Institute for Regenerative Medicine (2001).
Imber, et al., "Advantages of Normothermic Perfusion Over Cold Storage in Liver Preservation," Transplantation, 73(5):701-09 (2002).
Janssen, et al., "UW is Superior to Celsior and HTK in the Protection of Human Liver Endothelial Cells Against Preservation Injury," Liver Transpl., 10(12):1514-23 (2004).
Kawamura, et al., "Long-Term Preservation of Canine Pancreas by a New Simple Cold Storage Method Using Perfluorochemical—The Two-Layer Cold Storage Method (Euro-Collins' Solution/Perfluorochemical)," Kobe J. Med. Sci., 38(2):135-45 (1992).
Kelly, "Current Strategies in Lung Preservation," J. Lab Clin. Med., 136:427-40 (2000).
Keshavjee, et al., "A Method for Safe Twelve-Hour Pulmonary Preservation," J. Thorac Cardiovasc Surg., 98:529-34 (1989).

(56) References Cited

OTHER PUBLICATIONS

Kioka, et al., "Twenty-Four-Hour Isolated Heart Preservation by Perfusion Method With Oxygenated Solution Containing Perfluorochemicals and Albumin," J. Heart Transplant., 5:437-43 (1986).
Kozaki, et al., "Usefulness of a Combination of Machine Perfusion and Pentoxifylline for Porcine Liver Transplantation From Non-Heart-Beating Donors With Prolonged Hypotension," Transplant Proc., 29:3476-77 (1997).
Kuroda, et al., "A New, Simple Method for Cold Storage of the Pancreas Using Perfluorochemical," Transplantation, 46(3):457-60 (1988).
Lasley, et al., "Protective Effects of Adenosine in the Reversibly Injured Heart," Ann. Thorac. Surg., 60(3):843-46 (1995).
Lawrence, "Machine Preserves Organs Outside Body," Chicago Sun Times (2001).
Lefer, A.M., "Attenuation of Myocardial Ischemia-Reperfusion Injury With Nitric Oxide Replacement Therapy." Ann. Thorac. Surg. 60(3):847-51 (1995).
Li, et al., "Insulin in University of Wisconsin Solution Exacerbates the Ischemic Injury and Decreases the Graft Survival Rate in Rat Liver Transplantation," Transplantation, 15:76(1):44-49 (2003).
Li, et al., "Insulin in UW Solution Exacerbates Hepatic Ischemia/ Reperfusion Injury by Energy Depletion Through the IRS-2/ SREBP—1C Pathway," Liver Transp., 10(9):1173-82 (2004).
Li, G. et al., "Functional Recovery in Rabbit Heart after Preservation with a Blood Cardioplegic Solution and Perfusion," J. Herat Lung Transplant. 12(2)263-70 (1993).
Liu, et al., "Annexin V Assay-proven Anti-apopototic Effect of Ascorbic Acid 2-glucoside after Cold Ischemia/Reperfusion Injury in Rat Liver Transplantation," Acta Med. Okayama, 57(5):209-16 (2003).
"Machine Keeps Human Kidney Alive for 24-Hours," 222. worldhealth.net, Aug. 25, 2001.
"Machine May Be Organ Transplant Breakthrough," USA Today (2001).
Mankad et al., "Endothelial dysfunction caused by University of Wisconsin preservation solution in the rat heart," J. Thorac. Cardiovasc. Surg. 104(6): 1618-24 (1992).
Matsuno et al., "Effectiveness of Machine Perfusion Preservation as a Viability Determination Method for Kidneys Procured from Non-Heart-Beating Donors," Transplant. Proc. 26(4):2421-22 (1994).
Matsuno et al., "The Effect of Machine Perfusion Preservation Versus Cold Storage on the Function of Kidneys from Non-Heart-Beating Donors," Transplantation. 57(2):293-94 (1994).
Menasche et al., "Experimental evaluation of Celsior®. a new heart preservation solution," Eur. J. Cardiothor. Surg. 8:207-13 (1994).
Menasche, et al., "Improved Recovery of Heart Transplants With a Specific Kit of Preservation Solutions," J. Thorac. Cardiovasc. Surg., 105(2):353-63 (1993).
Menasche, P., "The inflammatory response to cardiopulmonary bypass and its impact on postoperative myocardial function", Curr. Opin. Cardiology. 10:597-604 (1995).
Moisiuk, et al., "Histidine-Tryptophan-Ketoglutarate Versus Euro-Collins for Preservation of Kidneys from Non-Heart-Beating Donors," Transplant Proc., 28(1):202 (1996).
Moller-Pedersen, et al., "Evaluation of Potential Organ Culture Media for Eye Banking Using Human Donor Corneas," Br. J. Ophthamol, 85(9):1075-79 (2001).
Morimoto, et al., "A Simple Method for Extended Heart-Lung Preservation by Autoperfusion," Trans. Am. Soc. Artif Intern Organs., 30:320-24 (1984).
"New Discovery in Organ Transplantation," MSNBC (2001).
Innovations—Report "New Organ Preservation Solution Easier to Use," (internet reference) (2003).
Nicholson, et al., "A Comparison of Renal Preservation by Cold Storage and Machine Perfusion Using a Procine Autotransplant Model," Transplantation 78(3):333-37 (2004).
Opelz, et al., "Advantage of Cold Storage Over Machine Perfusion for Preservation of Cadaver Kidneys," Transplantation, 33(1):64-68 (1982).
Opelz, et al., "Comparative Analysis of Kidney Preservation Methods, Collaborative Transplant Study," Transplant Proc. 28(1):87-90 (1996).
Pearl et al., "Loss of endothelium-dependent vasodilation and nitric oxide release after myocardial protection with University of Wisconnsin solution," J. Thorac. Cardiovasc. Surg., 107(1):257-64 (1994).
Petrovsky, et al., Justification and Application of a New Method for Transorganic Oxygen Preservation of the Kidneys, Vestn. Akad. Med. Nauk, SSSR., (2):69-82 (1989).
Pinsky et al., "Restoration of the cAMP Second Messenger Pathway Enhances Cardiac Preservation for Transplantation in a Heterotopic Rat Model," J. Clin. Invest. 92(6):2944-3002 (1993).
Ploeg, et al., "Successful 72-Hour Cold Storage of Dog Kidneys with UW Solution," Transplantation, 46(2):191-96 (1988).
Pokorny, et al., "Histidine-Tryptophan-Ketoglutarate Solution for Organ Preservation in Human Liver Transplantation—A Prospective Multi-Centre Observation Study," Transpl. Int. 17(5):256-60 (2004).
Potdar, et al., "Initial Experience Using Histidine-Tryptophan-Ketoglutarate Solution in Clinical Pancreas Transplantation," Clin. Transplant., 18(6):661-65 (2004).
Pozniak, "Keeping Hearts Alive: Doctors Develop a High-Tech System to Salvage Donated Organs," ABC News.com (2001).
Rao et al., "Donor blood Perfusion Improves Myocardial Recovery After Heart Transplantaion," J. Heart Lung Transplant, 16(6):667-73 (1997).
Reddy, et al., "Preservation of Porcine Non-Heart Beating Donor Livers by Sequential Cold Storage and Warm Perfusion," Transplantation, 77(9):1328-32 (2004).
Richens et al., "Clinical Study of Crystalloid Cardioplegia vs Aspartate-Enriched Cardioplegia Plus Warm Reperfusion for Donor Heart Preservation," Transplant. Proc. 24(1): 1608-10 (1993).
Rinder et al., "Blockade of C5a and C5b-9 Generation Inhibits Leukocyte and Platelet Activation during Extracorporeal Circulation," J. Clin. Invest. 96:3(1564-72). 1995.
Rossi, "Portable Organ Preservation System™ Keeps Human Heart Alive Outside Body," PITT Campaign Chronicle (2001).
Rosenkranz, E.R. "Substrate Enhancement of Cardioplegic Solution: Experimental Studies and Clinical Evaluation," Ann. Thorac. Surg. 60:797-800 (1995).
Sato, H. et al., "Supplemental L-Arginine During Cardioplegic Arrest and Reperfusion Avoids Regional Postischemic Injury," J. Thorac. Cardiovasc. Surg. 110(2):302-14 (1995).
Schmid, et al., "The Use of Myocytes as a Model for Developing Successful Heart Preservation Solutions," Transplantation, 52(1):20-6 (Jul. 1991).
Schon, et al., "Liver Transplantation After Organ Preservation by Normothermic Extracorporeal Perfusion," Ann. Surg. 233(1):114-23 (2001).
Schwalb et al., "New Solution for Prolonged Myocardial Preservation for Transplantation," J. Heart Lung Transplant. 17(2):222-29 (1998).
Seccombe et al., "Coronary Artery Endothelial Function After Myocardial Ischemia and Reperfusion," Ann. Thorac. Surg. 60(3):778-88 (1995).
Segel et al., "Posttransplantation Function of Hearts Preserved with Fluorochemical Emulsion", J. Heart Lung Transplant. 13(4):669-80 (1994).
Segel, et al., "Recovery of Sheep Hearts After Perfusion Preservation or Static Storage With Crystalloid Media," The Journal of Heart and Lung Transplantation, 17:211-21 (1998).
Shimokawa, et al., "A New Lung Preservation Method of Topical Cooling by Ambient Cold Air Combined with High-Frequency Oscillation: An Experimental Study," Transplant. Proc., 26(4):2364-66 (1994).
Shimokawa, et al., "A New Lung Preservation Method of Topical Cooling by Ambient Cold Air: An Experimental Study," Transplant. Proc., 23 (1 Pt 1):653-54 (1991).

(56) References Cited

OTHER PUBLICATIONS

Shirakura et al., "Multiorgan Procurement from Non-Heart-Beating Donors by use of Osaka University Cocktail, Osaka Rinse Solution, and the Portable Cardiopulmonary Bypasss Machine," Transplant. Proc. 25(6):3093-94 (1993).
Southard, "The Right Solution for Organ Preservation", Business Briefings: Global Surgery, 79-84 (2004).
Stubenitsky, et al., "Kidney Preservation in the Next Millenium," Transpl. Int., 12:83-91 (1999).
Sunamori et al., "Relative Advantages of Nondepolarizing Solution to Depolarizing University of Wisconsin Solution in Donor Heart Preservation," Transplant. Proc. 25(1): 1613-17 (1993).
Tang, et al., "Warm Ischemia Lung Protection with Pinacidil: An ATP Regulated Potassium Channel Opener," Ann. Thorac. Surg., 76:385-9 (2003).
Tesi et al., "Pulsatile Kidney Perfusion for Preservation and Evaluation: Use of High-Risk Kidney Donors to Expand the Donor Pool," Transplant. Proc. 25(6):3099-100 (1993).
The Merck Index, 11th ed. Entry 4353 (pp. 699-700) (1989).
"The Nation Warm-Storage Device May Aid Organ Transplants," Dow Jones Publications Library (2001).
Turpin, et al., "Perfusion of Isolated Rat Adipose Cells," The Journal of Clinical Investigation, 60:442-448 (1977).
"ViaSpan (Belzer UW) Cold Storage Solution," Barr Laboratories, Inc. (2002).
Vinten-Johansen, et al., "Reduction in Surgical Ischemic-Reperfusion Injury With Adenosine and Nitric Oxide Therapy," Ann. Thorac. Surg. 60(3):852-57 (1995).
"Warm-Storage for Donor Organs," Univ. of Chicago Magazine (2001).
Watanabe, et al., "Effects of free fatty acids on the binding of bovine and human serum albumin with steroid hormones," Biochimica et Biophysica Acta (BGBA), 1289:385-96 (1996).
Wicomb et al., "24-Hour Rabbit Heart Storage with UW Solution," Transplantation. 48(1):6-9 (1989).
Zhengquang, et al., "A Study on the Preservation of Rat Kidney with HX-III Solution," WCUMS, 31(3):347-49 (2000).
Wicomb, et al., "Cardiac Transplantation Following Storage of the Donor Heart by a Portable Hypothermic Perfusion System," The Annals of Thoracic Surgery, 37(3):243-48 (1984).
Wicomb, et al., "Orthotopic Transplantation of the Baboon Heart After 20 to 24 Hours Preservation by Continuous Hypothermic Perfusion With an Oxygenated Hyperosmolar Solution," The Journal of Thoracic and Cardiovascular Surgery, 83(1):133-40 (1982).
Yland, et al., "New Pulsatile Perfusion Method for Non-Heart-Beating Cadaveric Donor Organs: A Preliminary Report," Transplantation Proceedings, 25(6):3087-90 (1993).
Zhang, et al., "Research Progress on Preservation of Severed Limbs," Chinese Journal of Reparative and Reconstructive Surgery, 14(3):189-192 (2000).
"2002 Design & Engineering Awards, Portable Organ Preservation System," Science (2002), 1 page.
"CELSIOR Cold Storage Solution," Sangstat Medical Corporation (1999), 5 pages.
"History of Transplantation and Organ Preservation," Barr Laboratories,Inc. (2004), 4 pages.
"Human Heart Beats on its own Outside Body," USA Today (2001), 1 page.
"Human Heart Kept Alive Outside Body for First Time in Study of Portable Organ Preservation System™ at University of Pittsburgh Medical Center," UPMC, McGowan Institute for Regenerative Medicine (2001), 2 pages.
"Machine May Be Organ Transplant Breakthrough," USA Today (Aug. 2001), 1 page.
"New Discovery in Organ Transplantation," MSNBC (2001), 1 page.
"The Nation: Warm-Storage Device May Aid Organ Transplants," Dow Jones Publications Library (2001), 1 page.
"ViaSpan (Belzer UW) Cold Storage Solution," Barr Laboratories, Inc. (2002), 2 pages.
"Warm-Storage for Donor Organs," Univ. of Chicago Magazine (2001), 1 page.
Ahmad, et al., "A Pathophysiologic Study of the Kidney Tubule to Optimize Organ Preservation Solutions," Kidney Int. 66(1):77-90 (2004), 14 pages.
American Adacemy of Anti-Aging Medicine, "Machine Keeps Human Kidney Alive for 24-Hours," 222.worldhealth.net, Aug. 25, 2001, Accessed Jul. 5, 2006, 1 page.
Anathaswamy, "Machine Keeps Organs Alive for Longer," New Scientist.com (2001), 1 page.
Aoki, M. et al. "Anti-CD18 Attenuates Deleterious Effects of Cardiopulmonary Bypass and Hypothermic Circulatory Arrest in Piglets," J. Card. Surg. 10:407-17 (1995), 11 pages.
Bando, et al., "Oxygenated Perfluorocarbon, Recombinant Human Superoxide Dismutase, and Catalase Ameliorate Free Radical Incuded Myocardial Injury During Heart Preservation and Transplantation," J. Thorac Cardiovasc Surg. 96:930-8 (Dec. 1988), 9 pages.
Belzer, "Formula for Belzer MPS Solution," University of Wisconsin-Madison Organ Preservation (2003), 2 pages.
Benichou, et al., "Canine and Human Liver Preservation for 6 to 18 Hours by Cold Infusion," Transplation, 24(6):407-411 (Dec. 1977), 5 pages.
Birkett et al., "The Fatty Acid Content and Drug Binding Characteristics of Commercial Albumin Preparations," Clin. Chem. Acta. 85:253-58 (1978), 6 pages.
Blanchard, et al., "Techniques for Perfusion and Storage of Heterotopic Heart Transplants in Mice," Microsurgery, 6:169-174 (1985), 6 pages.
Boggi, et al., "Pancreas Preservation with University of Wisconsin and Celsior Solutions," Transplant Proc. 36(3):563-5 (2004), 3 pages.
Boggi, et al., "Pancreas Preservation with University of Wisconsin and Celsior Solutions: A Single-Center Prospective, Randomized Pilot Study," Transplantation 27:77(8):1186-90 (2004), 5 pages.
Boyle, Jr. et al., "Ischemia-Reperfusion Injury," Ann. Thorac. Surg. 64:S24-S30 (1997), 7 pages.
Brasile, et al., "Organ Preservation Without Extreme Hypothermia Using an Oxygent™ Supplemented Perfusate," Art. Cells. Blood Subs. and Immob. Biotech., 22(4):1463-68 (1994), 6 pages.
Burt, et al, "Myocardial Function After Preservation for 24 Hours," Jour. Thorac. and Cardiovascular Surg., 92(2):238-46 (1986), 9 pages.
Calhoon, et al., "Twelve-Hour Canine Heart Preservation With a Simple, Portable Hypothermic Organ Perfusion Device," Ann. Thorac. Surg., 62:91-3 (1996), 3 pages.
Canelo R., et al., "Experience with Hystidine Tryptophan Ketoglutarate Versus University Wisconsin Preservation Solutions in Transplatation," Int. Surg. 88(3):145-51 (2003), 8 pages.
Chambers, et al., "Long-Term Preservation of the Heart: The Effect of Infusion Pressure During Continuous Hypothermic Cardioplegia," Jour. of Heart and Lung Transp., 11(4):665-75 (1992), 11 pages.
Chen, et al., "Development of New Organ Preservation Solutions in Kyoto University," Yonsei Medical Journal, 46(6):1107-40 (2004), 8 pages.
Chien, et al., "A Simple Technique for Multiorgan Preservation," Jour. of Thor. and Card. Surg., 95(1):55-61 (1988), 7 pages.
Chien, et al., "Canine Lung Transplantation After More Than Twenty-four Hours of Normothermic Preservation," J. Heart Lung Transplant, 16:340-51 (1997) 12 pages.
Chien, et al., "Functional Studies of the Heart During a 24-Hour Preservation Using a New Autoperfusion Preparation," The Journal of Heart and Lung Transplantation, 10(3):401-8 (1991), 8 pages.
Christophi, et al., "A Comparison of Standard and Rapid Infusion Methods of Liver Preservation During Multi-Organ Procurement," Aust. N.Z.J. Surg., 61(9):692-94 (1991), 3 pages.
Cimino, Adria, "Doctor Develops Device to Preserve Donated Organs," Mass High Tech (2001), 2 pages.
CNN.com, "Heart Kept Beating Outside Body," Associated Press (2001), 2 pages.
Collins, B.H., "Organ Transplantation: What is the State of the Art?," Ann. Surg., 238(6 Suppl):S72-89 (2003), 18 pages.

(56) References Cited

OTHER PUBLICATIONS

Cronin, et al., "Liver Transplantation at the University of Chicago," Clin. Transpl. 231-8 (1999), 9 pages.
Daemen, et al., "Short-Term Outcome of Kidney Transplants From Non-Heart-Beating Donors After Preservation by Machine Perfusion," Transpl. Int. 9(Supp 1):S76-S80 (1996), 5 pages.
Demertzis et al., "University of Wisconsin Versus St. Thomas' Hospital Solution for Human Donor Heart Preservation," Ann. Thorac. Surg. 55:1131-7 (1993), 7 pages.
den Butter, et al., "Comparison of Solutions for Preservation of the Rabbit Liver as Tested by Isolated Perfusion," Transpl. Int. 8(6):466-71 (1995), 6 pages.
Denham, et al., "Twenty-Four Hour Canine Renal Preservation by Pulsatile Perfusion, Hypothermic Storage, and Combinations of the Two Methods," Transplant Proc. 9(3):1553-56 (1977), 4 pages.
Dobrian, et al., "In vitro formation of oxidatively-modified and reassembled human low-density lipoproteins: antioxident effect of albumin," Biochimica et Biophysica Acta (BBA) 1169:12-24 (1993), 13 pages.
Eiseman, et al., "A Disposable Liver Perfusion Chamber," Surgery 60(6):1183-86 (1966), 4 pages.
Engelman et al. "Influence of Steroids on Complement and Cytokine Generation After Cardiopulmonary Bypass," Ann. Thorac. Surg. 60(3):801-04 (1995), 4 pages.
Fabregas, Luis, "UPMC Tests Machine to Aid Heart Transplants," Pittsburg Tribune-Review (2002), 3 pages.
Faggian, et al., "Donor Organ Preservation in High-Risk Cardiac Transplantation," Transplant Proc. 36:617-19 (2004), 3 pages.
Fehrenberg, et al., "Protective Effects of B2 Preservation Solution in Comparison to a Standard Solution (Histidine-Tryptophan-Ketoglutarate/Bretschneider) in a Model of Isolated Autologous Hemoperfused Porcine Kidney," Nephron. Physiol. 96:52-58 (2004), 7 pages.
Ferrera et al., "Comparison of Different Techniques of Hypothermic Pig Heart Preservation," Ann. Thorac. Surg. 57(5):1233-39 (1994), 7 pages.
Finn et al., "Effects of Inhibition of Complement Activation Using Recombinant Soluble Complement Receptor 1 on Neutrophil CD11B/CD18 and L-Selectin Expression and Release of Interleukin-8 and Elastase in Simulated Cardiopulmonary Bypass." J. Thorac. Cardiovasc. Surg. 111(2):451-49 (1996), 9 pages.
Fourcade, et al., "Nouvelle Methode de Conservation du Rein Avec une Solution de Collins" <<A New Method of Kidney Preservation with Collins' Solution,>> Biomed. 21(7):308-11 (1974), English Abstract, 5 pages.
Fraser, et al., "Evaluation of Current Organ Preservation Methods for Heart-Lung Transplantation," Transplant. Proc. 20(1 Suppl. 1):987-90 (1988), 4 pages.
Glucose, The Merck Index, 11th ed. Entry 4353 (pp. 699-700) (1989), 3 pages.
Guarrera, et al., "Pulsatile Machine Perfusion with Vasosol Solution Improves Early Graft Function After Cadaveric Renal Transplantation," Transplantation 77(8):1264-68 (2004), 5 pages.
Gundry et al., "Successful Transplantation of Hearts Harvested 30 Minutes After Death From Exsanguination," Ann. Thorac. Surg. 53(5):772-75 (1992), 4 pages.
Habazetti et al., "Improvement in Functional Recovery of the Isolated Guinea Pig Heart After Hyperkalemic Reperfusion with Adenosine," J. Thorac. Cardiovasc. Surg. 111(1):74-84 (1996), 11 pages.
Hachida, et al., Abstract "Efficacy of Myocardial Preservation using HTK Solution in Continuous 120 Min. Cross-Clamping Method—a Comparative Study with GIK Method," Nippon Kyobu Geka Gakkai Zasshi 41(9):1495-1501 (1993), 1 page.
Hartman, J.C. "The Role of Bradykinin and Nitric Oxide in the Cardioprotective Action of ACE Inhibitors," Ann Thor. Surg. 60:789-92 (1995), 4 pages.
Hassanein, et al., "A Novel Approach for 12-Hour Donor Heart Preservation, Presented at the 70th Scientific Session of The American Heart Association," Abstract was published in Circulation (1977), 1 page.
Hassanein, et al., "Continuous Perfusion of Donor Hearts in the Beating State Extends Preservation Time and Improves Recovery of Function," The Journal of Thoracic and Cardiovascular Surgery, pp. 821-830 (1998), 10 pages.
Heil, et al., "A Controlled Comparison of Kidney Preservation by Two Methods: Machine Perfusion and Cold Storage," Transplant. Proc. 19(1):2046 (1987), 1 page.
Imber, et al., "Advantages of Normothermic Perfusion Over Cold Storage in Liver Preservation," Transplantation, 73(5):701-09 (2002), 9 pages.
Innovations-Report "New Organ Preservation Solution Easier to Use," www.innovations-report.de/specials/printa.php?id=18854. Dated 2003, Accessed Jul. 21, 2006, 2 pages.
Janssen, et al., "UW is Superior to Celsior and HTK in the Protection of Human Liver Endothelial Cells Against Preservation Injury," Liver Transpl., 10(12):1514-23 (2004), 10 pages.
Kawamura, et al., "Long-Term Preservation of Canine Pancreas by a New Simple Cold Storage Method Using Perfluorochemical—The Two-Layer Cold Storage Method (Euro-Collins' Solution/Perfluorochemical)," Kobe J. Med. Sci., 38(2):135-45 (1992), 11 pages.
Keshavjee, et al., "A Method for Safe Twelve-Hour Pulmonary Preservation," J. Thorac Cardiovasc Surg., 98:529-34 (1989), 6 pages.
Kioka, et al., "Twenty-Four-Hour Isolated Heart Preservation by Perfusion Method With Oxygenated Solution Containing Perfluorochemicals and Albumin," J. Heart Transplant., 5:437-43 (1986), 7 pages.
Kozaki, et al., "Usefulness of a Combination of Machine Perfusion and Pentoxifylline for Porcine Liver Transplantation From Non-Heart-Beating Donors With Prolonged Hypotension," Transplant Proc., 29:3476-77 (1997), 2 pages.
Kuroda, et al., "A New, Simple Method for Cold Storage of the Pancreas Using Perfluorochemical," Transplantation, 46(3):457-60 (1988), 4 pages.
Lasley, et al., "Protective Effects of Adenosine in the Reversibly Injured Heart," Ann. Thorac. Surg., 60(3):843-46 (1995), 4 pages.
Lawrence, "Machine Preserves Organs Outside Body," Chicago Sun Times (2001), 1 page.
Lefer, A.M., "Attenuation of Myocardial Ischemia-Reperfusion Injury With Nitric Oxide Replacement Therapy." Ann. Thorac. Surg. 60(3):847-51 (1995), 5 pages.
Li, et al., "Insulin in University of Wisconsin Solution Exacerbates the Ischemic Injury and Decreases the Graft Survival Rate in Rat Liver Transplantation," Transplantation, 15:76(1):44-49 (2003), 6 pages.
Li, et al., "Insulin in UW Solution Exacerbates Hepatic Ischemia/Reperfusion Injury by Energy Depletion Through the IRS-2/SREBP-$1_C$ Pathway," Liver Transp., 10(9):1173-82 (2004), 10 pages.
Li, G. et al., "Functional Recovery in Rabbit Heart after Preservation with a Blood Cardioplegic Solution and Perfusion," J. Heart Lung Transplant. 12(2)263-70 (1993), 8 pages.
Liu, et al., "Annexin V Assay-proven Anti-apopototic Effect of Ascorbic Acid 2-glucoside after Cold Ischemia/Reperfusion Injury in Rat Liver Transplantation," Acta Med. Okayama, 57(5):209-16 (2003), 8 pages.
Mankad et al., "Endothelial dysfunction caused by University of Wisconsin preservation solution in the rat heart," J. Thorac. Cardiovasc. Surg. 104(6): 1618-24 (1992), 7 pages.
Matsuno et al., "Effectiveness of Machine Perfusion Preservation as a Viability Determination Method for Kidneys Procured from Non-Heart-Beating Donors," Transplant. Proc. 26(4):2421-22 (1994), 2 pages.
Matsuno et al., "The Effect of Machine Perfusion Preservation Versus Cold Storage on the Function of Kidneys from Non-Heart-Beating Donors," Transplantation. 57(2):293-94 (1994), 2 pages.

(56) References Cited

OTHER PUBLICATIONS

Menasche et al., "Experimental evaluation of Celsior®, a new heart preservation solution," Eur. J. Cardiothor. Surg. 8:207-13 (1994), 7 pages.
Menasche, et al., "Improved Recovery of Heart Transplants With a Specific Kit of Preservation Solutions," J. Thorac. Cardiovasc. Surg., 105(2):353-63 (1993), 11 pages.
Menasche, P., "The inflammatory response to cardiopulmonary bypass and its impact on postoperative myocardial function", Curr. Opin. Cardiology. 10:597-604 (1995), 8 pages.
Moisiuk, et al., "Histidine-Tryptophan-Ketoglutarate Versus Euro-Collins for Preservation of Kidneys from Non-Heart-Beating Donors," Transplant Proc., 28(1):202 (1996), 1 page.
Moller-Pedersen, et al., "Evaluation of Potential Organ Culture Media for Eye Banking Using Human Donor Corneas," Br. J. Ophthamol, 85(9):1075-79 (2001), 5 pages.
Morimoto, et al., "A Simple Method for Extended Heart-Lung Preservation by Autoperfusion," Trans. Am. Soc. Artif Intern Organs., 30:320-24 (1984), 5 pages.
Nicholson, et al., "A Comparison of Renal Preservation by Cold Storage and Machine Perfusion Using a Porcine Autotransplant Model," Transplantation 78(3):333-37 (2004), 5 pages.
Opelz, et al., "Advantage of Cold Storage Over Machine Perfusion for Preservation of Cadaver Kidneys," Transplantation, 33(1):64-68 (1982), 5 pages.
Opelz, et al., "Comparative Analysis of Kidney Preservation Methods," Transplant Proc. 28(1):87-90 (1996), 4 pages.
Pearl et al., "Loss of endothelium-dependent vasodilation and nitric oxide release after myocardial protection with University of Wisconsin solution," J. Thorac. Cardiovasc. Surg., 107(1):257-64 (1994), 8 pages.
Petrovsky, et al., "Justification and Application of a New Method for Transorganic Oxygen Preservation of the Kidneys," Vestn. Akad. Med. Nauk, SSSR., (2):69-82 (1989)—English Abstract, 15 pages.
Pinsky et al., "Restoration of the cAMP Second Messenger Pathway Enhances Cardiac Preservation for Transplantation in a Heterotopic Rat Model," J. Clin. Invest. 92(6):2994-3002 (1993), 9 pages.
Ploeg, et al., "Successful 72-Hour Cold Storage of Dog Kidneys with UW Solution," Transplantation, 46(2):191-96 (1988), 6 pages.
Pokorny, et al., "Histidine-Tryptophan-Ketoglutarate Solution for Organ Preservation in Human Liver Transplantation—A Prospective Multi-Centre Observation Study," Transpl. Int. 17(5):256-60 (2004), 5 page.
Potdar, et al., "Initial Experience Using Histidine-Tryptophan-Ketoglutarate Solution in Clinical Pancreas Transplantation," Clin. Transplant., 18(6):661-65 (2004), 5 pages.
Pozniak, "Keeping Hearts Alive: Doctors Develop a High-Tech System to Salvage Donated Organs," ABC News.com (2001), 2 pages.
Rao et al., "Donor blood Perfusion Improves Myocardial Recovery After Heart Transplantaion," J. Heart Lung Transplant, 16(6):667-73 (1997), 7 pages.
Reddy, et al., "Preservation of Porcine Non-Heart Beating Donor Livers by Sequential Cold Storage and Warm Perfusion," Transplantation, 77(9):1328-32 (2004), 5 pages.
Richens et al., "Clinical Study of Crystalloid Cardioplegia vs Aspartate-Enriched Cardioplegia Plus Warm Reperfusion for Donor Heart Preservation," Transplant. Proc. 25(1): 1608-10 (1993), 3 pages.
Rinder et al., "Blockade of C5a and C5b-9 Generation Inhibits Leukocyte and Platelet Activation during Extracorporeal Circulation," J. Clin. Invest. 96:1564-72). 1995, 9 pages.
Rosenkranz, E.R. "Substrate Enhancement of Cardioplegic Solution: Experimental Studies and Clinical Evaluation," Ann. Thorac. Surg. 60:797-800 (1995), 4 pages.
Rossi, "Portable Organ Preservation System™ Keeps Human Heart Alive Outside Body," PITT Campaign Chronicle (2001), 2 pages.
Sato, H. et al., "Supplemental L-Arginine During Cardioplegic Arrest and Reperfusion Avoids Regional Postischemic Injury," J. Thorac. Cardiovasc. Surg. 110(2):302-14 (1995), 13 pages.

Schmid, et al., "The Use of Myocytes as a Model for Developing Successful Heart Preservation Solutions," Transplantation, 52(1):20-6 (Jul. 1991), 7 pages.
Schon, et al., "Liver Transplantation After Organ Preservation by Normothermic Extracorporeal Perfusion," Ann. Surg. 233(1):114-23 (2001), 10 pages.
Schwalb et al., "New Solution for Prolonged Myocardial Preservation for Transplantation," J. Heart Lung Transplant. 17(2):222-29 (1998), 8 pages.
Seccombe et al., "Coronary Artery Endothelial Function After Myocardial Ischemia and Reperfusion," Ann. Thorac. Surg. 60(3):778-88 (1995), 11 pages.
Segel et al., "Posttransplantation Function of Hearts Preserved with Fluorochemical Emulsion", J. Heart Lung Transplant. 13(4):669-80 (1994), 12 pages.
Segel, et al., "Recovery of Sheep Hearts After Perfusion Preservation or Static Storage With Crystalloid Media," The Journal of Heart and Lung Transplantation, 17:211-21 (1998), 11 pages.
Shimokawa, et al., "A New Lung Preservation Method of Topical Cooling by Ambient Cold Air Combined with High-Frequency Oscillation: An Experimental Study," Transplant. Proc., 26(4):2364-66 (1994), 3 pages.
Shimokawa, et al., "A New Lung Preservation Method of Topical Cooling by Ambient Cold Air: An Experimental Study," Transplant. Proc., 23 (1):653-54 (1991), 2 pages.
Shirakura et al., "Multiorgan Procurement from Non-Heart-Beating Donors by use of Osaka University Cocktail, Osaka Rinse Solution, and the Portable Cardiopulmonary Bypass Machine," Transplant. Proc. 25(6):3093-94 (1993), 2 pages.
Stubenitsky, et al., "Kidney Preservation in the Next Millenium," Transpl. Int., 12:83-91 (1999), 9 pages.
Sunamori et al., "Relative Advantages of Nondepolarizing Solution to Depolarizing University of Wisconsin Solution in Donor Heart Preservation," Transplant. Proc. 25(1): 1613-17 (1993), 5 pages.
Tang, et al., "Warm Ischemia Lung Protection with Pinacidil: An ATP Regulated Potassium Channel Opener," Ann. Thorac. Surg., 76:385-9 (2003), 6 pages.
Tesi et al., "Pulsatile Kidney Perfusion for Preservation and Evaluation: Use of High-Risk Kidney Donors to Expand the Donor Pool," Transplant. Proc. 25(6):3099-100 (1993), 2 pages.
Turpin, et al., "Perfusion of Isolated Rat Adipose Cells," The Journal of Clinical Investigation, 60:442-448 (1977), 7 pages.
Vinten-Johansen, et al., "Reduction in Surgical Ischemic-Reperfusion Injury With Adenosine and Nitric Oxide Therapy," Ann. Thorac. Surg. 60(3):852-57 (1995), 6 pages.
Watanabe, et al., "Effects of free fatty acids on the binding of bovine and human serum albumin with steroid hormones," Biochimica et Biophysica Acta (BGBA), 1289:385-96 (1996), 12 pages.
Wicomb et al., "24-Hour Rabbit Heart Storage with UW Solution," Transplantation. 48(1):6-9 (1989), 4 pages.
Wicomb, et al., "Cardiac Transplantation Following Storage of the Donor Heart by a Portable Hypothermic Perfusion System," The Annals of Thoracic Surgery, 37(3):243-48 (1984), 6 pages.
Wicomb, et al., "Orthotopic Transplantation of the Baboon Heart After 20 to 24 Hours Preservation by Continuous Hypothermic Perfusion With an Oxygenated Hyperosmolar Solution," The Journal of Thoracic and Cardiovascular Surgery, 83(1):133-40 (1982), 8 pages.
Yland, et al., "New Pulsatile Perfusion Method for Non-Heart-Beating Cadaveric Donor Organs: A Preliminary Report," Transplantation Proceedings, 25(6):3087-90 (1993), 4 pages.
Zhang, et al., "Research Progress on Preservation of Severed Limbs," Chinese Journal of Reparative and Reconstructive Surgery, 14(3):189-192 (2000)—English Abstrace, 8 pages.
Zhengquang, et al., "A Study on the Preservation of Rat Kidney with HX-III Solution," WCUMS, 31(3):347-49 (2000)—English Abstract, 4 pages.
"Celsior, Cold Storage Solution." Sangstat Medical Corporation and Fresenius Kabi France. (Aug. 1999). 5 pages.
Barinov, et al. "Hormonal-metabolic disturbances during biological preservation of the heart," Fiziol. ZH., (Kiev), 29(3):293-299 (1983) (7 pages)—Russian Language.

(56) References Cited

OTHER PUBLICATIONS

European Search Report for European Patent Application No. 08795820.3 mailed Apr. 17, 2014. 6 pages.
European Search Report for European Patent Application No. 09707471.0 mailed May 27, 2014. 7 pages.
Featherstone et al. "Comparison of Phosphodiesterase Inhibitors of Differing Isoenzyme Selectivity Added to St. Thomas' Hospital Cardioplegic Solution Used for Hypothermic Preservation of Rat Lungs." Am. J. Respir. Crit. Care Med. Mar. 2000. 162(3):850-856. 7 pages.
File History for U.S. Appl. No. 60/616,835, filed Oct. 7, 2004. 82 pages.
File History for U.S. Appl. No. 60/694,971, filed Jun. 28, 2005. 280 pages.
File History for U.S. Appl. No. 60/725,168, filed Oct. 6, 2005. 699 pages.
International Search Report and Written Opinion for International Application No. PCT/US12/33626 mailed Sep. 20, 2012. 12 pages.
Johnson, Kerry et al: "POPS: Portable Organ Preservation System." UPMC Health System and TransMedics, Inc. Tribune Review (No date) 1 page.
Katz, Robert et al. "Physics, Chapter 9: Hydrodynamics (Fluids in Motion)." Hydrodynamics. University of Nebraska-Lincoln. Paper 143. No Month Listed 1958. 18 pages.
No Author Listed. "CUSTODIOL HTK Solution for Multi-Organ Protection." Saudi Center for Organ Transplantation. Date Unknown. 2 pages.
No Author Listed. "Custodiol HTK." Physicians' Desk Reference. 57th Edition, Thomson PDR. ISBN:1-56363-445-7. No Month Listed—2003. 3 pages.
No Author Listed. "SOLTRAN Kidney Perfusion Fluid." Baxter. No Month Listed—2001-2004. 1 page.
No Author Listed. "The Comprehensive Resource for Physicians, Drug and Illness Information." VIASPAN DuPont Pharma Cold Storage Solution. Date Unknown. 3 pages.
No Author Listed. "UW Solution Composition." Date Unknown. 1 page.
PCT/US08/61454 International search report mailed Dec. 5, 2008 (3 pages).
SOLU-MEDROL, Drug Details, U.S. Food and Drug Administration, Center for Drug Evaluation and Research, "Drugs@FDA—Drug Details" (Accessible online at http://www.accessdata.fda.gov/scripts/cder/drugsatfda/index.cfm?fuseaction=Search.DrugDetails) (1 page).
SOLU-MEDROL, Label and Approval History, U.S. Food and Drug Administration, Center for Drug Evaluation and Research, "Drugs@FDA—Label and Approval History," (Available online http://www.accessdata.fda.gov/scripts/cder/drugsatfda/index.cfm?fuseaction=Search.Label_ApprovalHistory#apphist) (3 pages).
Aitchinson et al., "Nitric Oxide During Perfusion Improves Post-transplantation Function of Non-Heart-Beating Donor Lungs," Transplantation, vol. 75, No. 12, pp. 1960-1964 (Jun. 27, 2003).
European Search Report for European Patent Application No. 12770852.7 mailed Sep. 23, 2014, 8 pages.
Johnston, "What's Normal About DLCO?" PFT Blog, Observations, Opinions and Ideas about Pulmonary Function Testing, Jan. 1, 2014, retrieved online at [URL:<<http://www.pftforum.com/blog/whats-normal-about-dlco/>>] on May 12, 2015 (17 pages).
No Author Listed, "Hypoxia and Oxygenation," Alaska Air Medical Escort Training Manual, Chapter 4, Fourth Edition, retrieved online at [URL:<<http://dhss.alaska.gov/dph/Emergency/Documents/ems/assets/AirMedCourse/EMS-F_Chapter4.pdf>>] on Jul. 6, 2015 (pp. 71-82).
Odagiri et al. "New Pulsatile Pump Using Pulsatile Assist Device—Hemodynamic Comparison of Pulsatile V-A Bypass (VABP), Pulsatile Left Hear ByPass (LHBP) and Constant Flow Left Heart Bypass (LHB)." Journal of Japan Surgical Society. V83, No Month Listed 1983. English Abstract pp. 515-523, 12 pages.
Office Action issued by the Japan Patent Office in Japanese Patent Application No. 2012-171812 dated May 26, 2015 (7 pages).
Ota et al. "Artificial Organ—Current State and Future of Substitution of Functions." No Month Listed 1983 pp. 150-151, 7 pages.
Steen et al., "Transplantation of Lungs From Non-Heart-Beating Donors After Functional Assessment Ex Vivo," The Annals of Thoracic Surgery, vol. 76, pp. 244-252, 11 pages (No Month Listed 2003).
Yeung et al., "Physiologic Assessment of the Ex Vivo Donor Lung for Transplantation," The Journal of Heart and Lung Transplantation, vol. 31, No. 10, Oct. 2012 (pp. 1120-1126).
Japanese Office Action Notice of Reasons for Rejection issued in corresponding Japanese Patent Application No. 2014-164178, dispatch date Jul. 29, 2015 (8 pages).
Egan, T. M. et al., "Ex Vivo Evaluation of Human Lungs for Transplant Suitability," Ann. Thorac. Surg., vol. 81, No. 4, pp. 1205-1213 (Apr. 2006) (9 pages).
Howarth, F.C. et al., "Effects of Extracellular Magnesium and Beta Adrenergic Stimulation on Contractile Force and Magnesium Mobilization in the Isolated Rat Heart", Magnesium Research, 7:187-197, 1994 (13 pages).
Poston, R.S. et al., "Optimizing Donor Heart Outcome After Prolonged Storage with Endothelial Function Analysis and Continuous Perfusion", Ann. Thorac. Surg., 78:1362-1370, 2004 (9 pages).

\* cited by examiner

SYSTEMS AND METHODS FOR EX VIVO LUNG CARE

REFERENCE TO RELATED APPLICATIONS

This application claims priority to and the benefit of U.S. Provisional Application Ser. No. 61/024,976, filed on Jan. 31, 2008, the entire contents of which are incorporated herein by reference.

FIELD OF THE INVENTION

The invention generally relates to systems, methods, and devices for ex vivo organ care. More particularly, in various embodiments, the invention relates to a portable device for caring, assessing, and applying therapeutic measures to a lung or a pair of lungs ex vivo at physiologic or near-physiologic conditions.

BACKGROUND OF THE INVENTION

Current organ preservation techniques typically involve hypothermic storage of the organ in a chemical preservation solution on ice. These techniques utilize a variety of solutions, none of which sufficiently protect the organ from damage resulting from ischemia. Such injuries are particularly undesirable when an organ is intended to be transplanted from a donor into a recipient.

Effective physiologic preservation of an ex vivo organ would provide important benefits compared to conventional approaches. For instance, physiologic ex vivo preservation would permit more careful monitoring, functional testing, assessment, and therapy of the harvested organ. This would in turn allow earlier detection and potential repair of defects in the harvested organ, further reducing the likelihood of post-transplant organ failure. The ability to perform and assess simple repairs on the organ would also allow many organs with minor defects to be saved, whereas current transplantation techniques require them to be discarded. This is of crucial importance when harvesting lungs because lungs are easily compromised even before harvesting within the donor's body.

In addition, more effective matching between the organ and a particular recipient may be achieved, further reducing the likelihood of eventual organ rejection. Current transplantation techniques rely mainly on matching donor and recipient blood types, which by itself is a relatively unreliable indicator of whether or not the organ will be rejected by the recipient. A more preferred test for organ compatibility is a Human Leukocyte Antigen (HLA) matching test, but current cold ischemic organ preservation approaches preclude the use of this test, which can often require 12 hours or more to complete.

Using conventional approaches, injuries caused by ischemia increase as a function of the length of time an organ is maintained ex vivo. For example, a lung may typically be preserved ex vivo for only about 6 to about 8 hours before it becomes unusable for transplantation. A heart typically may be preserved ex vivo for only about 4 to about 6 hours before it becomes unusable for transplantation. These relatively brief time periods limit the number of recipients who can be reached from a given donor site, thereby restricting the recipient pool for a harvested organ. Even within the time limits, the organs may nevertheless be significantly damaged. A significant issue is that there may not be any observable indication of the damage. Because of this, less-than-optimal organs may be transplanted, resulting in post-transplant organ dysfunction or other injuries. Thus, it would be desirable to develop techniques that can extend the time during which an organ can be preserved in a healthy state ex vivo. Such techniques would reduce the risk of post-transplant organ failure and enlarge potential donor and recipient pools.

Prolonged and reliable ex vivo organ care would also provide benefits outside the context of organ transplantation. For example, a patient's body, as a whole, can typically tolerate much lower levels of chemo-, bio- and radiation therapy than many particular organs. An ex vivo organ care system would permit an organ to be removed from the body and treated in isolation, reducing the risk of damage to other parts of the body.

In view of the foregoing, improved systems, methods, and devices for caring for an organ ex vivo are needed.

SUMMARY OF THE INVENTION

The invention addresses the deficiencies in the state of the art by, in various embodiments, providing improved systems, methods, solutions and devices relating to portable ex vivo organ care.

In general, in one aspect, the invention features a lung care system that includes: a portable multiple use module including a portable chassis, a single use disposable module including: an interface adapted to couple the single use disposable module with the multiple use module for electromechanical interoperation with the multiple use module; and a lung chamber assembly having a first interface for allowing a flow of a perfusion fluid into the lung, a second interface for allowing ventilation of the lung with a ventilation gas, and a third interface for allowing a flow of the perfusion fluid away from the lung, the lung chamber assembly including a dual drain system for carrying the flow of the perfusion fluid away from the lung, the dual drain system comprising a measurement drain for directing a part of the perfusion fluid flow to a sensor of a perfusion fluid gas content and a main drain for receiving a remaining part of perfusion fluid flow. In one embodiment, the lung care system includes a drainage system for draining the perfusion fluid from the lung chamber assembly, the drain system including a measurement conduit and a main drain conduit, the measurement conduit further directing a flow of perfusion fluid to a sensor that is adapted to measure a perfusion fluid gas content.

Other embodiments include one or more of the following features. The dual drain includes a vessel for receiving the perfusion fluid flow, and overflow from the vessel flows to the main drain. The system includes a pump for the circulating the perfusion fluid, and a ventilation system for ventilating the lung with a gas having a predetermined composition. The gas includes oxygen, carbon dioxide. The portable multiple use module includes a lung console for providing at least one of electrical, pneumatic, and mechanical control of the disposable module; the lung console includes a ventilation controller for controlling ventilation of the lung, and includes a mechanical actuator for actuating a bellows to cause flow of gas into the lung. The lung console pneumatic control system controls one or valves in a ventilation gas circuit connected to the lung in the disposable module. The pneumatic control system controls at least one of a bellows valve for cutting off flow between the lung and the bellows, a relief valve for venting ventilation gas, and a trickle valve for introducing gas into the ventilation gas circuit. The ventilation controller selects the gas that is used to ventilate the lung from one of an oxygenation gas, a deoxygenation gas, and a maintenance gas. The oxygenation gas is air, or a gas containing between 25% and 100% oxygen. The deoxygenation gas is composed of carbon dioxide and nitrogen, and the maintenance gas is composed of oxygen, carbon dioxide, and nitrogen. In one embodiment, the deoxygenation gas is about 6% carbon dioxide and about 94% nitrogen, and the maintenance gas is about 12% oxygen, about 5.5% carbon dioxide, and about 82.5% nitrogen. The multiple use module includes a perfusion fluid controller that can control a level of gas content, such as oxygen, in the perfusion fluid. The perfusion fluid controller controls a perfusion fluid gas component, for example by controlling the flow of gas into a gas exchanger that exchanges gas between the flow of gas and the perfusion fluid. The gas flowing into the gas exchanger is a deoxygenation gas that removes oxygen from the perfusion fluid. The multiple use monitor includes a monitor for displaying the status of the lung case system; the status includes information about the oxygen content of the perfusion fluid entering the lung and exiting the lung. It also displays real time traces of the ventilation gas pressure and the pulmonary arterial pressure.

In general, in another aspect, the invention features a lung care module comprising: a single use disposable module including an interface adapted for attachment to the multiple use module, and a lung chamber assembly having a first interface for allowing a flow of a perfusion fluid into the lung and a second interface for allowing ventilation of the lung with a ventilation gas; and a drain system for draining a flow of perfusion fluid from the lung chamber assembly, the drain system including a measurement conduit and a main drain conduit, the measurement conduit further directing a flow of perfusion fluid to a sensor that is adapted to measure a perfusion fluid gas content.

Other embodiments include one or more of the following features. The module includes a system for ventilating the lungs with one of a maintenance gas, an assessment gas, and an oxygenation gas, such as air. The system can be configured to cause the lung to rebreath a volume of gas. The ventilation system ventilates the lung with a maintenance gas having a composition of about 12% oxygen, about 5.5% carbon dioxide, and about 82.5% nitrogen. The lung is ventilated by using a mechanically actuated bellows. The ventilation system further includes a trickle valve for introducing a flow of maintenance gas, and a relief valve for venting excess gas. The second interface to the lungs comprises a tracheal cannula, which has an insertion portion for inserting into the trachea, and a connector portion for connecting to the ventilation gas circuit. The first interface to the lungs includes a pulmonary artery cannula, which includes an insertion portion for inserting into the pulmonary artery and a connector portion for connecting to the perfusion fluid circuit. It also includes a pressure transducer connector defining an opening into a lumen of the connector portion near the insertion tube for positioning a pressure transducer near a point of entry of the perfusion fluid into the lung. The pressure transducer connector further provides a channel for the pressure transducer to be remotely vented.

In general, in yet another aspect, the invention features a lung chamber assembly comprising: a housing having a bottom including at least one housing drain, and walls; a support surface for supporting a lung, the support surface defining a drain and drainage channels leading to the drain for draining a perfusion fluid exiting the lung; an openable lid that provides a sealable connection to the walls of the housing; a first interface for allowing a flow of the perfusion fluid into the lung; a second interface for allowing ventilation of the lung; and a third interface for allowing a flow of the perfusion fluid away from the lung.

Other embodiments include one or more of the following features. The housing includes a drain system for carrying the flow of the perfusion fluid away from the lung, the drain system comprising a measurement drain for directing a part of the perfusion fluid flow to a sensor of a perfusion fluid gas content and a main drain for receiving a remaining part of perfusion fluid flow. The drain system has a region for collecting the flow of perfusion fluid away from the lung into a pool that feeds the measurement drain, the measurement drain having a drainage capacity less than a flow rate of the perfusion fluid away from the lung. Flow of perfusion fluid overflowing the region flows to the main drain. In some embodiments, the drain system further includes a wall partially surrounding the measurement drain, the wall partially blocking a flow of perfusion fluid from the measurement drain to the main drain, the wall promoting formation of a pool of perfusion fluid above the measurement drain. The housing of the lung chamber defines openings that provide sealed passage through the housing of a pulmonary artery cannula, a pulmonary artery pressure transducer conduit, and a tracheal cannula. In some embodiments the perfusion fluid exits the lung through an exposed left atrial cuff, and flows into a drainage system. In other embodiments, the flow of perfusion fluid exiting the lung passes through a sealed connection to a left atrial cannula, which is connected to a conduit that carries the perfusion fluid away from the lung. A part of the perfusion fluid flow passes an oxygen content sensor, and the remainder flows to a reservoir.

In general, in a further aspect, the invention features a method of evaluating a lung including: positioning the lung in an ex vivo perfusion circuit; circulating a perfusion fluid through the lung, the fluid entering the lung through a pulmonary artery interface and leaving the lung through a left atrial interface; ventilating the lung by flowing a ventilation gas through a tracheal interface; deoxygenating the perfusion fluid until a predetermined first value of oxygen content in the perfusion fluid is reached; reoxygenating the perfusion fluid by ventilating the lung with an oxygenation gas until a predetermined second value of oxygen content in the perfusion fluid is reached; and determining a condition of the lung based on a time taken for the lung to cause the oxygen content level in the perfusion fluid to change from the first value of oxygen content to the second value of oxygen content.

Other embodiments include one or more of the following features. The perfusion fluid is deoxygenated by ventilating the lung with a ventilation gas comprising carbon dioxide and nitrogen, for example about 5.5% carbon dioxide and about 94.5% nitrogen. The perfusion fluid is deoxygenated by circulating the perfusion fluid through a gas exchange device, the gas exchange device being in fluid communication with a ventilation gas comprising carbon dioxide and nitrogen, the gas exchange device altering a composition of oxygen in the perfusion fluid by gas exchange between the ventilation gas and the perfusion fluid. The predetermined first value of oxygen content corresponds to a red blood cell saturation of about 73%. The oxygenation gas is air, or a gas comprising between about 25% and about 100% oxygen. The predetermined second value of oxygen content corresponds to a red blood cell saturation of about 93%. The perfusion fluid flows at a rate of about 1.5 liters per minute, and is warmed by a heater to a near-physiologic temperature level. The perfusion fluid is composed of whole blood, or of a blood product, such as blood partially depleted of leukocytes, or partially depleted of platelets. Various therapeutics are delivered to the ling during perfusion via the perfusion fluid, or through the tracheal interface using a nebulizer or a bronchoscope. Oxygen levels in the perfusion fluid are measured using a pulse oxymeter that determines the red blood cell saturation in the fluid.

In general in a further aspect, the invention features a method of preserving a lung ex vivo comprising: circulating a perfusion fluid through the lung, the fluid entering the lung through a pulmonary artery interface and leaving the lung through a left atrial interface; ventilating the lung through a tracheal interface by flowing a captive volume of a ventilation gas back and forth between the lung and a variable volume chamber; and introducing into the captive volume an additional volume of the ventilation gas and venting excess ventilation gas from the captive volume to maintain a predetermined composition of the ventilation gas and to maintain a minimum gas pressure of the captive volume.

Other embodiments include one or more of the following features. The ventilation gas includes a composition of oxygen, carbon dioxide and an inert gas, such as nitrogen. The perfusion fluid reaches an equilibrium level corresponding to a predetermined composition of the ventilation gas. The predetermined composition of the ventilation gas includes about 5-20% oxygen and about 2-10% carbon dioxide. A gas content of the perfusion fluid reaches an equilibrium level, the equilibrium level having a hemoglobin saturation level of about 88%-98%.

The predetermined composition of the ventilation gas includes about 12% oxygen and about 5.5% carbon dioxide. The hemoglobin saturation level of the perfusion fluid entering the lung reaches an equilibrium level of about 90-95% and a hemoglobin saturation level of the perfusion fluid leaving the lung reaches an equilibrium level of about 90-95%. The oxygen content of the perfusion fluid entering the lung is lower than physiologic levels, and the oxygen content of perfusion fluid leaving the lung is higher than physiologic levels. The following parameters are used in certain embodiments: the additional flow of ventilation gas is about 400-600 mL per minute; the captive volume is about 400-1200 mL; the minimum gas pressure of the captive volume is about 4-8 cm of $H_2O$; and the maximum pressure of the ventilation gas is about 12-22 cm of $H_2O$. Excess ventilation gas is vented through a relief valve in communication with the captive volume. The variable volume chamber is a bellows; compressing the bellows causes the flow of ventilation gas into the lung. The pulmonary artery interface includes a pulmonary artery cannula, a portion of the pulmonary artery cannula being inserted into a pulmonary artery of the lung. The perfusion fluid to flows away from the lung through an exposed left atrial cuff of the lung, or through a sealed or semi-sealed connection between the left atrial cuff and a left atrial cannula. The tracheal interface includes a tracheal cannula, a portion of the tracheal cannula being inserted into a trachea of the lung. The method includes measuring a first level of oxygen content in the perfusion fluid flowing into the lung and a second level of oxygen content in the perfusion fluid flowing out of the lung. The oxygen measurement involves measuring at least one of a level of oxygen saturation of hemoglobin in the perfusion fluid and a partial pressure of oxygen in the perfusion fluid flowing into the lung and flowing out of the lung. The perfusion fluid includes a blood product, and can deliver therapeutics to the lung. The gas exchange in the lung between the ventilation gas and the perfusion fluid causes the level of one or more gases, such as oxygen and carbon dioxide, in the perfusion fluid to reach equilibrium values.

The lung may be preserved for a period of about 3-24 hours when maintained with the equilibrium levels of gas.

BRIEF DESCRIPTION OF THE DRAWINGS

The following figures depict illustrative embodiments of the invention in which like reference numerals refer to like elements. These depicted embodiments may not be drawn to scale and are to be understood as illustrative of the invention and not as limiting.

FIG. 1B shows the gas-related components of the lung perfusion module.

DETAILED DESCRIPTION

Figure 1A:
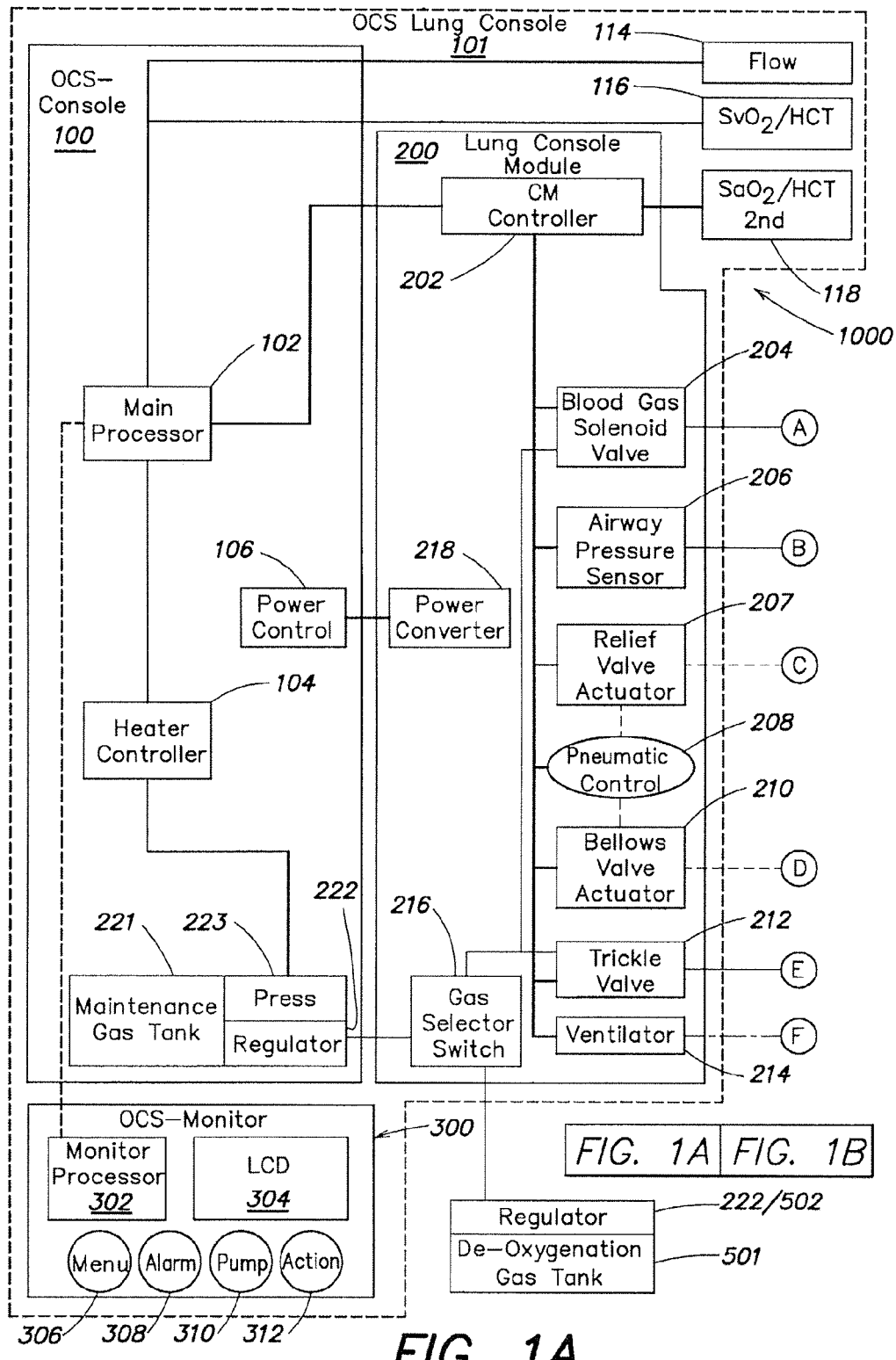
FIGS. 1A-1B are a schematic diagram of the described embodiment of a portable organ care system.

As described above in summary, the described embodiment generally provides improved approaches to ex vivo lung care, particularly in an ex vivo portable environment. The organ care system maintains a lung in an equilibrium state by circulating a perfusion fluid through the lung's vascular system, while causing the lung to rebreath a specially formulated gas having about half the oxygen of air. The perfusion fluid circulates by entering the pulmonary artery (PA) via a cannula inserted into the PA. After passing through the lung, the perfusion fluid exits the lung from an open, uncannulated left atrium (LA) where it drains into a reservoir. A pump draws the fluid out of the reservoir, passes it through a heater and a gas exchanger, and back into the cannulated PA. In the described embodiment, the perfusion fluid is derived from donor blood. In alternative embodiments, the perfusion fluid is blood-product based, synthetic blood substitute based, a mixture of blood product and blood substitute, or derived from blood from a blood bank.

The described embodiments enable a lung to be maintained ex vivo for extended periods of time, such as, for example, 3-24 or more hours. Such extended ex vivo maintenance times expand the pool of potential recipients for donor lungs, making geographic distance between donors and recipients less important. Extended ex vivo maintenance times also provide the time needed for better genetic and HLA matching between donor organs and organ recipients, increasing the likelihood of a favorable outcome. The ability to maintain the organ in a near physiologic functioning condition also enables a clinician to evaluate the organ's function ex vivo, and identify organs that are damaged. This is especially valuable in the case of the lung, since lungs are often compromised as a direct or indirect result of the cause of the death of the donor. Thus even a newly harvested lung may be damaged. The ability to make a prompt assessment of a harvested organ enables a surgeon to determine the quality of a lung and, if there is damage, to make a determination of the nature of the problem. The surgeon then makes a decision as to whether to discard the lung, or to apply therapy to the lung. Therapies can include recruitment processes, removing or stapling off damaged areas of lung, suctioning secretions, cauterizing bleeding blood vessels, and giving radiation treatment. The ability to assess and, if necessary provide therapy to lungs at several stages from harvesting to implantation greatly improves the overall likelihood of lung transplant success. In some instances, the improved assessment capability and extended maintenance time enables medical operators to perform physical repairs on donor organs with minor defects. Increased ex vivo organ maintenance times can also enable an organ to be removed from a patient, treated in isolation ex vivo, and then put back into the body of a patient. Such treatment may include, without limitation, pharmaceutical treatments, gas therapies, surgical treatments, chemo-, bio-, gene and/or radiation therapies.

The lung care system is described below in the following order. First, an overview of the components of an illustrative organ care system is given. Second, illustrative operation of the system is discussed, starting with preparing a lung and mounting it in the system. Third the use of the system for maintaining a lung is described. Two methods of assessing a lung are then described in the fourth and fifth sections—continuous assessment mode, and sequential assessment mode. Sixth, the functioning of the lung ventilator pneumatic circuit is described. Seventh, exemplary organ care system user interfaces and system displays are shown during lung maintenance and assessment. Eighth, illustrative implementations of the organ care system and selected components are described. In the ninth section, illustrative models for using the organ care system are described.

Overview of Organ Care System

Figure 1B:
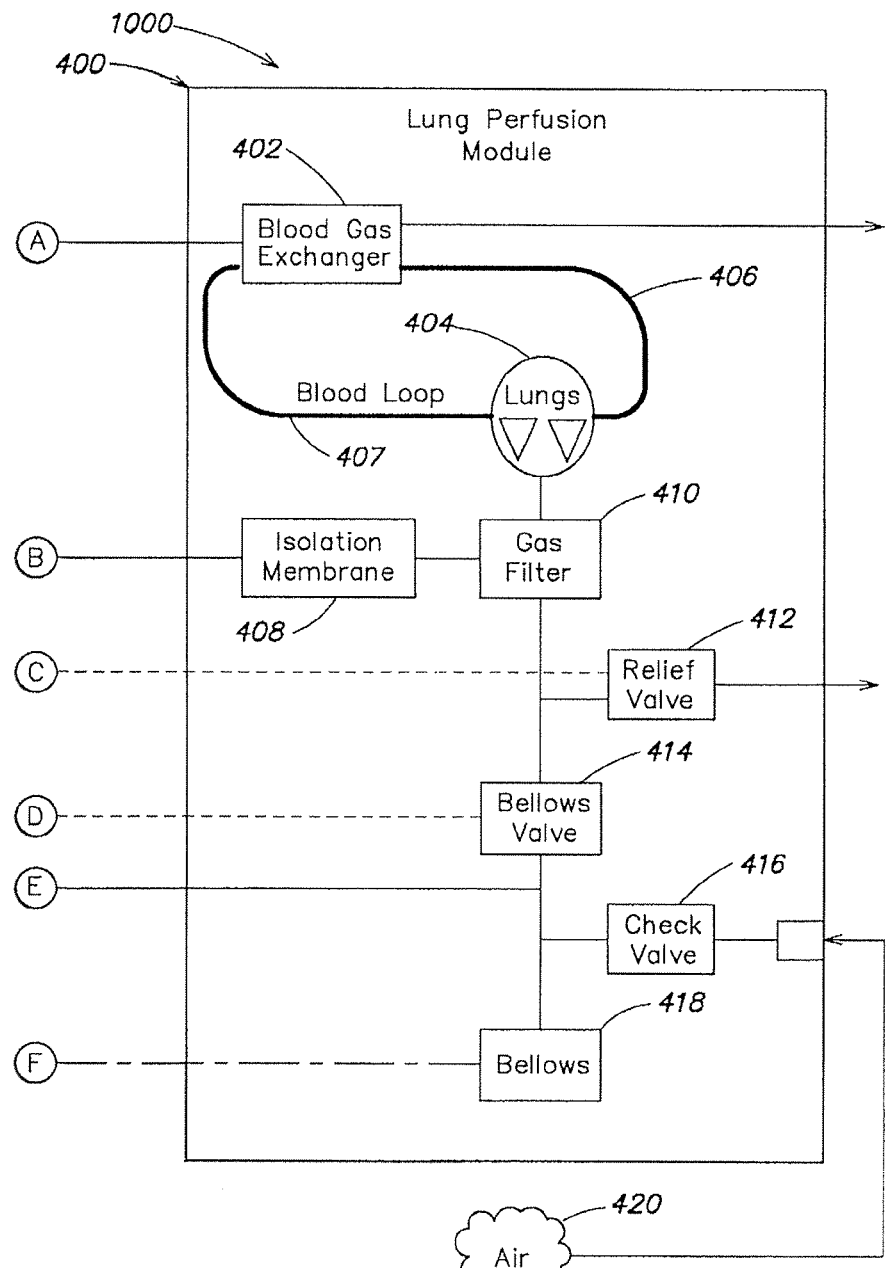

FIG. 1 is a block diagram that shows the main components of an organ care system (OCS) 1000 adapted to the preservation and treatment of a lung. The organ care system includes a permanent, multiple use, non-disposable section, OCS lung console 101, and a single use disposable section, lung perfusion module 400, which is in direct contact with the physical lungs, and the gases and fluids that pass through it. Multiple use OCS lung console 101 includes four components: OCS console 100, lung console module 200, OCS monitor 300, and probes for measuring flow (114), and perfusion fluid oxygen and hematocrit levels (116, 118). In the described embodiment, OCS 1000 is a self contained, mobile and portable unit, and can readily be handled by one person for transport on a flat surface using wheels, or lifted by two people, such as when being loaded into a vehicle. When loaded with an organ and perfusion fluid, OCS 1000 weighs about 75-100 pounds, and preferably about 80 pounds.

OCS console 100 provides processing, temperature, and power control services to the system. During the manufacturing process, OCS console 100 is adapted for use with OCS lung console module 200. Alternatively, OCS console 100 can be adapted for use with modules that are adapted to preserve organs other than the lung, such as the heart, liver, or kidney. OCS console 100 includes main processor 102, which is a Freescale MX1 in the described embodiment, to provide system control and process data. Main processor 102 distributes software to other processors in the system, including lung console module controller 202, heater controller 104, OCS monitor processor 302, and pump controller (not shown). It also manages data, such as that received from flow sensor 114, pressure sensor 115, and oxygen sensors 116, 118.

Heater controller 104, which is a PIC microcontroller in the described embodiment, controls the heating of the perfusion fluid. Pressure transducer 223 measures the pressure of internal maintenance gas in tank 221, so that the amount of gas remaining can be determined. Regulator 222 converts the gas tank pressure to 25 mm Hg for use in the system. Internal maintenance gas tank 221 contains a mixture that is designed to provide enough oxygen to maintain the lung tissue during maintenance mode, described below. In the described embodiment, the maintenance gas is composed of 12% oxygen, 5.5% carbon dioxide, and 82.5% nitrogen. In some embodiments, OCS console 100 also includes an internal deoxygenation gas tank, regulator, and pressure transducer (not shown), which is used during assessment of the lungs. Assessment modes are described in a later section.

The functions specific to the preservation of a lung (as opposed to other organs) are controlled by lung console module 200. Lung console module 200 is connected to OCS console 100 with data, power, and gas connections. The data connection links main processor 102 on OCS console 100 with lung console module controller 202, which is implemented on a PIC microcontroller in the described embodiment. The power connection links the OCS console's power control module 106 with power converter 218, which in turn supplies power at the appropriate voltage to the powered components within lung console module 200. The gas connection runs from maintenance gas regulator 222 to gas selector switch 216, which selects whether maintenance gas or deoxygenation gas flows into the lungs. In the described embodiment, deoxygenation gas tank 501 is external to OCS 100 and maintenance gas tank 221 is located internal to OCS console 100. In an alternative embodiment, OCS console 100 also includes an internal deoxygenation gas tank. In another alternative embodiment, an additional external maintenance gas tank 221 supplements the maintenance gas tank internal to the OCS console. External gas tanks can be supplied at the donor site, recipient site, or can be stowed in a vehicle transporting the lungs. Since external tanks do not need to be accommodated within the confined volume of the OCS lung console 101, they can be larger, and can supplement the limited gas supply of the smaller internal gas tanks of OCS 1000.

Controller 202 manages the release of maintenance and assessment gases by controlling the valves, gas selector switch 216, and ventilator 214, thus implementing the preservation of the lungs in maintenance mode, or the assessment of the lungs in one of the assessment modes. Blood gas solenoid valve 204 controls the amount of gas flowing into blood gas exchanger 402. Airway pressure sensor 206 samples pressure in the airway of lungs 404, as sensed through isolation membrane 408. Relief valve actuator 207 is pneumatically controlled, and controls relief valve 412. The pneumatic control is carried out by inflating or deflating orifice restrictors that block or unblock the air pathway being controlled. This method of control allows complete isolation between the control systems in lung console module 200 and the ventilation gas loop in lung perfusion module 400. Pneumatic control 208 controls relief valve 207 and bellows valve actuator 210. The pneumatic control circuits of lung console module 200 are described in detail below. Trickle valve 212 controls delivery of gas to the airway of lungs 404. Ventilator 214 is a mechanical device with an actuator arm that causes bellows 418 to contract and expand, which causes inhalation and exhalation of gas into and out of lungs 404.

OCS monitor 300 provides user control of OCS 1000 via buttons, and displays data from the system's sensors that indicate the state of the lungs and of the various subsystems within OCS 1000. Monitor 300 is universal, i.e., it can be used for any organ. It includes monitor processor 302 that runs the software controlling monitor 300 and displays data on LCD 304. In the described embodiment, monitor processor 302 is a Freescale MX1. Examples of various screen displays are described below in connection with the usage modes of OCS 1000. OCS monitor 300 includes four control buttons for the user: menu button 306 brings up the configuration menu; alarm button 308 silences the speaker; pump button 310 controls the circulatory pump; and action button 312 provides access to certain organ-specific actions, such as ventilator control, or to system actions, such as saving a session file to an external memory card. Other controls can also be included, such as a knob for controlling a value or selecting an item.

OCS lung console 101 includes probes that measure properties of circulating perfusion medium 250, also referred to herein as perfusion fluid and perfusate. Flow probe 114 measures the rate of flow of perfusion fluid 250 through the system. In the described embodiment, flow probe 114 is placed on the perfusate line as it leads towards the pulmonary artery. Pressure sensor 115 measures pulmonary arterial pressure at the point of entry of perfusion fluid 250 into the lungs. Two oxygen saturation sensors 116 and 118 sense the amount of oxygen in perfusion fluid 250 in the arterial, i.e., oxygenated, side of the circuit and in the venous, i.e., de-oxygenated, side of the circuit.

Lung perfusion module 400 is in direct contact with the gas and fluid circuits flowing through lungs 404. It is therefore necessary to isolate it from the rest of OCS 1000 so that no tissue or fluids that come into contact with the organ ever come into contact with OCS lung console 101. This is achieved by connecting it to the OCS lung console 101 only via one-way gas lines, or via isolated control gas for pneumatic control, or by means of a mechanical actuator (for the bellows). The entire lung perfusion module 400, which contains all of the tissue and blood-contacting surfaces for the whole system, is disposable and is replaced for each new lung that is placed in OCS 1000. All tissue and blood-contacting surfaces are part of disposable lung perfusion module 400, which is manufactured from injection-molded components using inexpensive biocompatible materials that can easily be sterilized. Lung perfusion module 400 is shaped and sized for coupling with OCS console 100. The coupling between lung perfusion module and the OCS console can involve an interlocking mechanism, or other mechanism that secures the perfusion module to the OCS console or otherwise maintains the perfusion module in a desired position relative to the OCS console. In the described embodiment, lung perfusion module is easily attached to and detached from OCS console 100 with a mechanical hinge and clasp mechanism, described below in connection with FIG. 22. It is also connected by plug-in electrical and optical connections.

Lung perfusion module 400 includes bellows 418, which is actuated by ventilator 214. Ventilator 214 uses a mechanical actuator arm to compress and release bellows 418. Compressing the bellows causes gas to be inspired by lungs 404; releasing the bellows causes it to expand and allow gas to be expired by the lungs. The distance traveled by the mechanical actuator in compressing bellows 418 determines the tidal volume, i.e., the volume of gas inhaled by lungs 404. Gas flowing in and out of the lungs passes through gas filter 410, which prevents any fluids produced by the lungs from entering the gas loop.

In order to ensure isolation of the gas in the lung perfusion module 400 ventilation loop, all lung gas connections between lung perfusion module 400 and OCS lung console 101 include membranes that prevent gas from flowing back into OCS lung module 101. Isolation membranes are not needed for pneumatic control gas connections, such as from relief valve actuator 207 and bellows valve actuator, because this gas has no contact with the organ. One-way gas flow valves that only permit flow into the lung perfusion module are automatically isolated from gas in the ventilation loop; such valves include trickle valve 212 and blood gas solenoid valve 204. Airway pressure sensor 206 samples the gas line pressure via isolation membrane 408 that prevents any exchange of gas backwards towards OCS lung console 101.

Perfusion module 400 includes blood gas exchanger 402, which includes a perfusate/gas exchange membrane that enables the infusion of a gas into the perfusate stream. The perfusate circulates through circuits 406 and 407 between lungs 404 and gas exchanger 402. The organ chamber supports lungs 404 and channels the perfusate coming out of the lungs from the left atrium in a manner that facilitates accurate measurement of arterial oxygen content levels. A detailed description of the perfusion circuit and the organ chamber is provided below.

Perfusion module 400 also includes relief valve 412, which provides for controlled release of gas to be expired to the outside, serving to reduce gas pressure within the ventilator gas loop. Bellows valve 414 controls the gas flow to or from the lungs. Check valve 416 is a one-way valve which allows external air to be drawn into the ventilation system. Bellows 418 expands and contracts; when the ventilator system is used in rebreathing mode, the bellows exchanges a substantially fixed volume of gas with the lungs as it expands and contracts.

Figure 2:
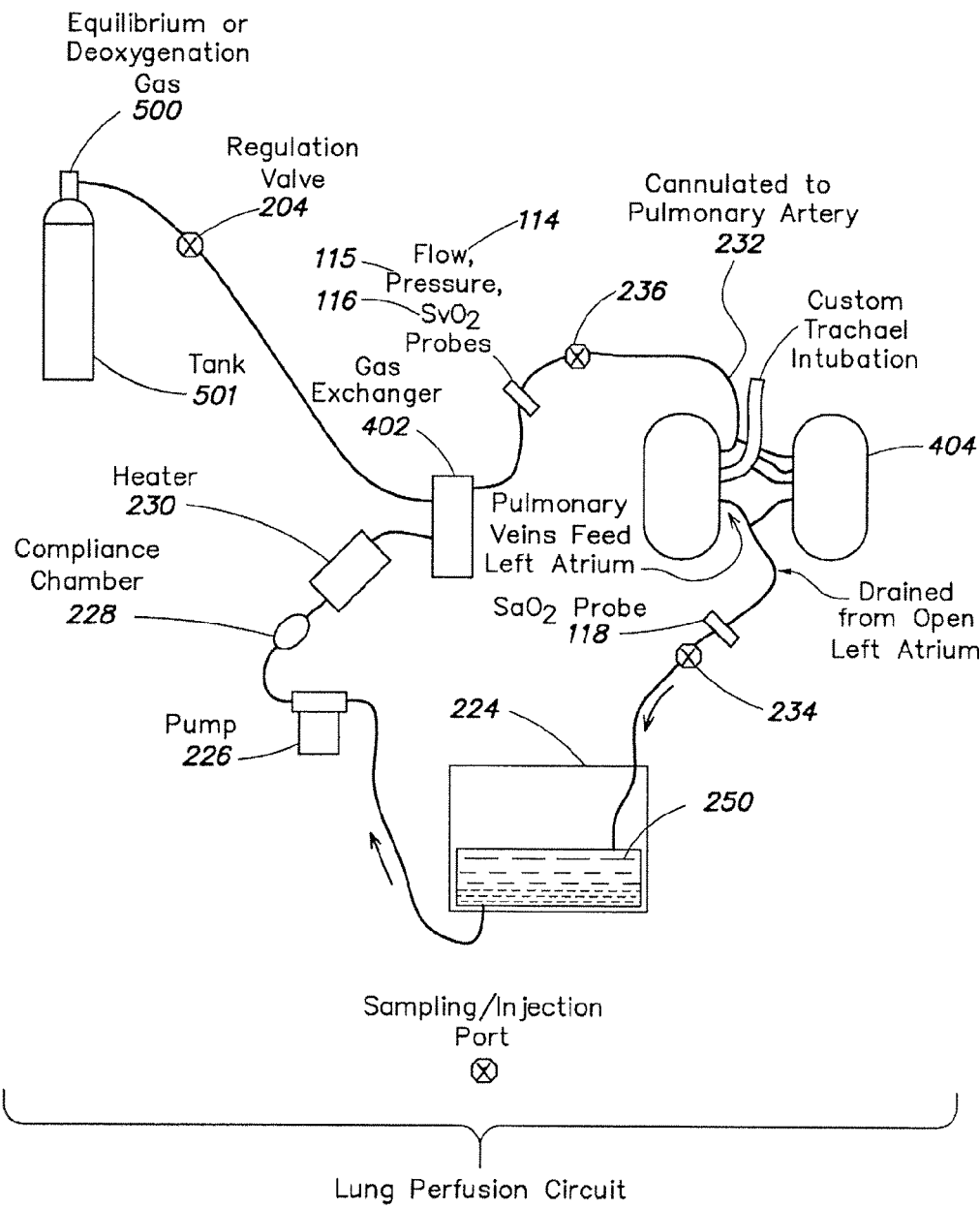
FIG. 2 is a schematic diagram of the lung perfusion circuit of the described embodiment.

FIG. 2 illustrates the lung perfusion circuit. The circuit is housed entirely within the lung perfusion module, and all its components are disposable. Perfusion fluid 250 circulates within the perfusion circuit, passing through various components of lung perfusion module before passing through the vascular system of lungs 404. Pump 226 causes perfusion fluid 250 to flow around the lung perfusion circuit. It receives perfusion fluid 250 from reservoir 224, and pumps the solution through compliance chamber 228 to heater 230. Compliance chamber 228 is a flexible portion of tubing that serves to mitigate the pulsatile nature of pump 226. Heater 230 replaces heat lost by perfusion fluid 250 to the environment during circulation of the fluid. In the described embodiment, the heater maintains perfusion fluid 250 at or near the physiologic temperature of 30-37 degrees C., and preferably at about 34 degrees C. After passing through heater 230, perfusion fluid 250 flows into gas exchanger 402. Like the lung, gas exchanger 402 enables gases to be exchanged between gas and perfusion fluid 250 via a gas-permeable, hollow fiber membrane. However, the gas exchanger has an effective gas exchange surface area of about 1 square meter, which is only a fraction of the 50-100 square meter effective exchange area of the lungs. Thus gas exchanger 402 has only a limited gas exchange capability compared to the lungs. Blood gas solenoid valve 204 regulates the supply of gas into gas exchanger 402. The composition of gas supplied to gas exchanger is determined by which mode the OCS is in, described in detail below. For example, when OCS 1000 is in sequential assessment mode, deoxygenation gas 500 is supplied to the gas exchanger during the deoxygenation phase of the sequential assessment cycle. After passing through gas exchanger 402, perfusion fluid 250 passes through flow rate probe 114, pressure probe 115, and a perfusate oxygen probe 116. We refer to the readings from oxygen probe 116 as $SvO_2$ since it measures oxygen in perfusion fluid 250 just before it enters the lungs, which is analogous to venous blood oxygen. Sampling/injection port 236 facilitates the removal of a sample or the injection of a chemical just before perfusion fluid 250 reaches the lungs. Perfusion solution then enters lungs 404 through cannulated pulmonary artery 232.

Figure 8:
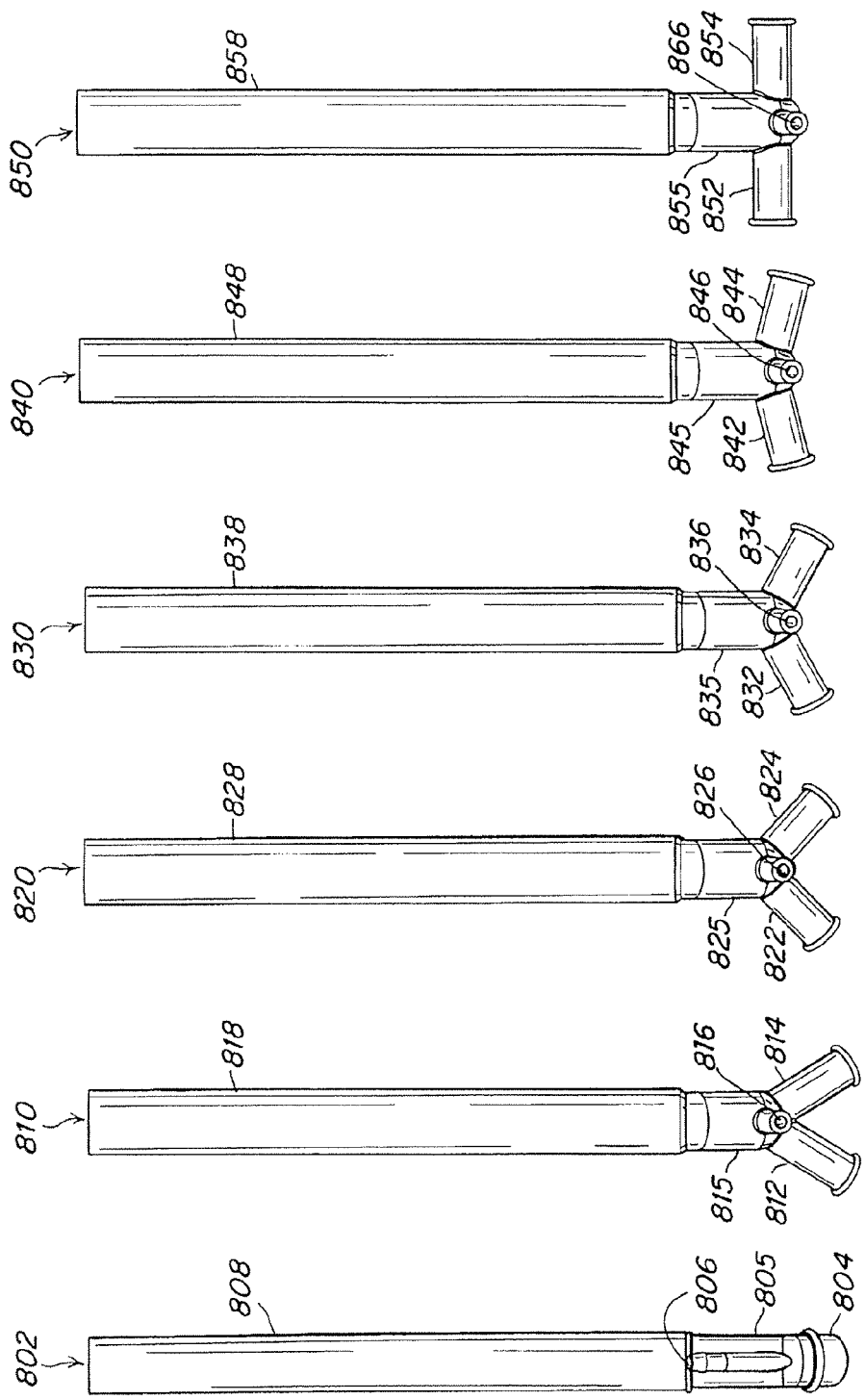
FIGS. 8A-8F show examples of pulmonary artery cannulae, according to the described embodiment.
Figure 9:
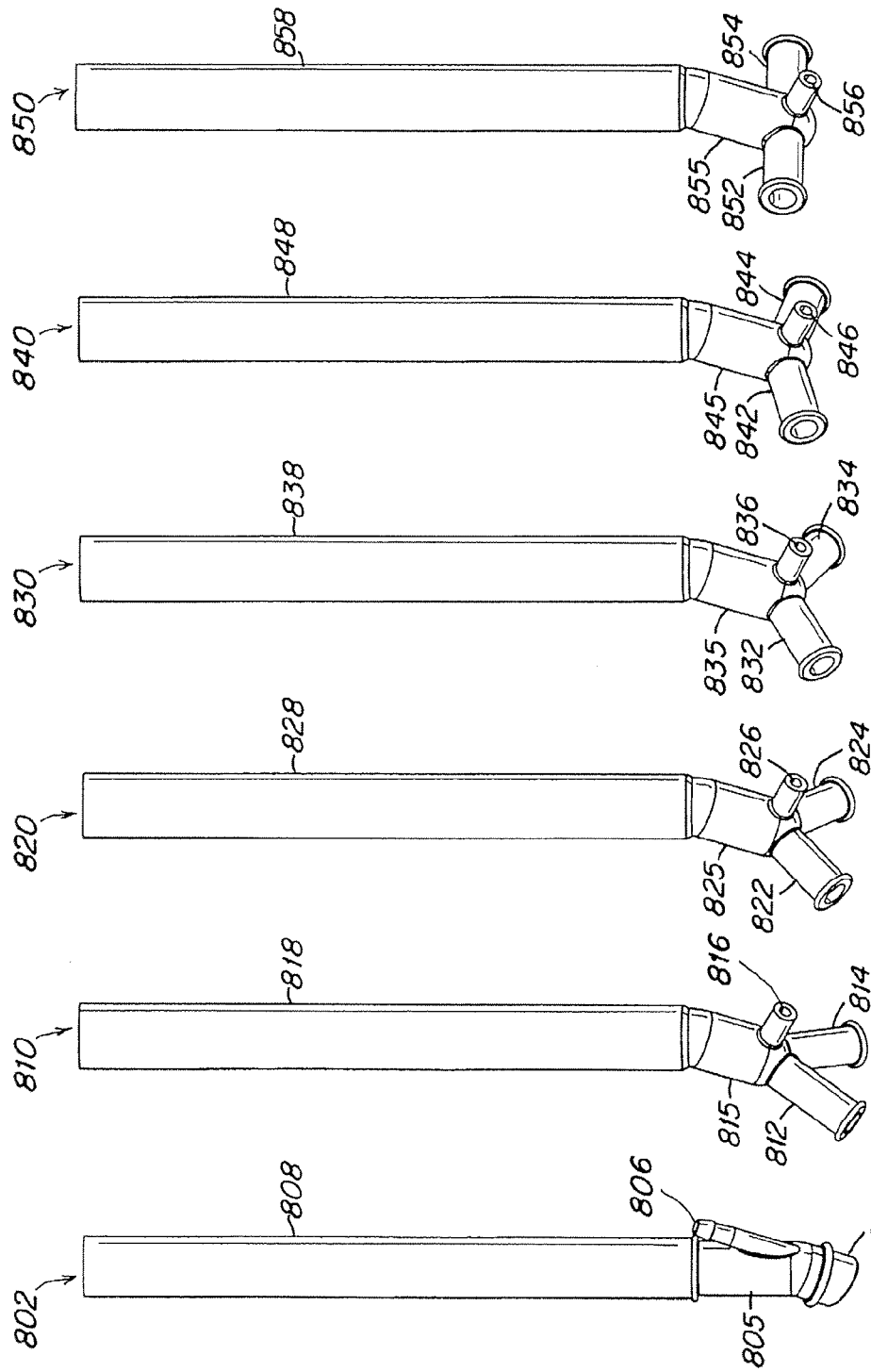
FIGS. 9A-9F show lateral views of the pulmonary artery cannulae illustrated in FIGS. 8A-8F.

The pulmonary artery (PA) cannula connects the perfusion circuit with the vascular system of lungs 404. Several exemplary embodiments of a pulmonary artery (PA) cannula are shown in FIGS. 8A-8F. Referring to FIG. 8A, single PA cannula 802 has single insertion tube 804 for insertion into a single PA, and is used to cannulate the PA at a point before it branches to the two lungs. To connect the cannula to the pulmonary artery, insertion tube 804 is inserted into the PA, and the PA is secured onto the tube with sutures. Insertion tube 804 of cannula 802 connects to connector portion 805, which serves to position insertion tube 804 at an angle and location suitable for strain-free connection to the pulmonary artery of lungs 404. Connection portion 805 connects to main tube portion 808, which is attached to the perfusion fluid circuit. FIGS. 9A is a lateral view of PA cannulae 802 showing the angle between insertion tube 804 and connecting portion 805; in the described embodiment, the angle is between about 15 degrees and 30 degrees, and preferably about 22.5 degrees.

Referring to FIGS. 8B-8F, double PA cannulae 810, 820, 830, 840, and 850 each have two insertion tubes 812, 814, 822, 824, 832, 834, 842, 844, and 852, 854, each pair of tubes being angled apart from the main axis of the cannula by 30, 45, 60, 75, and 90 degrees in cannulae 810, 820, 830, 840, and 850 respectively. Each tube has a diameter of about 0.5 to 0.72 inches at the rib, and about 0.4 to 0.62 inches on the body of the insertion tube. The varying angles provide the surgeon with a choice of cannulae to best accommodate the anatomy of the donor lungs. Referring to FIGS. 8B, pair of insertion tubes 812 and 814 are joined to connecting portion 815 in a Y-shaped configuration. As shown most clearly in FIG. 9B, connecting portion 815 is angled with respect to main tube 818; the angle is chosen to facilitate the insertion of insertion tubes 812 and 814 into the pulmonary arteries of lungs 404. In the described embodiment the angle is between 15 and 30 degrees, and preferably about 22.5 degrees. Referring to FIGS. 9C-9F, a similar angle of between 15 and 30 degrees, and preferably about 22.5 degrees, is shown between connecting portions 825, 835, 845, 855 and their corresponding main tubes 828, 838, 848, and 858. An alternative to having PA cannulae with branching ends angled apart at various preset angles, is to have malleable PA cannulae that can be bent to accommodate the angle of a donor's lung vessels.

The material of manufacture of the PA cannulae is now described. In an illustrative embodiment of single PA cannula 802, insertion portion 804 has a polycarbonate tip, with connector portion 805 and main tube portion 808 being made of urethane tubing. In an alternative embodiment, insertion tube 804, connector portion 805, and main tube portion 808 are all made of a single piece of silicone of between 50 Shore A to 90 Shore A hardness silicone, preferably of a 80 Shore A hardness silicone. Similarly, for dual PA cannulae, main tubes 818, 828, 838, 848, 858 and connector portions 815, 825, 835, 845, 855 of double PA cannulae 810, 820, 830, 840, and 850 respectively may be made of urethane, and the insertion tubes 812, 814, 822, 824, 832, 834, 842, 844, 852, and 854 may be made of polycarbonate. In an alternative embodiment, the entire dual tube PA cannula, i.e., the dual insertion tubes, connector portion, and main tube, are all made of a single piece of 80 Shore A silicone. An advantage of silicone construction is that it is soft enough to provide a good purchase and grip for lung vessels tied on to the cannula connector with sutures. In addition, silicone can readily be cut to the required length at the time of attachment to the lung PA. Furthermore, silicone allows fabrication of the entire cannula in a single piece because it can be molded into a complex shape. Integral construction of the cannula eliminates transitions between separate cannula parts, which can produce unwanted turbulence in perfusion fluid 250, introduce impurities, or cause leaks at the joints between separate parts. In addition, integral construction requires the molding of a single piece only, which reduces cost and increases the reliability of the cannula.

The connecting portion of each PA cannula also includes a connector for connecting perfusate pressure transducer 115. Referring again to FIGS. 8A-8F and 9A-9F, PA cannulae 802, 810, 820, 830, 840, and 850 include pressure transducer connectors 806, 816, 826, 836, 846, and 856 respectively. The connector serves to allow placement of the perfusate pressure sensor at the correct location, right at the point of entry to the lungs where the perfusate flow slows, and pressure readings are not distorted by Bernoulli flow pressure. The pressure transducer connectors also provides a channel for pressure sensor 115 to be remotely vented, helping to ensure the accuracy of the pressure reading.

After passing through the lungs, the perfusate exits the lungs from the left atrium, a portion of which is removed along with the lung during explantation of the lungs from the donor. Since the left atrial tissue serves as an attachment zone during transplantation of the lungs into the recipient, it is important to leave it as undisturbed and healthy as possible. Therefore, in the described embodiment, the left atrial cuff is not cannulated, allowing the circulating perfusate to drain from the open left atrium and the left atrial cuff.

Figure 10:
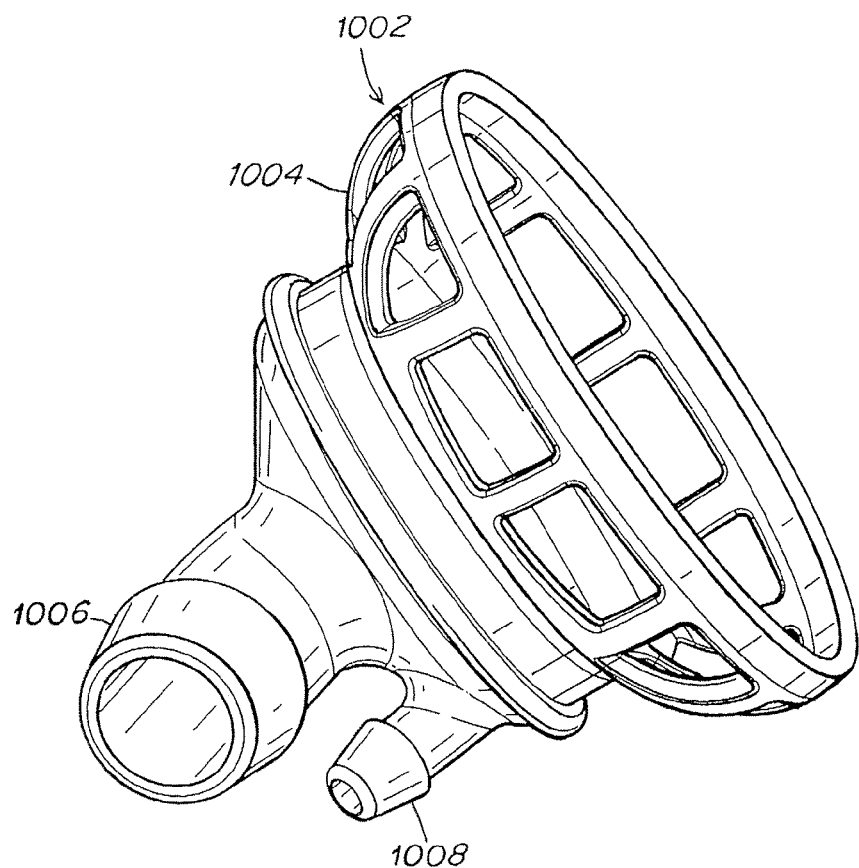
FIG. 10 is an illustration of a left atrium cannula.

In an alternate embodiment, the left atrial cuff is cannulated with cage-like cannula 1002, illustrated in FIG. 10. In this embodiment, all the LA vessels are placed inside the cannula; the excess LA tissue is then wrapped around the cannula. The cage-like structure 1004 of LA cannula 1002 is designed to hold the left atrium open without occluding any pulmonary veins, thus helping to reduce the risk of compromising the health of the tissue. Inside the cannula, the perfusate flowing from the pulmonary veins is collected into tube 1006, and fed to the perfusate reservoir. Connector 1008 provides a connection point for a pressure transducer, which can be placed inside cannula 1002 and measure perfusate pressure.

The perfusate exiting the lungs is collected in a dual drain system, using an "over flowing cup" technique to allow the sampling of newly drained fluid before it becomes mixed with other perfusate in the reservoir. All the flow from the lungs is directed to a small cup which feeds a measurement drain. The capacity of this drain is restricted by the use of small diameter tubing. Perfusate from the lungs exits at a flow rate that exceeds the capacity of the measurement drain. Excess blood overflows this small cup and is directed to the main drain and thus to the reservoir pool. The measurement drain directs a bubble free stream of newly drained perfusate toward the second oxygen probe 118 to obtain an accurate reading of arterial oxygen level, referred to as SaO2. After passing through second sampling/injection port 234, the perfusion solution completes its cycle and returns to reservoir 224. The dual drain system is necessary only in the configuration in which the left atrial cuff is uncannulated. But if the left atrial cuff is cannulated, such as with a cage cannula as described below, there is no need for the dual drain system since a solid column of newly drained, bubble-free perfusate exits the cannulated left atrial cuff.

In the described embodiment, perfusion fluid 250 is composed of donor blood with the addition of heparin, insulin, vitamins, and antibiotics. Dextran serves to adjust oncotic pressure, Hematocrit levels, and pH.

The following sections describe how OCS 1000 is used to preserve and assess a lung. The preinstrumentation section describes the initial steps in preparing OCS 1000 and the lung prior to connecting the lung to the OCS. The maintenance mode section describes how the OCS is used to preserve the lung. The assessment mode sections describe two ways of assessing the condition of the lungs—continuous mode and sequential mode.

Preinstrumentation

Figure 7:
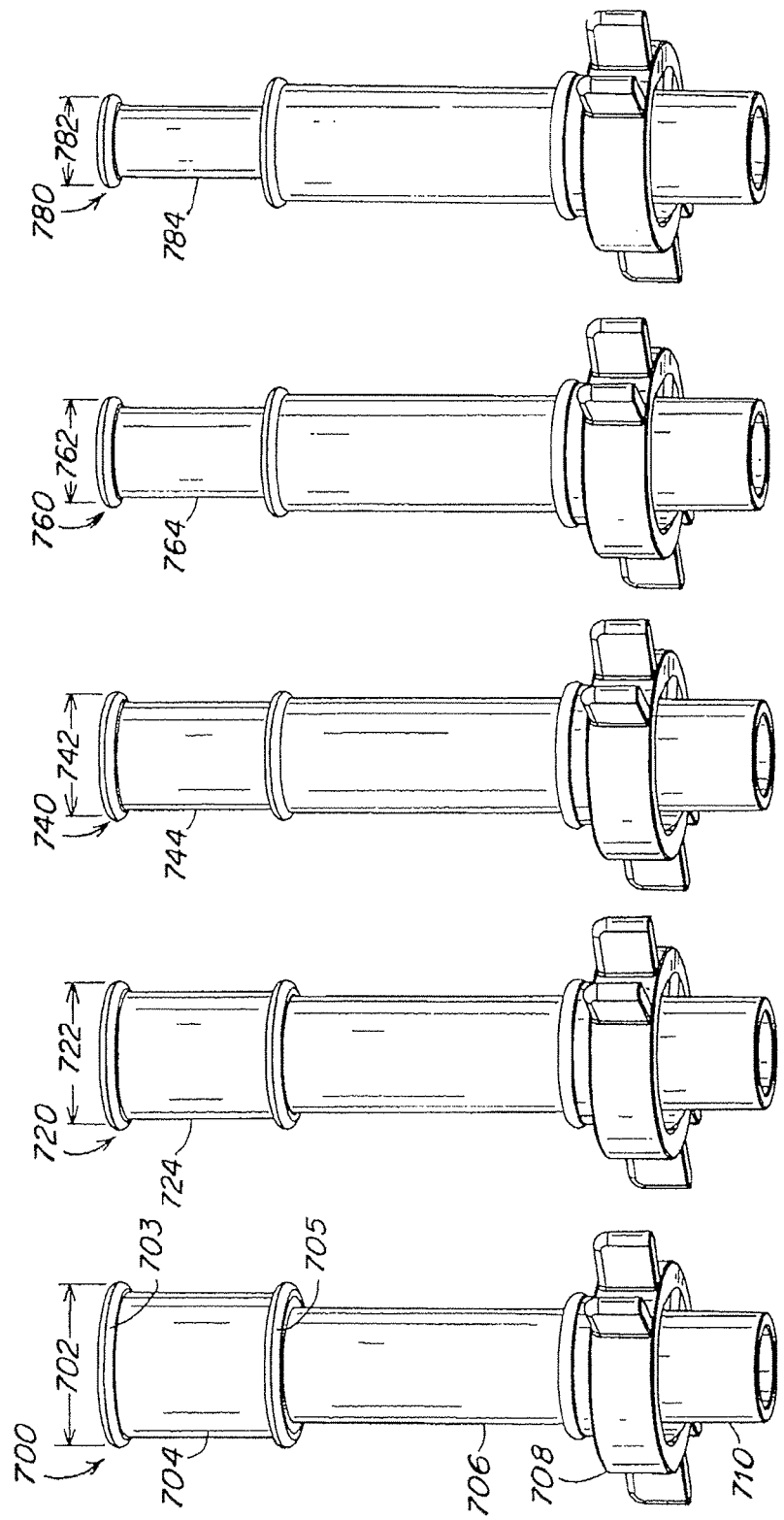
FIGS. 7A-7E show examples of tracheal cannulae, according to the described embodiment.

After removing the lung from the donor, the tracheal cannula is inserted into the trachea to provide a means of connection between the lung perfusion module 400 gas circuit and the lungs. FIGS. 7A-7E illustrate a set of exemplary tracheal cannulae. With reference to FIG. 7A, cannula 700 includes tracheal insertion portion 704 to which the trachea is secured with a cable tie, or by other means. In the described embodiment, insertion portion 704 is about 0.8 inches long. The base of cannula 700 is preferably composed of polycarbonate, or another hard injection-moldable, biocompatible plastic, such as acrylic, polyester, K-resin, nylon, polyethylene, or polypropylene. The over-layer over insertion portion 704 is preferably composed of a soft silicone rubber; alternative materials for the over-layer are other soft, biocompatible extruded or moldable materials such as polyurethane, thermoplastic elastomers, and other rubber materials. Adjacent to tracheal attachment portion 704 is flexible section 706, which is preferably composed of polyurethane, or one of the other biocompatible materials listed above as being suitable for the insertion portion over-layer. Insertion portion 704 and its over-layer, and flexible portion 706 are injection moldable, with the silicone over-layer being over-molded onto the base part. In an alternative embodiment, the silicone over-layer is separately molded, or extruded and stretched over the base.

At the end of insertion portion 704 that is inserted into the trachea is rib 703; the rib helps secure insertion portion 704 at the inserted location within the trachea, and is secured with a cable tie placed around the trachea. At the opposite end of insertion portion 704, second rib 705, having a diameter about 0.2 inches greater than the base part diameter of insertion portion 704, acts as a stop for the silicone over-layer and as a stop for the trachea. Past rib 705 is a tubing barb fitting that is about 0.5 inches long, and has an angled barb to hold a 0.5 inch diameter tube. On the base piece that goes to lung OCS lung chamber connector 710, there is a second tubing barb fitting that is about 0.5 inches long, having an angled barb to hold a 0.5 inch diameter tube.

Flexible portion 706 can be clamped to seal off air flow in and out of lungs 404. For example, clamping of section 706 is used to maintain a static inflation of lungs 404 after explantation and before connections to the gas circuit of the OCS. Static inflation serves to prevent collapse of the lungs, and the consequent damage to the alveoli. In static inflation, the lungs are inflated to a pressure of about 20 centimeters of water. The tracheal cannula is then clamped off at flexible section 706.

Near the end of flexible section 706 furthest from the tracheal insertion portion, cannula 700 includes locknut 708 for securing the cannula to the lung chamber. Locknut 708 is mounted on a stepped portion of the cannula tube. Adjacent to locknut 708, 0.7 inch-long 15 mm. connector 710, serves to connect the cannula to a standard ventilator connector, which connects the lung to the gas circuit of the OCS. Tracheal cannulae are designed to accommodate donor lungs having varying tracheal diameters according to the size of the donor. FIG. 7A illustrates tracheal cannula 700 having insertion portion tip diameter 702 of 0.9 inches. In FIGS. 7B, 7C, 7D, and 7E, cannulae having insertion portion tip diameters 722, 742, 762, 782 of 0.85, 0.80, 0.75, and 0.70 inches of insertion portions 724, 744, 764, and 784 respectively are shown. Cannulae having insertion portion diameters smaller than 0.7 inches, or larger than 0.9 inches may be needed to accommodate lungs from certain donors.

Before receiving the lungs, the OCS perfusion circuit is primed with donor blood, priming solution, and drugs. This perfusate is then circulated and warmed. During this phase, gas exchanger 402 establishes blood gases that correspond to maintenance mode. This is achieved by setting gas selector switch 216 to allow maintenance gas to flow into the gas exchanger, and by duty cycle modulating gas exchanger valve 204 to provide a low average flow of maintenance gas through the gas exchanger. The exchange of gases in the gas exchanger causes the circulating perfusate to reach equilibrium with the maintenance gas, establishing the desired maintenance perfusate gas levels of $O_2$ and $CO_2$. The perfusate pH is controlled by the $CO_2$ level. These preparatory steps ensure that when the lung is instrumented on the OCS, the perfusate has already reached the maintenance gas levels, which helps accelerate the lungs' transition to maintenance mode.

Maintenance Mode

Maintenance mode places the lungs in a safe, stable condition so as to allow them to be preserved for an extended period of time. By placing the lungs in equilibrium with a gas containing oxygen to meet the lung's metabolic demands and carbon dioxide to control blood pH, the maintenance gas satisfies the lung's cellular requirements. Oxygen consumption in the lung is so low that each breath can be substantially recycled, dramatically reducing the volume of fresh gas consumption. Since it is normally necessary to transport donated organs to a different site where the recipient is located, reducing the amount of gas needed to support the lungs, and thereby increasing the portability of the system, is a significant benefit.

When the lungs are placed within the organ chamber, the tracheal cannula is connected to the system gas line, which is placed in pause mode. In pause mode, bellows 418 are in a fully expanded state, i.e., prepared to perform the first lung inhalation. The clamp on the tracheal cannula is removed, and the pressures in the lung and in the gas line equalize. Inhalation then commences.

Figure 3:
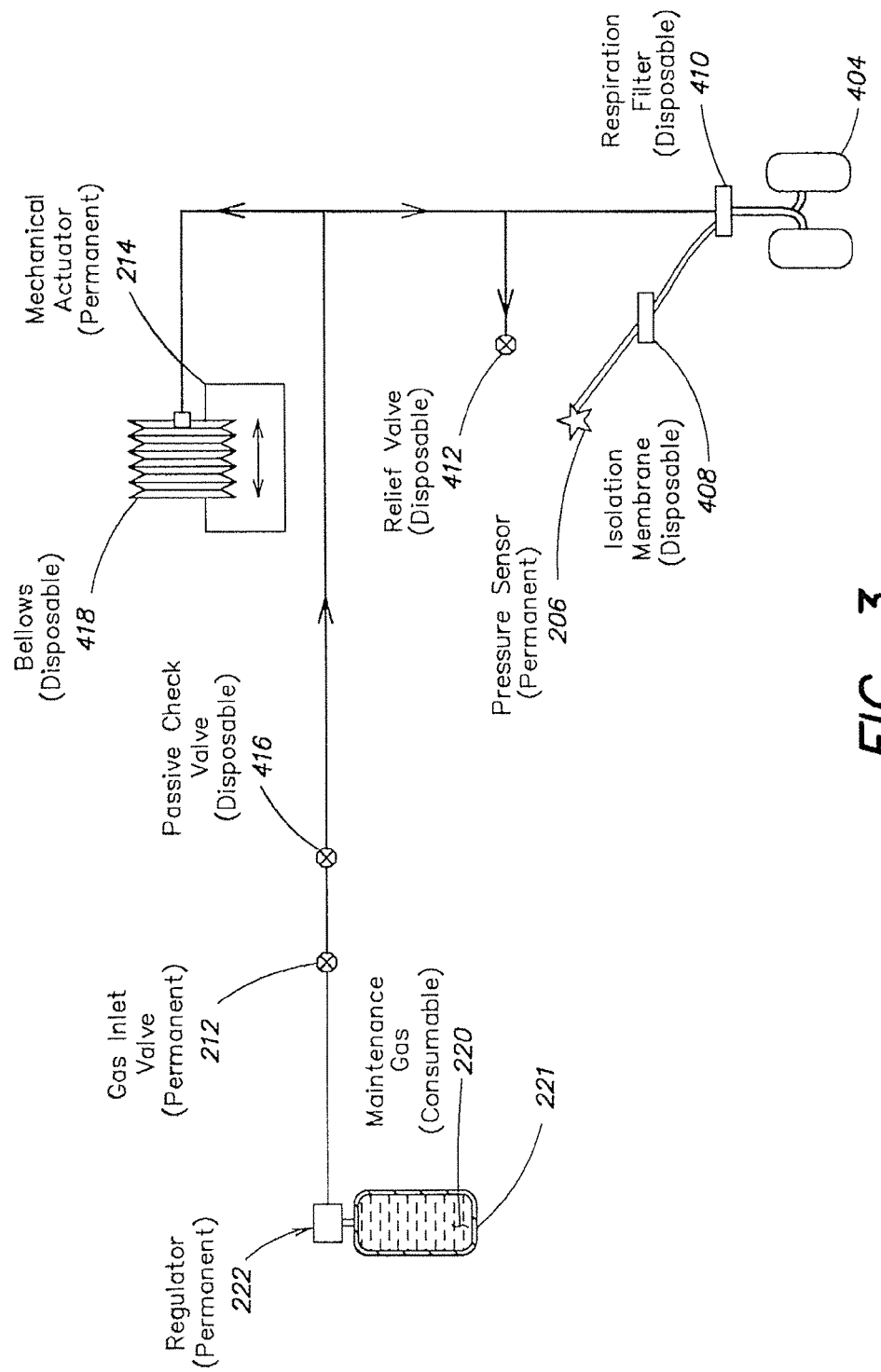
FIG. 3 is a schematic diagram of the gas loop of the organ care system in maintenance mode, according to the described embodiment.

FIG. 3 is an illustration of the functioning of the OCS in maintenance mode. In maintenance mode the ventilator system moves a captive volume of gas back and forth between the lungs and the bellows, causing the lungs to rebreath the gas. In addition, a small amount of maintenance gas 220 is trickled into the ventilation circuit during each breath through valve 212. Excess gas is exhausted from the circuit through relief valve 412 in order to prevent pressure buildup and maintain the desired minimum gas pressure in the system. In the described embodiment, maintenance gas 220 is composed of about 9-15% oxygen, and preferably about 12% oxygen, about 4-7% carbon dioxide, and preferably about 5.5% carbon dioxide, with the balance being nitrogen.

The composition of maintenance gas 220 includes an amount of oxygen that is about one half that of air, and an amount of carbon dioxide that maintains a near-physiologic pH level in perfusion fluid 250. In maintenance mode, an equilibrium is achieved between maintenance gas 220 and perfusate gas levels. In this equilibrium, there is only a small difference between the oxygen level in perfusion fluid 250 entering lungs 404, i.e., the venous level $PvO_2$, and the level exiting lungs 404, i.e., the arterial level $PaO_2$. The composition of maintenance gas 220 is chosen to achieve perfusate oxygen levels that depart as little as possible from physiologic blood gas levels. Too high an oxygen content results in a venous oxygen level that is well above physiologic levels; conversely, too low an oxygen level results in an arterial oxygen level that is well below physiological levels. The preferred maintenance gas composition is a compromise between these levels, achieving equilibrium arterial and venous oxygen levels in perfusion fluid 250 that are approximately mid-way between physiologic venous and arterial levels. The preferred oxygen component of about 12% also provides more than sufficient oxygen to serve the lungs' metabolic needs. Furthermore, a 12% oxygen level is close to the oxygen level in the alveoli of a healthy lung breathing air, because there is a gradient between the oxygen level in the trachea and the level in the alveoli caused by gas exchange along the airway path into the lungs. This gradient is absent in the case of lungs 404 in maintenance mode, when maintenance gas is being rebreathed, and the oxygen level is about 12% throughout the lung.

Initially, when the lungs are first connected to the OCS gas line, the gas loop is filled with air, not with maintenance gas. Thus, ventilation of the lungs is initially with air. As the maintenance gas is trickled in, and excess gas is released, the composition of gas in the gas loop soon changes to that of the maintenance gas.

In maintenance mode, gas selector valve 216 (FIG. 1) is set to select maintenance gas tank 221. Gas exchanger valve 204 is always closed in maintenance mode because gas exchanger 402 is not used. Bellows valve 414 is always open to maintain the exchange of gas between the bellows and the lungs. Referring to FIG. 3, passive check valve 416 allows air into the circuit under suction conditions, but remains closed during maintenance mode because the ventilation circuit always has positive pressure.

At the start of each maintenance mode cycle, bellows 418 are at the fully open position and the lungs are at their minimum volume. During the cycle, bellows 418 compresses, driving gas into the lungs. The lungs expand to accommodate this gas volume, causing a rise in pressure. When the specified volume of gas has been delivered, bellows 418 pauses for a specified plateau time before starting the exhalation portion of the cycle. During exhalation, bellows 418 returns to its original fully expanded state, and the lungs relax. The next ventilation cycle begins after an interval set by the specified respiration rate. The extent to which bellows 418 compress during the inhalation phase of each cycle is determined by the user-specified tidal volume, typically between 400 and 1200 mL.

Figure 6:
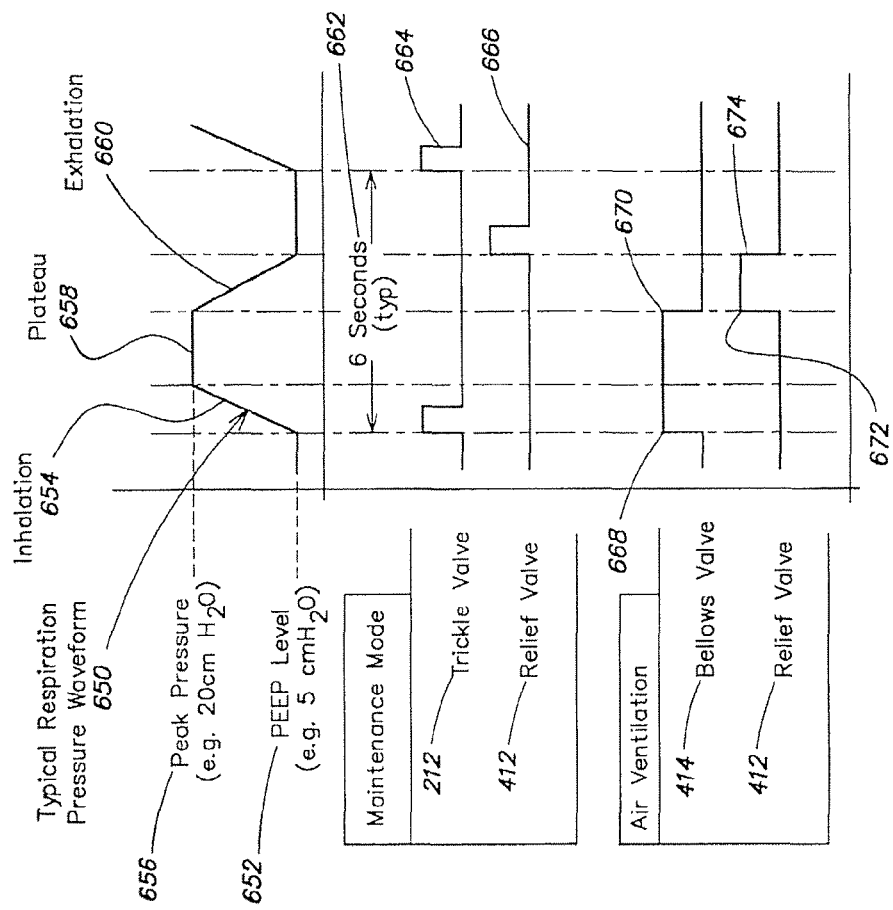
FIG. 6 is a diagram showing a typical pressure waveform in the lung over a breathing cycle, according to the described embodiment.

FIG. 6 shows typical respiration pressure waveform 650 for each ventilation cycle. At the start of the cycle, the pressure is set to positive end expiratory pressure (PEEP) value 652, which is approximately 5 cm of $H_2O$. As the bellows compress in inhalation portion 654 of the cycle, the pressure increases to peak pressure 656, and remains at the peak pressure for plateau portion 658 of the cycle. In the described embodiment, the peak pressure is about 20 cm $H_2O$. In exhalation portion 660 of the cycle, the pressure decreases until it reaches the desired PEEP level at the end of the cycle. Duration 662 of a complete ventilation cycle is set by the user-selected respiration rate, and is typically about 6 seconds.

Two other events occur in each maintenance mode ventilation cycle. During inhalation phase 654, trickle valve 212 opens briefly allowing a specific volume of calibrated maintenance gas into the circuit. Later, at the end of exhalation phase 660, relief valve 412 opens briefly to exhaust excess gas to the outside air until the desired PEEP is reached. The opening of trickle valve 212 and relief valve 412 are illustrated in FIG. 6 by traces 664 and 666 respectively.

The average flow of maintenance gas into the ventilation loop is specified by the user, and is typically 500 ml/min. At a ventilation rate of 10 breaths per minute, trickle valve 212 allows 50 ml of maintenance gas into the circuit on each cycle. When ventilating with a typical tidal volume of 600 ml, the injection of maintenance gas on each cycle amounts to only about 10% of the tidal volume, and thus has only a small effect on any given ventilation cycle. The flow rate of maintenance gas is usually set at the minimum level required to keep the gas composition in the gas loop close to the maintenance gas levels despite the tendency of the lungs' metabolism to decrease the oxygen level and increase the $CO_2$ level. Injection of maintenance gas is also used to maintain the desired PEEP level in the system. The amount of gas leakage from the lungs and from respiration fittings also affects the amount of maintenance gas injected.

Since the metabolic activity of the lung is low, it requires little oxygen for support, and produces only a small amount of carbon dioxide. Thus the lung's own metabolism has only a small effect on the composition of the ventilation gas and perfusate gases. Since maintenance gas is injected into the gas line during each ventilation cycle, the composition of ventilation gas and of the perfusate gases rapidly reach the same composition, namely that of the maintenance gas. Once this situation occurs, the lungs are in a state of equilibrium with the maintenance gas. In the equilibrium state, the perfusate oxygen levels achieve steady state values. The $SaO_2$ steady state level is in the range of about 93-95%, a little lower than the physiologic levels. The corresponding steady state $SvO_2$ level is in the range of about 90-91%, which is higher than physiologic levels. Thus in maintenance mode, the difference between saturation levels in perfusion fluid 250 across the lungs is lower than the physiologic difference. The higher $SvO_2$ results, in part, from the absence of the deoxygenating effect of the body tissue, which is present in the physiologic case. The lower $SaO_2$ level is caused in part by ventilation of the lungs with maintenance gas, which has only about half the oxygen content of air.

In a refinement of maintenance mode ventilation, the system shortens the bellows compression stroke to account for the volume of gas contributed by trickle valve 212, so as to maintain an accurate and constant tidal volume delivery to the lungs.

Assessment Mode—Continuous

Figure 4:
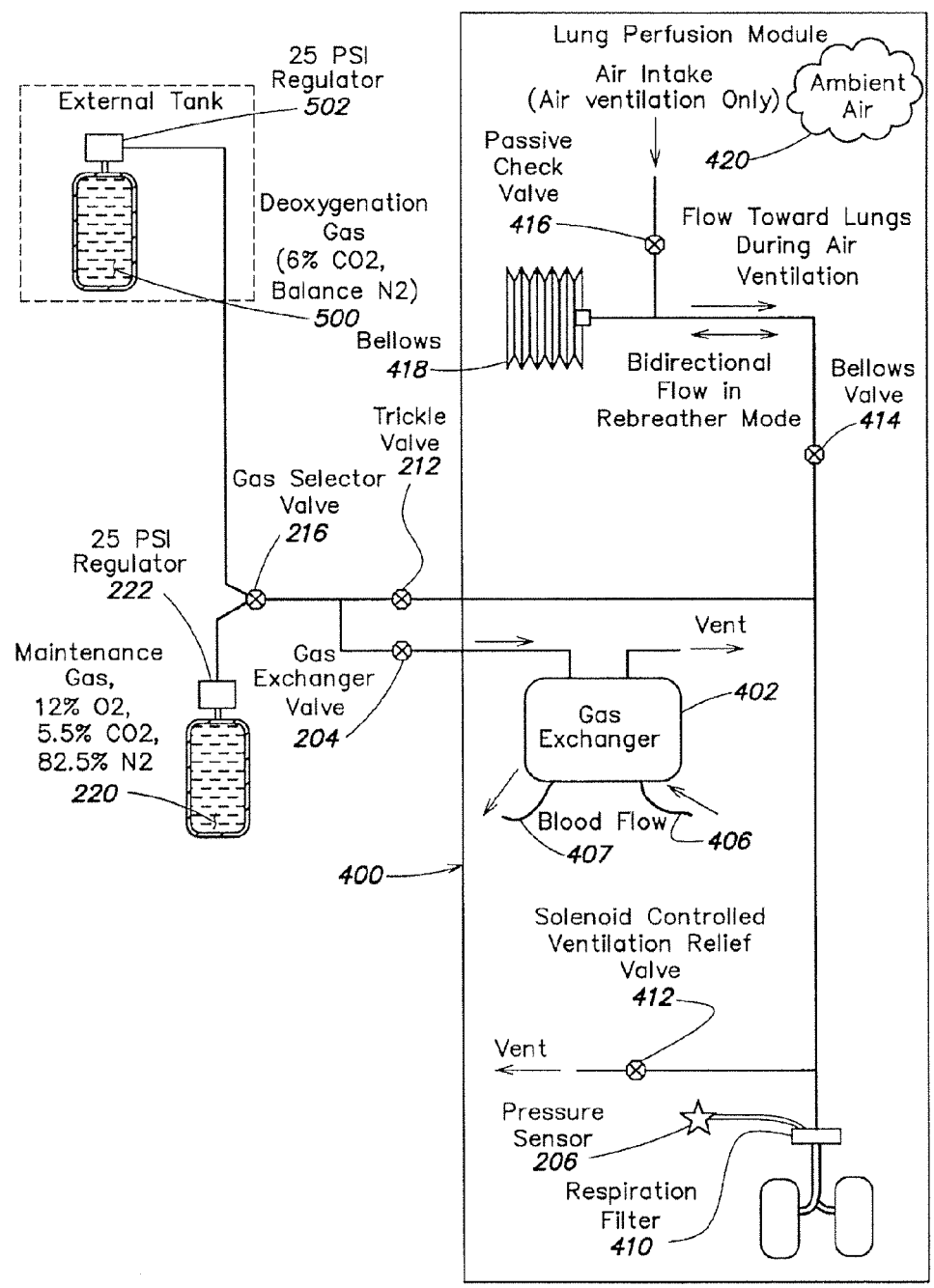
FIG. 4 is a schematic diagram of the gas loop of the organ care system in assessment mode, according to the described embodiment.

FIG. 4 is a schematic diagram showing the various components involved in performing lung assessments. In continuous mode assessment, the system mimics body processes by inhaling air into the lungs, and then removing the perfusate oxygen before the perfusion fluid returns to the lungs. In the body the removal of the oxygen is accomplished by tissues; in the OCS it is accomplished by deoxygenation gas flowing through the gas exchanger. Continuous mode assessment tests the gas exchange capability of the lungs by measuring how well the lungs can reoxygenate the blood. This measurement is performed by measuring venous and arterial blood oxygen levels. The scoring of lung performance in continuous assessment mode is discussed further below.

Figure 34:
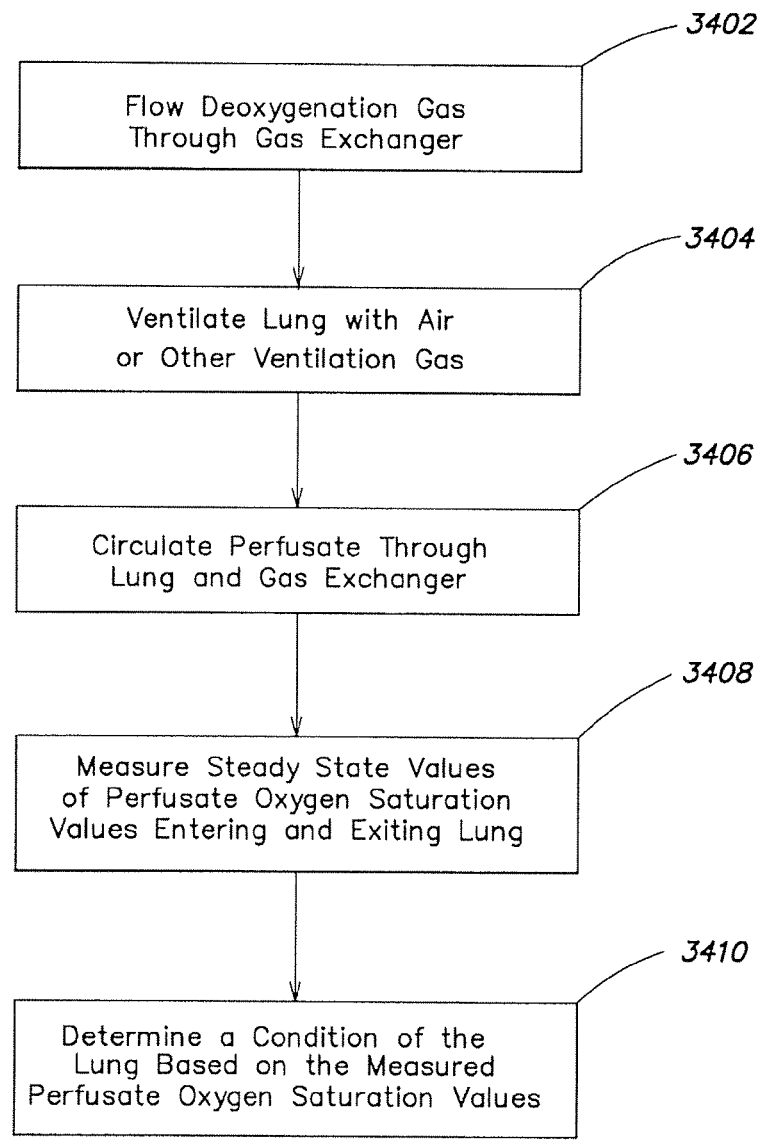
FIG. 34 is a flow diagram showing steps performed during continuous assessment of lungs ex vivo.

FIG. 34 is a flow diagram showing the principal steps involved in performing continuous assessment of the lungs. In step 3402, deoxygenation gas is flowed through gas exchanger 402. This is accomplished using gas selector switch 216, which is set to select deoxygenation gas 500, and by opening gas exchanger valve 204 to connect gas exchanger 402 to the deoxygenation gas supply. In the described embodiment, deoxygenation gas is composed of 4-7% $CO_2$ and preferably 6% $CO_2$, with the balance being nitrogen. Trickle valve 212 is kept closed in this mode. In step 3404, the lungs are ventilated with air or another ventilation gas using bellows 418, which deliver a fresh breath of air or other ventilation gas to the lungs during the inhalation phase of each cycle.

FIG. 6 shows the gas pressure profile and valve settings in a continuous mode ventilation cycle. When a cycle begins, bellows 418 are at the fully open position, the lungs are at their minimum volume, and the pressure is at PEEP level 652. Bellows valve 414 is opened 668 and the bellows compress, driving gas into the lungs in inhalation phase 654. The lungs expand to accommodate the gas, and there is an accompanying rise in pressure. When bellows 418 has delivered the specified volume of gas, the system pauses for a user-specified plateau time 658 (also referred to as dwell time), before starting exhalation phase 660 of the cycle. During the exhalation the connection between the bellows and the lungs is sealed off by closing bellows valve 414, 670. On the lung side of the circuit, relief valve 412 is opened 672 to exhaust gas from the lungs until the PEEP level is reached, at which point relief valve 412 closes 674. In the meantime, bellows 418 is expanded to the fully extended position. This creates suction on the bellows side, which is relieved by passive check valve 416 that lets in external air to fill the bellows in preparation for the next inhalation cycle. The next ventilation cycle begins at a time determined by the user-specified respiration rate. Thus, the coordinated actuation of bellows valve 414 and relief valve 412 during each cycle causes continuous ventilation of the lungs with fresh air.

In an alternative embodiment, bellows valve 414 is closed at the end of inhalation phase 654, before plateau 658. This allows bellows expansion to begin immediately after the inhalation phase.

A gas other than air can be supplied to the inlet of check valve 416. Indeed, gas of any desired composition can be provided. For example, the gas can be provided from common gas entrainment devices that provide oxygen enrichment in a hospital. Such devices can supply ventilation gas at standard 50% or 100% oxygen levels.

While deoxygenation gas is flowing through gas exchanger 402 and the lung is being ventilated with air, perfusate is circulated through the lung and gas exchanger, as shown in FIG. 34, step 3406. In order to approximate to physiologic conditions while assessing the lung in continuous mode, it is desirable to supply the lung with venous perfusion fluid having oxygen levels similar to those of the body. Gas exchanger 402 has a limited gas exchange capability, and at the physiologic blood flow rate of 3-4 l/min., it is not able to remove enough oxygen from the blood to reduce the saturation levels to levels corresponding to the body while the blood is being circulated through the lungs where is continually being reoxygenated. Therefore, to allow gas exchanger 402 to achieve physiologic levels of oxygen in the venous blood, the flow rate is reduced to about 1.5 l/min. In an alternative embodiment, a flow rate intermediate between 1.5 l/min. and physiologic flow rates of 3-4 l/min. are used, with correspondingly higher oxygen levels for the venous blood entering the lungs. In the described embodiment, there is a trade-off between approximating physiologic blood gas levels as the blood enters the lung on the one hand, and physiologic flow rates on the other. The trade-off may be reduced or eliminated by increasing the gas exchange capability of the system. In one approach, multiple gas exchangers are used in series or in parallel in the lung perfusion circuit. In another approach, the gas exchanger's gas exchange capability is increased by equipping it with a larger gas exchange surface.

Continuous mode assessment is typically performed directly after the lungs have been kept in maintenance mode. The following alternate embodiment expedites the switchover from maintenance to continuous mode assessment. Initially, in maintenance mode, bellows 418 contain a full volume of maintenance gas, which would normally be flushed out during several air ventilation cycles. Instead, a purge maneuver is performed to replace the entire contents of the bellows 418 with air. During the purge, bellows valve 414 is open, and bellows 418 are fully compressed at a slow rate. During this compression, relief valve 412 is actively controlled to maintain the pressure near the PEEP level. At the end of this compression cycle, bellows valve 414 is closed, and bellows 418 is fully expanded, filling its entire volume with fresh air from check valve 416. One or more purge cycles may be performed to thoroughly establish the new gas composition.

Once the system is in steady state, the values of the perfusate oxygen levels entering the lung and exiting the lung are measured, as indicated in FIG. 34, step 3408. Perfusate samples can also be taken to confirm levels of oxygen and determine other components of the perfusion fluid. In continuous assessment mode, the user assesses the gas exchange capability of a lung by determining how much oxygen the lung can transfer to the perfusate in each breath. This assessment is based on the measured values of the oxygen levels in the perfusate entering the lung, and leaving the lung (3410). The assessment is calibrated using various parameters, such as the fraction of oxygen in the gas that is ventilating the lung. The standard measure of gas exchange capability is the ratio between the partial pressure of oxygen in the blood in mm. of mercury, $PaO_2$, and the fractional inspired oxygen value, $FiO_2$. In a normal resting person, this ratio is 100/0.21=450. A ratio below 300 indicates a compromised lung, and a ratio less than 200 indicates acute respiratory distress syndrome (ARDS). However, in order to validate this measure as an assessment tool in the OCS, several normalizing adjustments are required. One critical adjustment is for the level of deoxygenation of the blood before it enters the lung, $PvO_2$. In general, $PvO_2$ levels are higher in the OCS than in a person because of the limited deoxygenation capability of the gas exchanger. Thus, for a given gas exchange capability of a lung, a higher $PaO_2$ is expected from a lung in the OCS's continuous assessment mode than in vivo.

Another measure of the gas exchange capacity of the lungs is the difference between oxygen levels of blood entering the lungs, $PvO_2$, and that of the blood leaving the lungs, $PaO_2$. In a normal person, the $PvO_2$ level is about 40 mm Hg and $PaO_2$ is about 100 mm Hg, with a difference between outgoing and incoming oxygen levels of 60 mm Hg. On the OCS, the $PvO_2$ level may be 60 mm Hg, and a healthy lung may achieve a $PaO_2$ of 115 mm Hg, with a $PaO_2$-$PvO_2$ value of 55 mm Hg, close to the corresponding value in vivo.

In order to validate measured continuous mode parameters as an assessment tool, several normalizing adjustments are required. These adjustments are based on factors such as ventilation parameters, hematocrit levels, blood flow rate, lung volume, altitude, and temperature.

Sequential Assessment Mode

Sequential assessment mode is a second method of evaluating the lungs' gas exchange capability. In this mode, the lungs receive deeply venous perfusate oxygen levels that subject them to a different capability test than that of continuous assessment mode.

Figure 35:
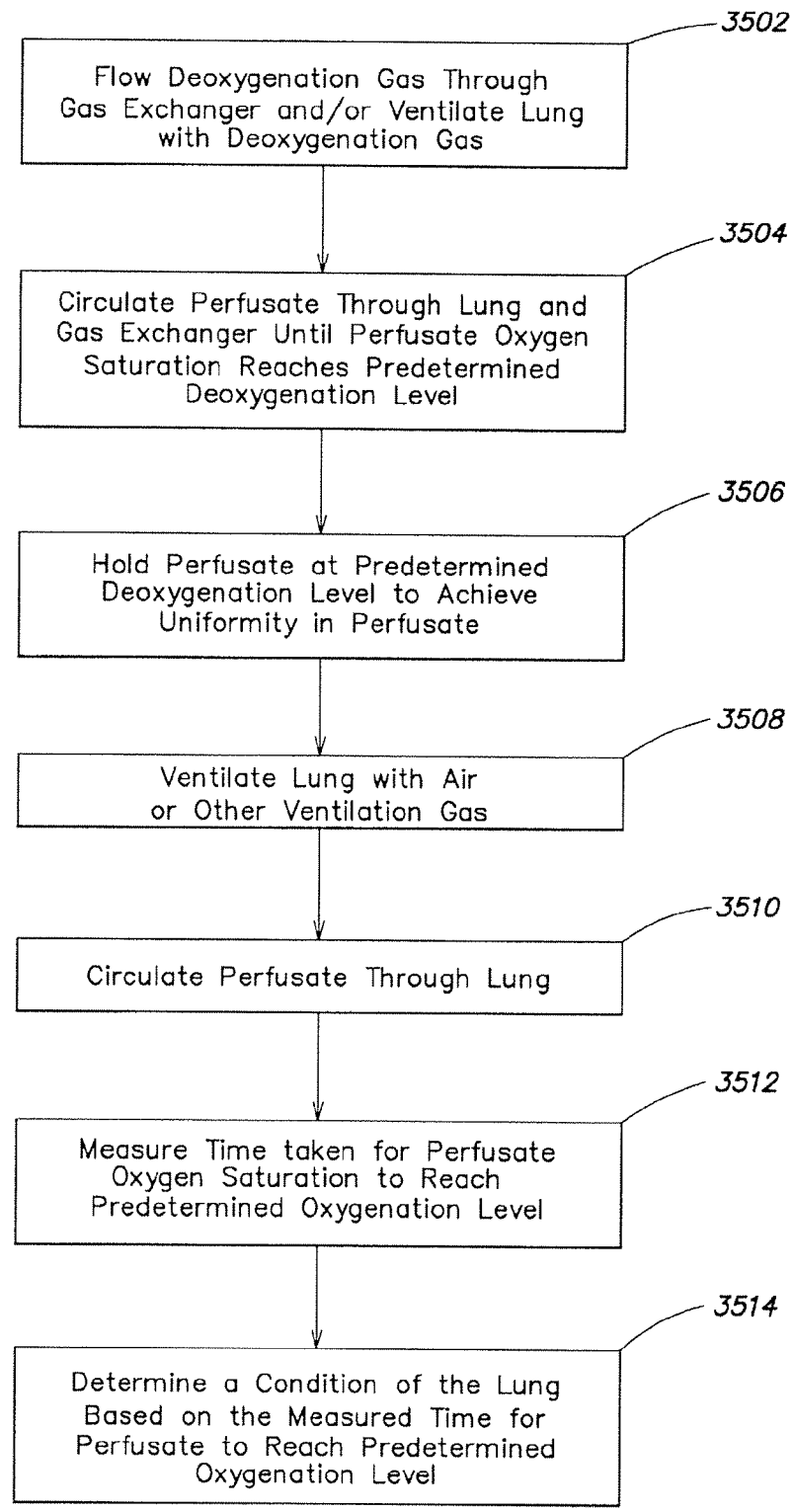
FIG. 35 is a flow diagram showing steps performed during sequential assessment of lungs ex vivo.

Sequential assessment includes three phases: deoxygenation, hold, and reoxygenation. The deoxygenation phase removes oxygen from all the perfusate in the system. After the hold phase, the lungs then reoxygenate the perfusate pool. The speed at which they achieve reoxygenation is an indication of their gas exchange capability. FIG. 35 shows the principal steps involved in performing a sequential assessment of the lungs.

Deoxygenation phase 3502, 3504 is used to lower the oxygen content of perfusion fluid 250. This is achieved by using both gas exchanger 402 and lungs 404. To cause gas exchanger 402 to deoxygenate the blood, deoxygenation gas 500 is fed into it by setting gas selector valve 216 to select deoxygenation gas, and opening gas exchanger valve 204. Although the gas exchanger can deoxygenate the blood on its own, the process is expedited by using the lungs and the ventilator. To accomplish this, the ventilator is configured to run as a rebreather, as in maintenance mode (see above), and trickle valve 212 injects deoxygenation gas 500 into the gas circuit. Within a few ventilator cycles, the rebreathed gas in the gas circuit conforms to the deoxygenation gas composition, i.e., about 6% $CO_2$ and 94% $N_2$, and the lungs act to deoxygenate the perfusion fluid circulating through them. In effect, the lungs are being used as a very effective gas exchanger to help deoxygenate the perfusate pool. As indicated in FIG. 35, step 3504, the deoxygenation phase continues until the perfusate oxygen falls to a user-defined threshold value, which is usually approximately 50-70% oxygen, and preferably about 60% oxygen.

In hold phase 3506, the deoxygenation process is halted by closing gas exchanger valve 204 and trickle valve 212 while perfusate continues to flow through the perfusion circuit. During this phase the perfusate pool is allowed to stabilize to a uniform level of deoxygenation. The time required to achieve uniformity may depend on the perfusate flow rate. In an alternate embodiment, arterial and venous oxygen content levels are monitored, and the hold phase is maintained until the levels become equal and constant over time. During the hold phase, ventilation is halted, or, alternatively, the system performs one or more purge cycles (described above in the continuous assessment section) to prepare for the reoxygenation phase. The purge cycle serves a useful role here because the gas in the gas circuit is being switched from deoxygenation gas to air, its polar opposite, and in order to start oxygenating the perfusion fluid immediately, the gas circuit needs to be filled with air at the outset.

In the final phase of sequential assessment mode, the oxygen-depleted perfusate pool is reoxygenated by ventilating the lungs with air or another ventilation gas (step 3508). The ventilation is performed using the same method as described above for continuous assessment, with the difference that gas exchanger valve 204 is kept closed. Thus in the reoxygenation phase of sequential assessment mode, the lungs are the only source of gas exchange in the perfusion circuit (step 3510). The time taken for the lungs to reoxygenate the perfusate pool is the key indicator of the lung gas exchange capability. The measured reoxygenation time is the time for perfusion fluid 250 to go from a de-oxygenated state to a predetermined oxygenated level as measured by one or both of pulse oximeter probes 116 and 118 (step 3512). In an alternative embodiment, blood samples are taken from one or more of sampling ports 234, 236 and the saturation levels are measured by a lab blood gas analyzer. The saturation at the oxygenation threshold level is set in the range of 90% to 100% and is preferably set at 93%.

The gas exchange capability of the lungs, as measured by the time taken for the air-ventilated lungs to reoxygenate the blood from the deoxygenation threshold level to the oxygenation threshold level provides a measure of the condition of the lungs (step 3514). In general, a healthy lung will be able to reoxygenate the perfusate pool in 4-5 breaths, which corresponds to a sequential assessment mode reoxygenation time in the range of 45 to 90 seconds, and typically approximately one minute. Validation of the reoxygenation time as an assessment tool may require normalization based on ventilation parameters, hematocrit, blood flow rate, lung volume, and altitude.

In an alternative embodiment of sequential mode assessment, a gas other than air is supplied to the inlet of check valve 416 during the oxygenation phase. For example, gas from devices that provide gas at 50% or 100% oxygen in a hospital setting can supply the ventilation gas. In this case, reoxygenation times are reduced, and to determine the lungs' gas exchange capability, the reoxygenation time measurements need to be appropriately calibrated.

Another method of assessing lung gas exchange capability during sequential assessment mode is to measure the speed at which the lungs deoxygenate perfusion fluid 250 during the deoxygenation phase. The effectiveness of the lungs in deoxygenating perfusion fluid 250 while being ventilated with deoxygenation gas 500 provides an indication of the lungs' gas exchange capability.

An advantage of sequential assessment mode is that physiologic blood flow rates of 3-4 l/minute can be used because, during reoxygenation, gas exchange is being performed only by the lung. Since the gas exchanger is not involved, there is no need to limit blood flow.

Lung Ventilator Pneumatic Circuit

The lung ventilator pneumatic circuit provides a means of controlling bellows valve 414 and relief valve 412 for controlling various modes of ventilation. It also controls gas flow to blood gas exchanger 402 and the lungs. Pneumatic control offers several advantages, including the ability to open and close valves at different rates, the availability of inexpensive, disposable pilot valves, the ability to isolate lung console module 200 from the valves carrying gases exposed to the lung, and providing a convenient and modular interface for connecting and disconnecting disposable lung perfusion module 400 to console module 200.

Figures 5A, 5B:
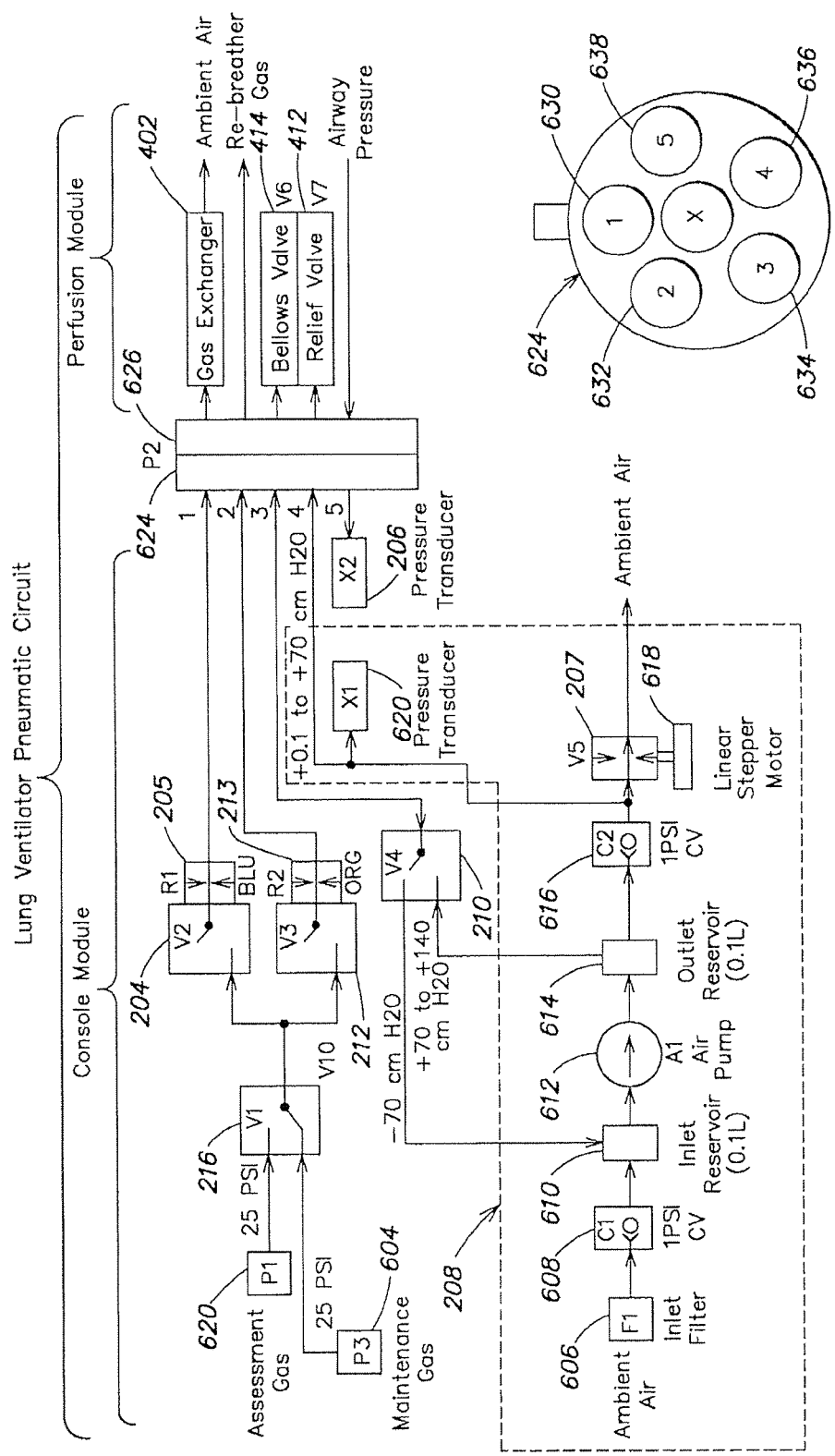
FIGS. 5A-5B are a schematic diagram of the lung ventilator pneumatic circuit, according to the described embodiment.

Software running on console module controller 202 controls pneumatic control module 208, which in turn controls relief valve actuator 207 and bellows valve actuator 210. FIG. 5*a* shows the components of the pneumatic circuit in lung console module 200, and how the circuit connects to lung perfusion module 400. The components corresponding to pneumatic control module 208 as indicated on FIG. 1 are identified by the dotted line in FIG. 5*a*. Table 1 is a list of the pneumatic circuit parts according to the described embodiment.

TABLE 1

| Ref. No. in FIG. 5a | Part Description |
|---|---|
| 216 | V1: Gas Selector Valve, 3 way 15 SLPM, 25 PSI MAX Line Pressure, ASCO AL2312, 0.65 W, 0.055" (4.3 PSI drop @ 15 SLPM) |
| 204 | V2: Blood Gas Valve, 2 way NC, 10 SLPM, 25 PSI MAX Line Pressure, ASCO AL2112, 0.65 W, 0.055" (2 PSI drop @ 10 SLPM) |
| 212 | V3: Re-breather Gas Valve, 2 way NC, 5 SLPM, 25 PSI MAX Line Pressure, ASCO AL2112, 0.65 W, 0.55" (0.6 PSI drop @ 5 SLPM) |
| 210 | V4: Bellows Pilot Valve, 3 way, 1.5 SLPM, 3 PSI MAX Line Pressure, ASCO AL2312, 0.65 W, 0.55" (2.5 cm H2O drop @ 1.5 SLPM) |
| 207 | V5: Relief Pilot Linear Pressure Control, Variable Orifice (0.020" to 0.170" Using Linear Stepper motor, Haydon 20544-05-018, 2.5 W (0.1 to 70 cm H2O drop at 1.8 to 2.5 SLPM) |
| 414 | V6: Bellows Valve, Instrument Industries BE 30-115-BL |
| 412 | V7: Relief Valve, Instrument Industries BE 30-115-BL |
| 205 | R1: Blood Gas Restrictor, Bird Precision RB 82304 BR (SA087)-24054, 10.8 SLPM @ 25 PSI, 0.0290" |
| 213 | R2: Ventilator Gas Restrictor, Bird Precision RB 82304 BR (SA087)-24060, 5.7 SLPM @ 25 PSI, 0.0210" |
| 608, 616 | C1, C2: Check Valve, 1 PSI, McMaster Carr 6079T54 |
| 606 | F1: Filter, McMaster Carr 8991T312 |
| 602 | P1: Assessment Gas Connector Colder PMC1602 |
| 624 | P2: Perfusion Module Gas Connector, Colder SM1702 (six lumen) |
| 604 | P3: Maintenance Gas Connector, Colder PMC1702 |
| 206 | X1: Airway Pressure (PEEP, PAWP sensing) |
| 620 | X2: Relief Valve Pilot Pressure (for controlling relief valve) |

TABLE 1-continued

| Ref. No. in FIG. 5a | Part Description |
|---|---|
| 612 | A1: Air Pump, 1.5 SLPM @ 3 PSI, Hargraves H103-11_B.1F28E1.A12VDC, 3 W |

The pneumatic circuit of lung console module 200 connects to lung perfusion module 400 via gas connectors 624, 626. FIG. 5b shows a front view of connector 624, showing a six-lumen connector, with gas lines 630, 632, 634, 636, and 638 providing connections to gas exchanger 402, the rebreathing gas circuit, bellows valve 414, relief valve 412, and airway pressure respectively. The connector permits rapid removal and hookup of disposable lung perfusion module 400 to lung console module 200.

Maintenance gas 220 and deoxygenation gas 500 are connected to gas selector switch 216 by connectors 604 and 602 respectively. Gas selector switch 216 selects which gas to pass through gas exchanger valve 204 and trickle valve 212. The control of trickle valve 212 is synchronized with the ventilation cycle; the valve is opened during the inhalation phase, as described above for FIG. 6, and is kept open for long enough to obtain the desired average gas flow rate. The rate of flow to gas exchanger 402 is controlled by pulse width modulation of the control valve 204 from valve 216. Valves 204 and 212 effect control of the gas flow rate using orifice restrictors 205 and 213 respectively.

Bellows valve 414 and relief valve 412 are both capable of high flow rates, such as 1 liter/second. In the case of bellows valve 414, the high flow rate capability allows non-restrictive, free gas flow between the lungs and the bellows during inhalation and exhalation. In the case of relief valve 412, the high flow rate capability allows the lungs to exhale rapidly to the PEEP value. In the described embodiment, bellows valve 414 and relief valve 412 are commercially available high flow rate pilot valves. Applying positive pressure to the pilot valve diaphragm closes the valve; negative pressure fully opens the valve.

The lower section of FIG. 5a shows how pilot valve control is achieved for bellows valve 414 and relief valve 412. Air pump 612 runs constantly, providing an approximately constant flow of air through the pump. The pump draws in ambient air through inlet filter 606, and check valve 608. This flow creates a pressure difference across check valve 608 of about 1 PSI, or 70 cm of $H_2O$, which results in a pressure in inlet reservoir 610 pressure of −70 cm of $H_2O$ relative to ambient pressure. Inlet reservoir 610 and outlet reservoir 614 serve to filter the uneven pressure ripple from reciprocating pump 612. After passing through outlet reservoir 614, the outlet of air pump 612 flows through second 1 PSI check valve 616. Thus the pressure in outlet reservoir 614 is 70 cm of $H_2O$ above ambient, provided relief valve actuator 207 is open to ambient pressure.

Bellows valve 414 is controlled as follows. Bellows valve actuator 210 can be connected to either inlet reservoir 610 or outlet reservoir 614. To open bellows valve 414, actuator 210 is connected to inlet reservoir 610, which is at −70 cm of $H_2O$. Actuator 210 causes this negative pressure to be transferred via pneumatic line 634 to the diaphragm of bellows valve 414. The negative pressure on the diaphragm causes valve 414 to open. To close bellows valve 414, actuator 210 is connected to outlet reservoir 614 at +70 cm of $H_2O$, causing positive pressure to be applied to the valve diaphragm, which shuts off the valve.

Relief valve 412 is controlled by applying a positive pressure to the valve's diaphragm, but in this case a controllable pilot gas pressure of the valve is used to set the PEEP in the perfusion module gas circuit. Relief valve 412 remains open, and gas in the ventilation loop is vented to the outside, as long as the pressure in the ventilation loop is greater than the pilot pressure on the valve's diaphragm. When the pressure in the ventilation loop falls below that of the pilot pressure, relief valve 412 closes. Thus by setting the pilot pressure to the desired PEEP value, the relief valve allows gas to vent from the gas loop until the pressure falls to the desired PEEP level, and then it shuts off. In alternate embodiments, the PEEP valve is actuated with higher or lower pilot pressure to effect the exhalation rate through the valve.

Variable control of pilot pressure in relief valve 412 is achieved by using linear stepper motor 618 in conjunction with a variable orifice valve in relief valve actuator 207. Stepper motor 618 controls the size of the opening of the variable orifice valve. The smaller the opening of the orifice, the more resistance to airflow, the less airflow from air pump 612 escapes to the ambient air, and the higher the pressure between check valve 616 and relief valve actuator 207. This pressure is transmitted to relief valve 412 via pneumatic line 636. This enables the processor to obtain an empirically calibrated relationship between relief valve pilot pressure and PEEP. The actual pilot pressure is measured by relief pilot valve pressure sensor 620; this is monitored by lung console module processor 202, which also receives measurements of airway pressure from airway pressure sensor 206. In an alternate embodiment, the pilot pressure measurement is used to control the pilot pressure by comparing the actual pilot pressure to the desired pilot pressure and changing the stepper motor position to equalize them.

System Information Display and System Monitoring

OCS monitor 300 is the main input and output interface for the system operator. LCD 304 displays real time measurements and derived values of interest for the perfusion solution and for the gas loop. It also displays the status of other OCS subsystems, such as battery levels and gas tank levels. The nature of the information displayed on OCS LCD display 402 is explained next. Following this, screen shots corresponding to maintenance mode, continuous assessment mode, and sequential assessment mode are described.

Figure 11:
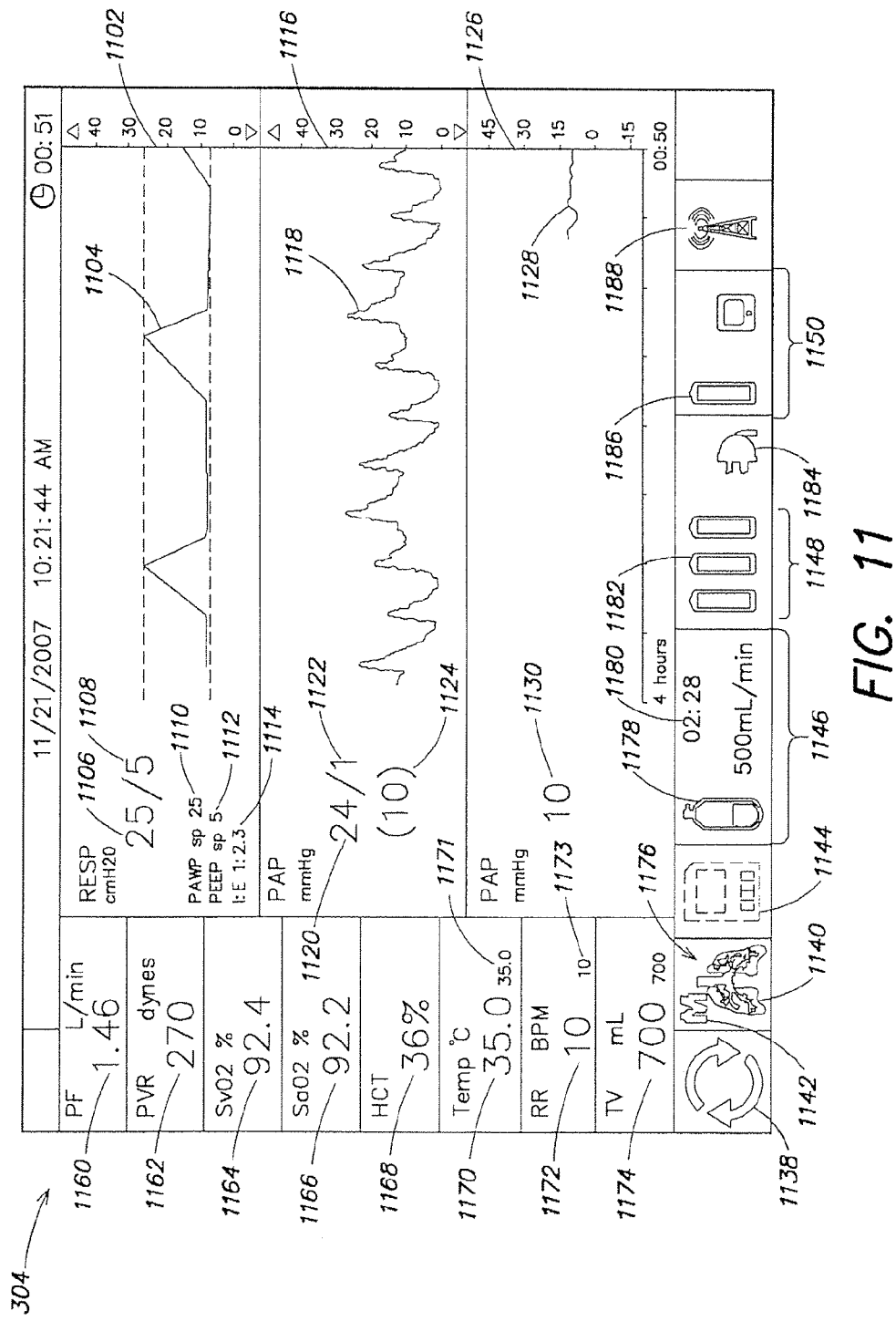
FIG. 11 is a screenshot of the monitor of the organ care system in maintenance mode, according to the described embodiment.

FIG. 11 is an exemplary screen shot of LCD 304; the screen shot corresponds to maintenance mode. LCD 304 includes a display area 1102 showing real time trace 1104 of the ventilation pressure at the entrance to the lungs, as measured by airway pressure sensor 206. The display also includes numerical values 1106, 1108 of the ventilation pressure readings; numerator 1106 is the peak pressure value, which is the maximum pressure sampled over the entire ventilation cycle. Denominator 1108 is the PEEP value for the last respiration cycle, which is derived by sampling the airway pressure at the end of the expiratory time, i.e., just before inhalation for the next cycle begins. Since PEEP is defined as the pressure right at the end of the respiration cycle, it does not necessarily correspond to the minimum pressure in the cycle. Lower pressures may occur in the system if, for example, the system overshoots or undershoots as it attempts to reach the set PEEP value. Additional numerical values 1110, 1112, and 1114 show the configured set point (sp) values, i.e., the values selected by the user. The display of these values helps the user compare the displayed actual values of respiratory pressure with the configured desired values. Value 1110 shows the set point value for PAWP, which is an absolute upper pressure limit, or clamp, on the respiratory pressure. Generally, the ventilation pressure waveform is below the PAWP limit at all times. As described above, the PEEP set point 1112 corresponds to the desired respiratory pressure at the end of a respiration cycle, after exhalation is complete and just before the inhalation pressure ramp of the next cycle starts. Value 1114 shows I:E, which is the ratio of the respiration cycle time associated with inspiration and exhalation. The inspiration period includes both the inhalation time corresponding to flowing gas into the lungs, i.e., inhalation ramp 654 (FIG. 6), as well as the plateau time 658. Thus I:E= (inspiratory time+plateau time):expiratory time. The system derives the I:E value from the configured inspiratory time, plateau time, and respiration rate.

Display area 1116 of LCD 304 shows a real time trace 1118 of pulmonary arterial pressure (PAP) as measured by pressure sensor 115. Also displayed are PAP numerical values showing a snapshot of key values: peak or systolic pressure 1120, valley or diastolic pressure 1122, and mean perfusate pressure 1124 at the pulmonary artery feed at the lung.

Figure 12:
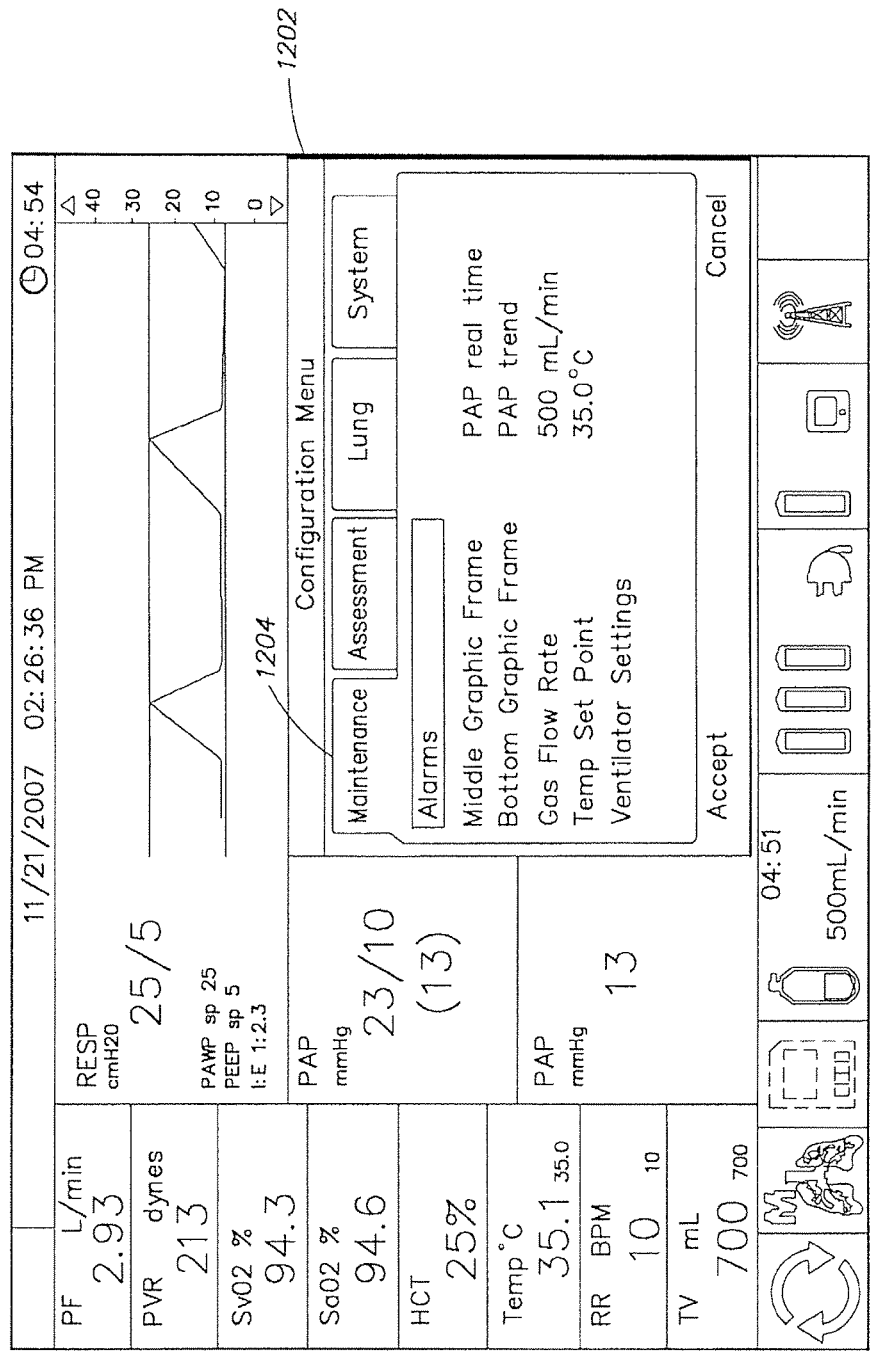
FIG. 12 is a screenshot of the monitor of the organ care system in maintenance mode showing the configuration menu maintenance tab, according to the described embodiment.

In lower display area 1126, time averaged graph 1128 of PAP is displayed, together with numerical value 1130 displaying the average PAP value. The choice of what to display on LCD 304 is under operator control. FIG. 12 shows configuration menu 1202, with maintenance tab 1204 selected. In this mode, the operator can select what information to display in each of middle graphic area 1116 and bottom graphic area 1126. Upper graphic frame 1102 is also configurable (not shown). The configuration menu maintenance tab also provides the ability to set the average flow rate of maintenance gas 220 through trickle valve 212, as well as control the perfusate temperature. Other parameters of the lung ventilator can also be controlled via the maintenance tab menu.

LCD 304 displays a number of additional numerical values that provide the system user with a snapshot of the lung condition and OCS parameters. Displayed value 1160 shows pulmonary flow (PF) of perfusate into lungs 404 as measured by flow rate sensor 114. Displayed value 1162 shows pulmonary vascular resistance (PVR), which is a measure of the resistance exerted by lungs 404 to the flow of perfusate. In general, a lower PVR value is preferable because it indicates a less restrictive flow of the perfusate through the vasculature of lungs 404. In the described embodiment, favorable values of PVR are in the range of 200 to 400 dynes. Displayed value 1164 shows venous saturation hemoglobin content, $SvO_2$ of perfusion fluid 250, as measured by oxygen sensor 116. Similarly, displayed value 1166 shows arterial saturated hemoglobin content, $SaO_2$ of perfusion fluid 250, as measured by oxygen sensor 118. In certain embodiments, icons indicating $SVO_2$ and $SaO_2$ alarms are displayed adjacent to displayed values 1164 and 1166 respectively, for signaling the operator if either saturated hemoglobin value falls below an operator preset threshold. Such alarms may be implemented for any parameter measured, calculated or displayed. Displayed value 1168 shows the hematocrit (HCT) level of perfusion fluid 250 and, optionally, an HCT alarm indicator for signaling the operator if the HCT level 1168 falls below an operator preset threshold. Displayed value 1170 indicates the temperature (Temp) 1170 of perfusion fluid 250 as it flows away from heater assembly 230. Displayed value 1170 may also include a Temp alarm indicator which signals in response to Temp 1170 being outside of an operator preset range. Temperature set point 1171 selected by the operator is also shown. Display area 1172 shows a numerical reading of the ventilation rate measured in breaths per minute (BPM) of a gas delivered to lungs 404 via the tracheal interface 1024. The BPM value is derived from one or more inputs, including readings from airway pressure sensor 206. In addition, BPM set point 1173, as selected by the operator, is displayed. Displayed value 1174 shows the tidal volume (TV), the volume of gas flowing into lungs 404 during each inhalation.

LCD 304 further includes circulatory pump indicator 1138 showing a status of the system's circulatory pump. Display area 1176 shows an organ type indicator 1140 that indicates which organ is being perfused and an organ mode indicator 1142 that indicates what mode of operation is being used. For example, an "M" is used to indicate maintenance mode. SD card indicator 1144 shows whether an SD card is used to store data collected during organ perfusion. Display area 1146 includes gas tank diagram 1178 that graphically indicates remaining maintenance gas volume. Display area 1146 also includes one or more numerical displayed values 1180 indicating a flow rate of the gas in the gas supply along with the time remaining for which the gas is delivered to lungs 404 during perfusion. This remaining time may be calculated based on the remaining gas volume and the gas flow rate. Display area 1148 shows graphical representation 1182 of the degree to which each of the batteries of OCS console 100 are charged. Battery status symbol 1184 indicates that the batteries whose status are represented by graphical representation 1182, are used to power OCS console 100. Display area 1150 shows graphical representation 1186 of the degree to which the battery that powers the user interface is charged. Display area 1188 identifies whether the OCS monitor 300 is operating in a wireless fashion.

In other embodiments, display screen 304 also shows $FiO_2$ and $FiCO_2$ concentrations, which are fractional concentrations of oxygen and carbon dioxide, respectively, measured at the entrance to the trachea. Display screen 406 can additionally show readings of weight and elasticity of lungs 404, PH of perfusion fluid 250 circulating through the lungs 1004, partial pressures of gas components in perfusion fluid 250, and PEEP levels.

The information displayed on OCS monitor LCD 304 is now described in relation to the mode of operation of OCS 1000. As stated above, FIG. 11 shows a lung in maintenance mode; the values displayed in the figure are to be taken as exemplary. As indicated along the left column of data, the perfusate flow rate is 1.46 l/min, a value lower than physiologic levels, but sufficient to nourish the lung. As shown in the figure, $SvO_2$ value 1164 is 92.4% and $SaO_2$ value 1166 is 92.2%. These levels correspond to equilibrium between maintenance ventilation gas 220 and the perfusate gases. The difference between arterial and venous oxygen levels is caused by oxygenation from air entering the organ chamber (tending to increase $SaO_2$), and from the small consumption of oxygen by the lungs (tending to decrease $SaO_2$). The balance between these factors can cause $SaO_2$ to be higher or lower than $SvO_2$. In general, once maintenance mode is fully established, the oxygen saturation values of the perfusate as it enters and exits the lungs are stable and equal to each other within about +/−5%. As oxygen is consumed by the lungs it is continually replaced by trickling in maintenance gas 220 via trickle valve 212 during each ventilation cycle. Graph 1104 shows the ventilation pressure over time; the pressure rises when the bellows pushes air into the lungs, and diminishes to the desired PEEP value at the end of exhalation. The graph shows the pressure profile over the most recent ventilation cycles; display area 1172 shows that the lungs are being ventilated at a rate of 10 breaths per minute. Graph 1118 shows real time PAP corresponding to the most recent ventilation cycles. The curve shows periodic peaks that correspond to the pulse of the circulatory pump 226. Graph 1128 shows the PAP trend. Numerical value 1170 shows that the perfusate temperature is measured to be 35.0 degrees centigrade, and is equal to the set point value shown in numerical displayed value 1171. Such a sub-physiologic temperature level is selected to reduce the metabolic rate of lungs 404 during preservation. One advantage of a lower metabolic rate is the ability to lower the maintenance gas requirement of lungs 404, thereby permitting them to be preserved for a longer time with a finite volume of maintenance gas 220.

Figure 13:
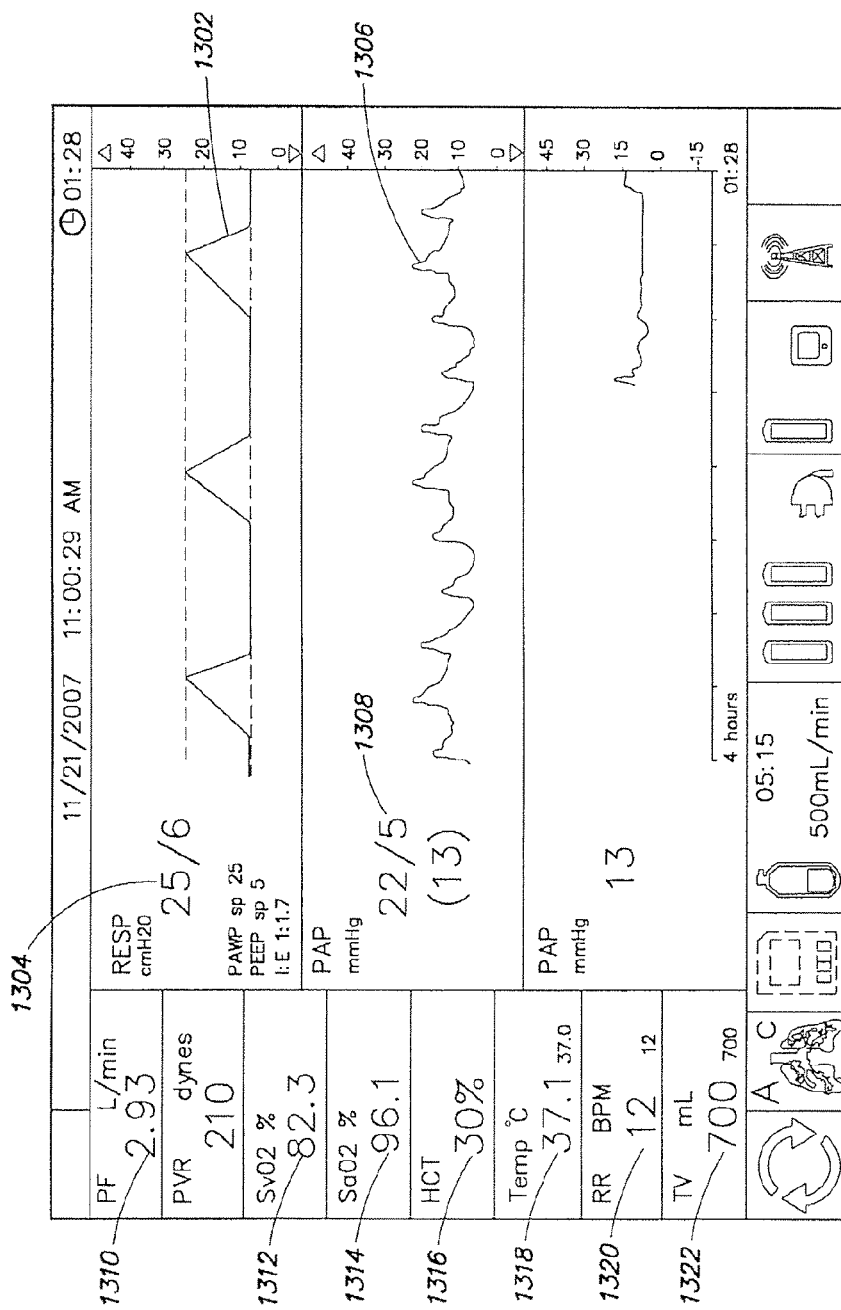
FIG. 13 is a screenshot of the monitor of the organ care system in continuous assessment mode, according to the described embodiment.

FIG. 13 is an exemplary screen shot of OCS monitor LCD 304 when the system is in continuous assessment mode. Respiration graph 1302 and numerical values 1304 are similar to those shown in FIG. 11 for maintenance mode. However, PAP graph 1306 and numerical values 1308 show an average pressure of 13 mm Hg, which is considerably higher than the corresponding 10 mm Hg pressure during maintenance mode. The higher pressure is required to achieve a higher flow rate of perfusion fluid through the lung, so as to allow testing of the lung's gas exchange capability. The screen shows flow rate 1310 at 2.93 liters/minute. In this mode, gas exchanger 402 deoxygenates perfusion fluid 250 to $SvO_2$ level 1312 of 82.3%. The lungs reoxygenate the blood using air ventilation, achieving $SaO_2$ level 1314 of 96.1%. Hematocrit level 1316 is 30%, and perfusate temperature 1318 is maintained at about 37.1 degrees C., the physiologic value. The respiration rate displayed value 1320 shows a rate of 12 breaths per minute, corresponding to that of a resting person. Tidal volume displayed value 1322 shows a value of 700 ml, well within the physiologic range. OCS status display 1324 shows a graphic of the lungs, indicating that OCS 1000 is preserving a lung, and the letters A and C, indicating that the system is in continuous assessment mode.

Figure 14:
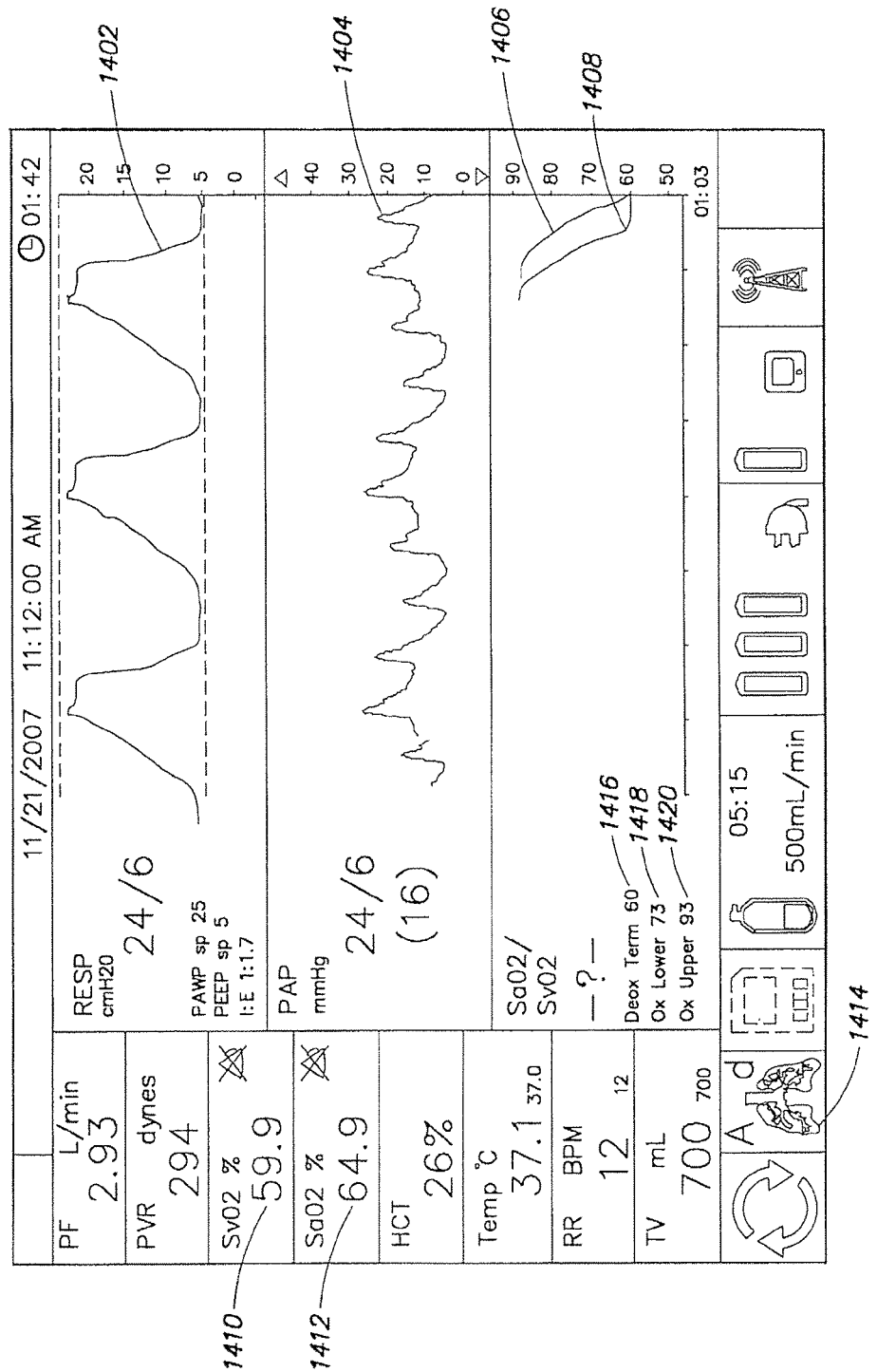
FIG. 14 is a screenshot of the monitor of the organ care system in sequential assessment mode, deoxygenation submode, according to the described embodiment.

Having described the system display corresponding to maintenance mode and continuous assessment mode, we now describe how the deoxygenation, hold, and oxygenation phases of sequential assessment mode are displayed on LCD 304. FIG. 14 is an exemplary screen shot of LCD 304 when the system is in deoxygenation phase. In this phase, deoxygenation gas 500 is passed through gas exchanger 402 and into the ventilation loop into lungs 404. Oxygen levels in perfusion fluid 250 drop rapidly, since oxygen is being removed by gas exchange both in lungs 404 and gas exchanger 402. Graphs 1406 and 1408 show the values of $SaO_2$ and $SvO_2$ respectively over a period of about one minute after the start of the deoxygenation phase. During this time, the values drop from the low nineties down to a $SaO_2$ value of 64.9% and a $SvO_2$ value of 59.9%, as indicated at the right end of graphs 1406 and 1408 and in numerical displayed values 1412 and 1410 respectively. Thus, perfusate saturation levels well below the physiologic range can be achieved rapidly, especially when lungs 404 supplement the gas exchange capability of gas exchanger 402. Ventilation pressure graph 1402 and PAP levels remain similar to those of continuous assessment mode. System status display 1414 indicates lung assessment—deoxygenation phase, with the letters A, D. Also displayed are the user-determined values for the deoxygenation termination threshold 1416, oxygenation phase lower threshold 1418, and oxygenation phase upper threshold 1420.

Figure 15:
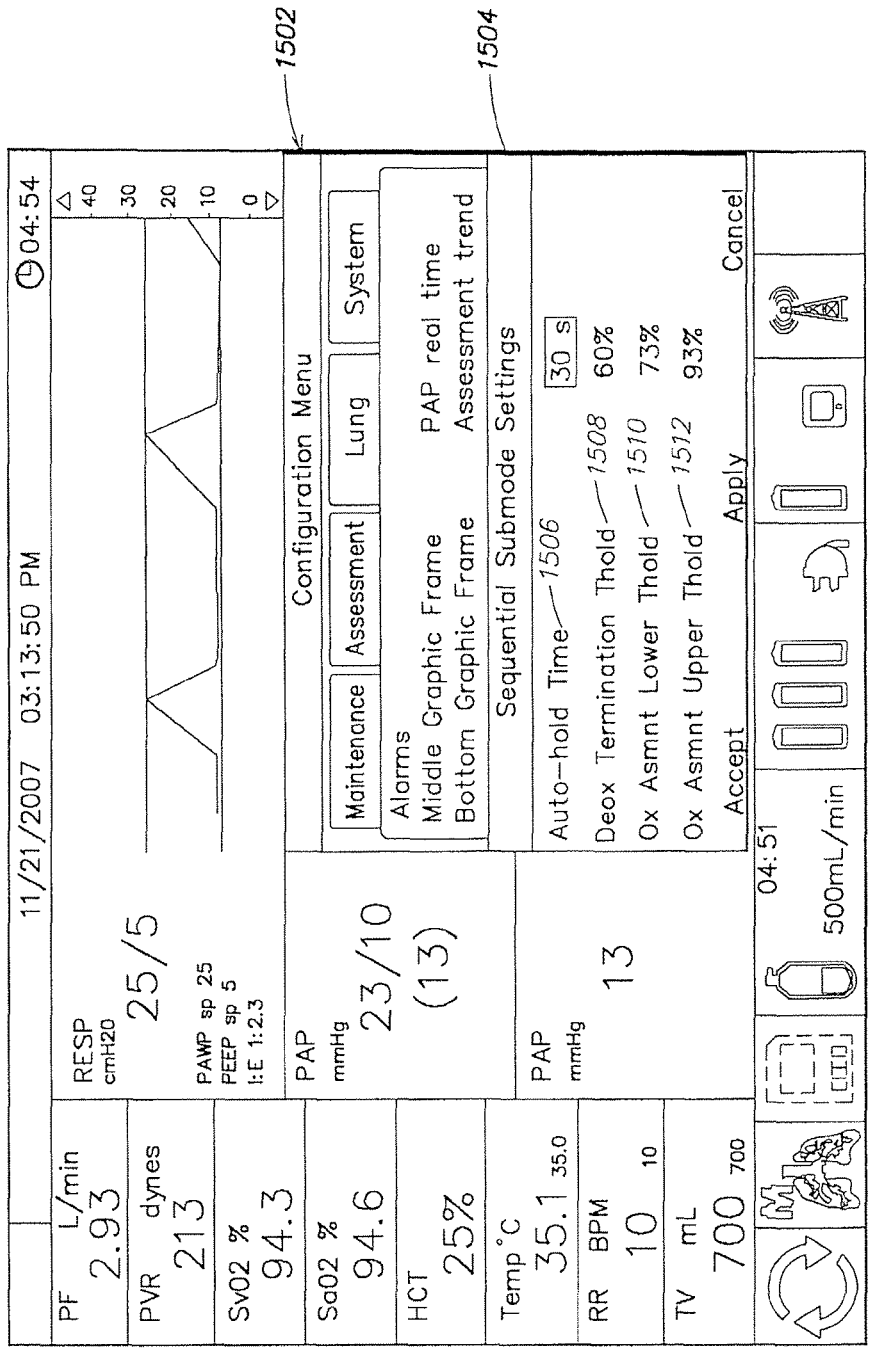
FIG. 15 is a screenshot of the monitor of the organ care system showing the configuration menu for the sequential assessment submode setting, according to the described embodiment.

FIG. 15 shows an exemplary user interface for setting sequential assessment parameters. Configuration mode 1502 is selected by pressing menu button 306 on OCS monitor 300. The user enters and applies settings in sequential submode settings menu 1504. Listed are user-settable values for hold time 1506, which is the time between the end of the deoxygenation phase and the start of the oxygenation phase, and deoxygenation termination threshold 1508, which is the target lowest level of oxygen content in perfusion fluid 250, i.e., the system stops deoxygenation if/when this level is reached. The user also sets values for oxygenation lower threshold 1510, the target value for perfusate $SvO_2$ in the oxygenation phase, and oxygenation upper threshold 1512, the target value for perfusate $SaO_2$ in the oxygenation phase.

Figure 16:
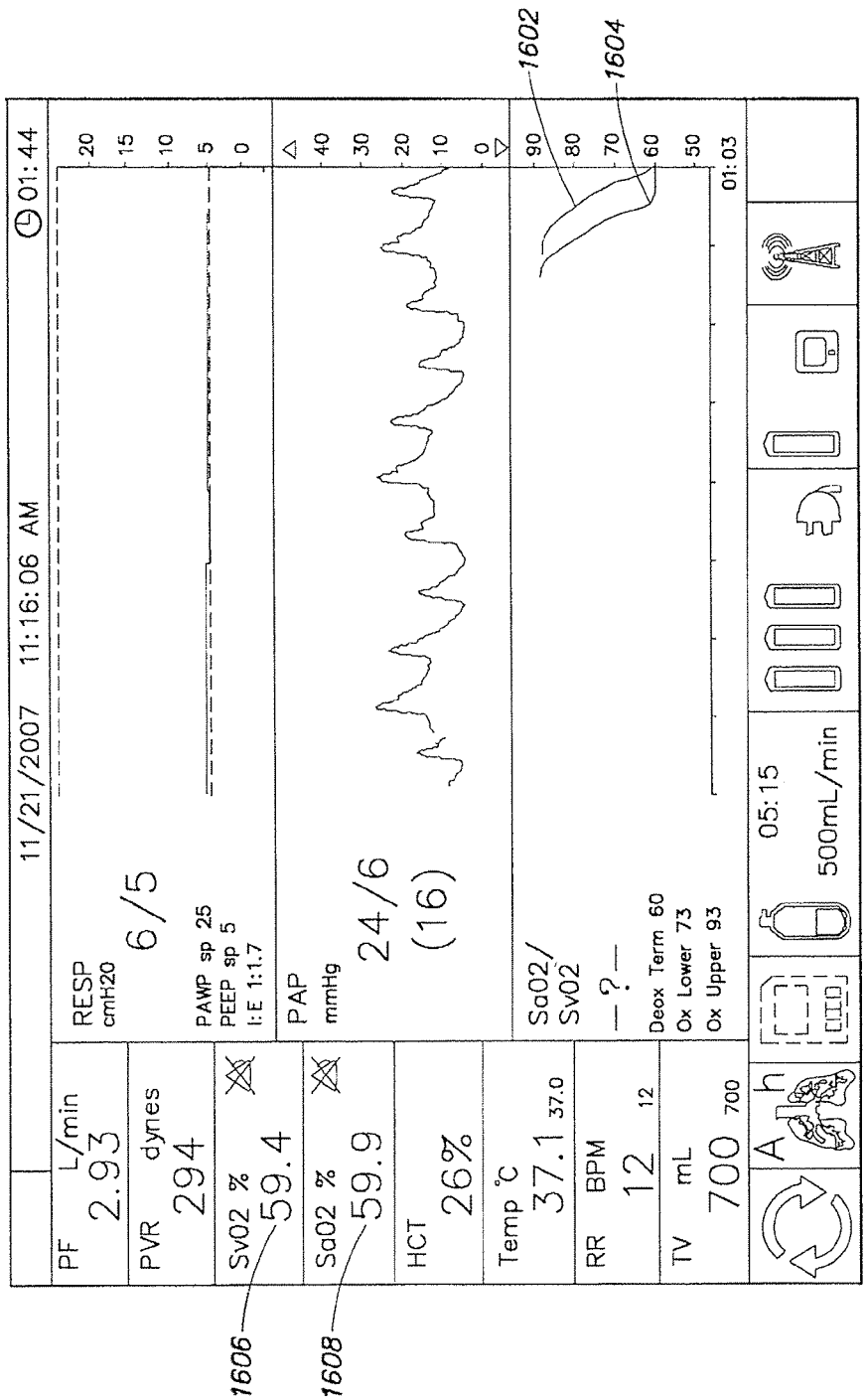
FIG. 16 is a screenshot of the monitor of the organ care system in sequential assessment mode, hold submode, according to the described embodiment.

After deoxygenation mode, the system enters hold phase. FIG. 16 is an exemplary screen shot corresponding to hold phase. The purpose of hold phase is to allow the oxygen levels in perfusion fluid 250 to become uniform. The extent to which this is achieved can be seen in graphs 1602 and 1604, showing the time-changing values of $SaO_2$ and $SvO_2$ in perfusion fluid 250. The flat parts of both curves indicate the saturation levels are constant, and the closeness of the graphs for $SaO_2$ and $SvO_2$ indicate uniformity of the saturation levels on each side of lungs 404. Numerical displayed values 1608 and 1606 indicate values of $SaO_2$ and $SvO_2$ respectively. As shown in FIG. 16, the measured values of $SaO_2$ and $SvO_2$ about one minute into the hold phase are 58.9% and 58.0% respectively, i.e., very close to each other.

Figure 17:
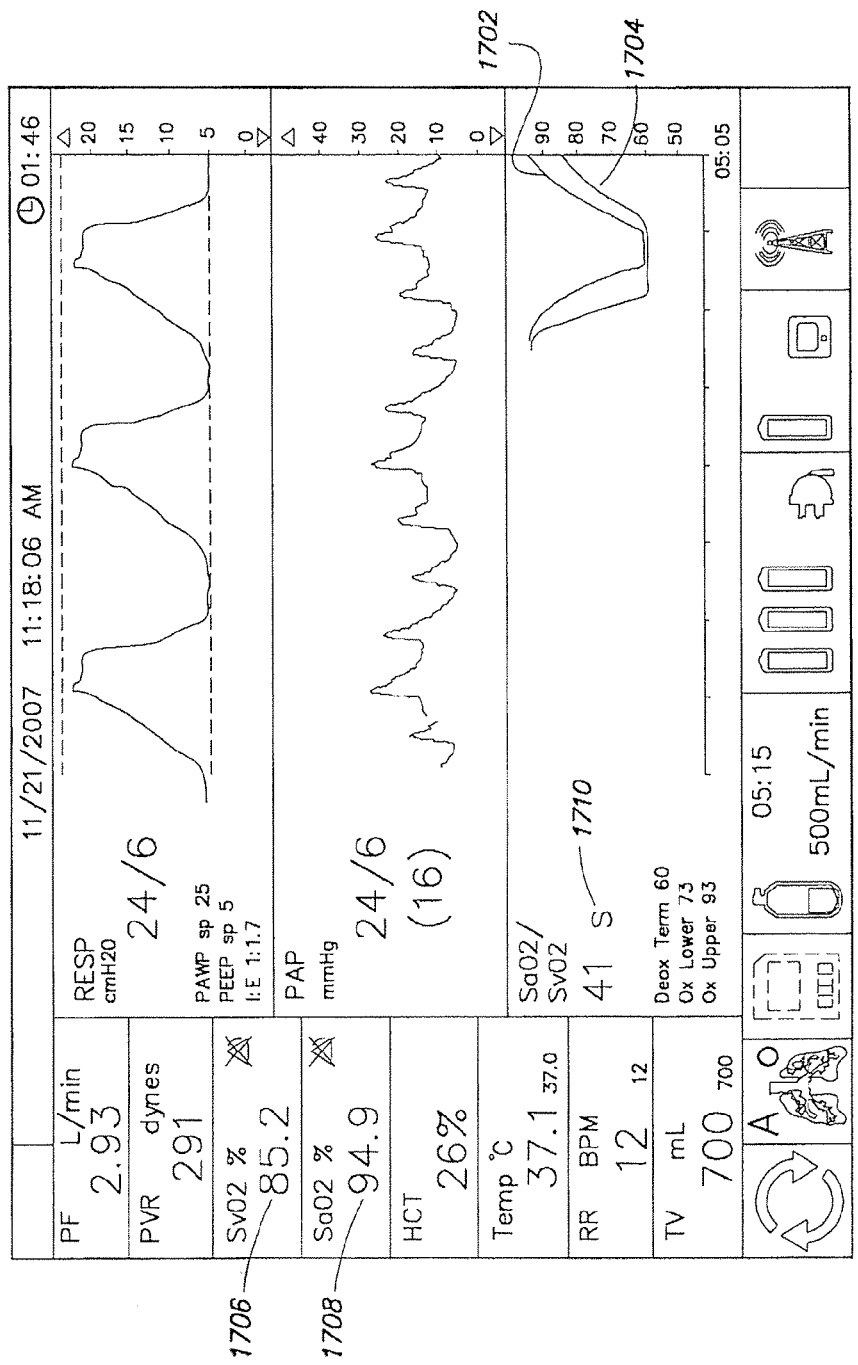
FIG. 17 is a screenshot of the monitor of the organ care system in sequential assessment mode, oxygenation submode, according to the described embodiment.

In the third phase of sequential assessment mode, perfusion fluid 250 is reoxygenated by lungs 404, while being ventilated with air. The gas exchange capability of the lungs is related to the time taken to fully reoxygenate the perfusate pool. FIG. 17 is an exemplary screen shot of the system in the reoxygenation mode. Graphs 1702 and 1704, show the time-changing values of $SaO_2$ and $SvO_2$ in perfusion fluid 250. Towards the left side, the graphs show the initial decline of the oxygen levels during the deoxygenation phase described above. The flat portions of the curves in the middle of the graphs correspond to the hold phase, which lasts for about one minute. At the right end of the hold phase flat portion of the graph, oxygenation mode begins. Shortly after switching to oxygenation mode, the graphs start rising, which indicates oxygen gas exchange via the lungs into perfusion fluid 250. Graphs 1702 and 1704 and numerical displayed values 1708 and 1706 show that about 80 seconds into the oxygenation phase, $SaO_2$ and $SvO_2$ levels have climbed to 94.6% and 85.2% respectively. The time taken to reach a user-selected threshold oxygenation level in perfusion fluid 250 is shown in numerical displayed value 1710.

Figure 18:
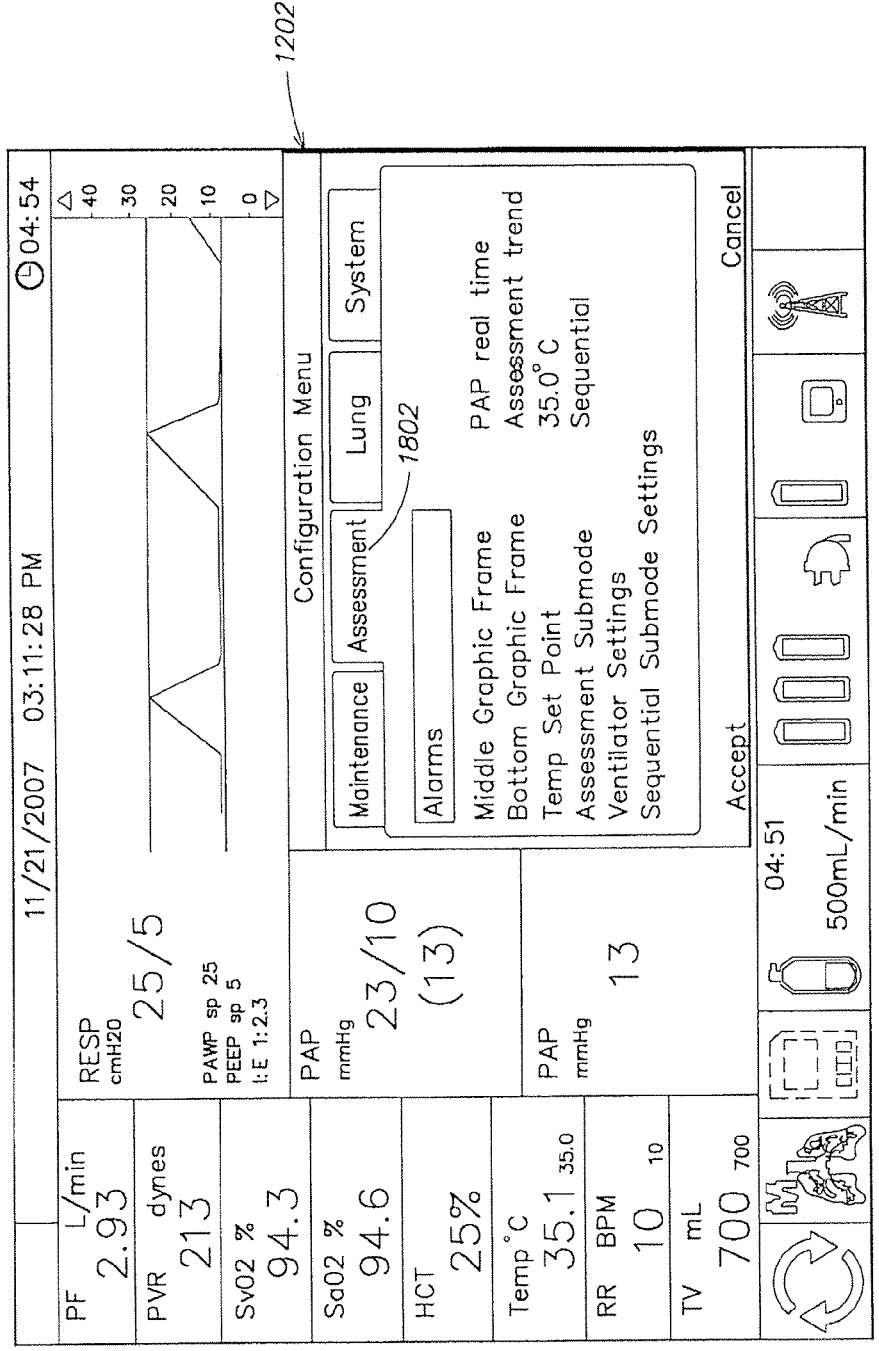
FIG. 18 is a screenshot of the monitor of the organ care system showing the configuration menu for the assessment tab, according to the described embodiment.

Additional screens for configuring OCS 1000 are now described. FIG. 18 shows the assessment tab 1802 of configuration menu 1202. This screen enables the user to determine what information is to be shown in middle graphic frame 1116, in the bottom graphic frame 1126, to set temperature set point 1171, and to choose which assessment mode to perform—sequential or continuous. Tab 1802 also allows the user to select the ventilator setting menu, as well as the sequential assessment submode settings.

Figure 19:
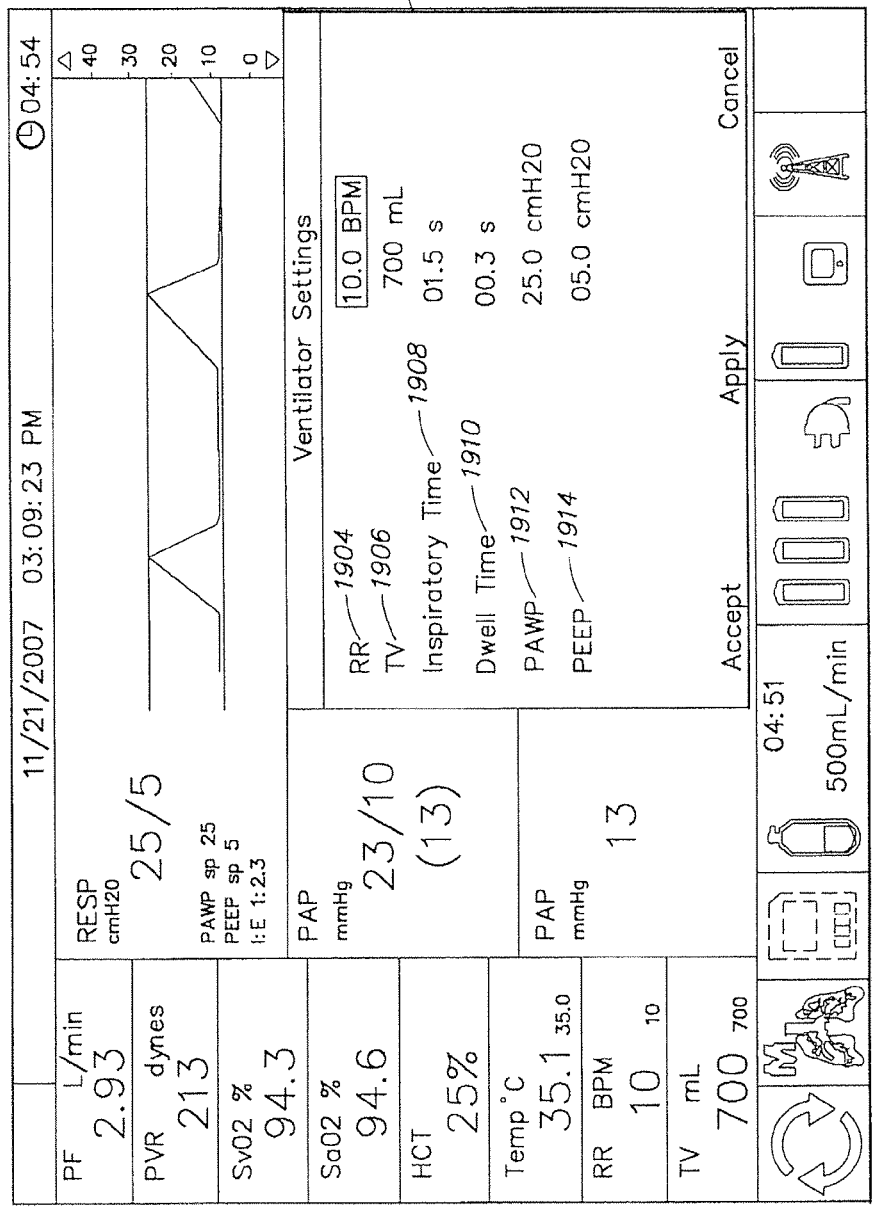
FIG. 19 is a screenshot of the monitor of the organ care system showing the configuration menu for the ventilator settings, according to the described embodiment.

FIG. 19 shows ventilator settings menu 1902. Respiration rate 1904 selects the number of ventilation cycles per minute. Tidal volume 1906 determines the volume of gas inhaled by the lung in each breath. Inspiratory time 1908 is the duration of the inhalation phase. Peak airway pressure (PAWP) 1912 is the maximum allowed gas pressure during the breathing cycle; it occurs while gas is being pushed into lungs 404 by bellows 418. PEEP 1914 controls the pressure in the lung when exhalation is complete.

Figure 20:
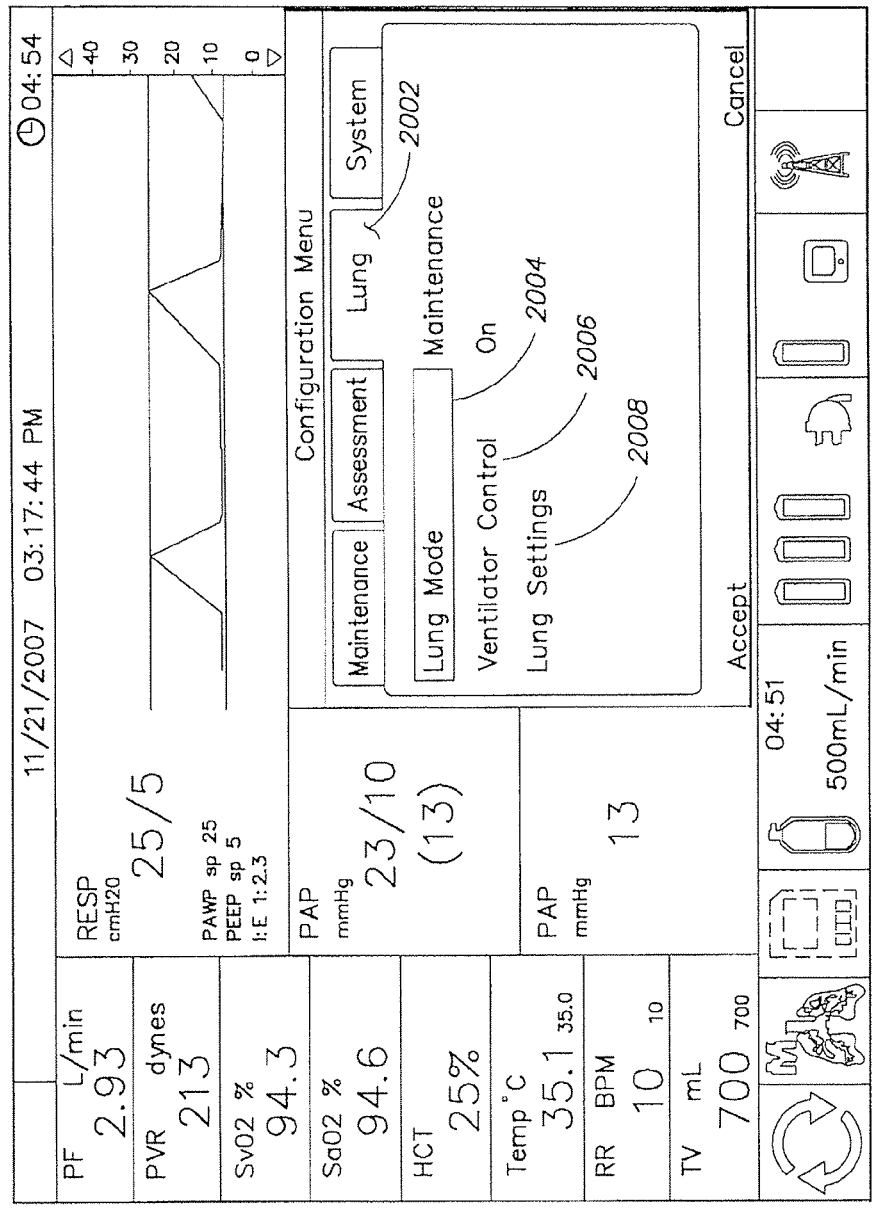
FIG. 20 is a screenshot of the monitor of the organ care system showing the configuration menu for the lung tab, according to the described embodiment.
Figure 21:
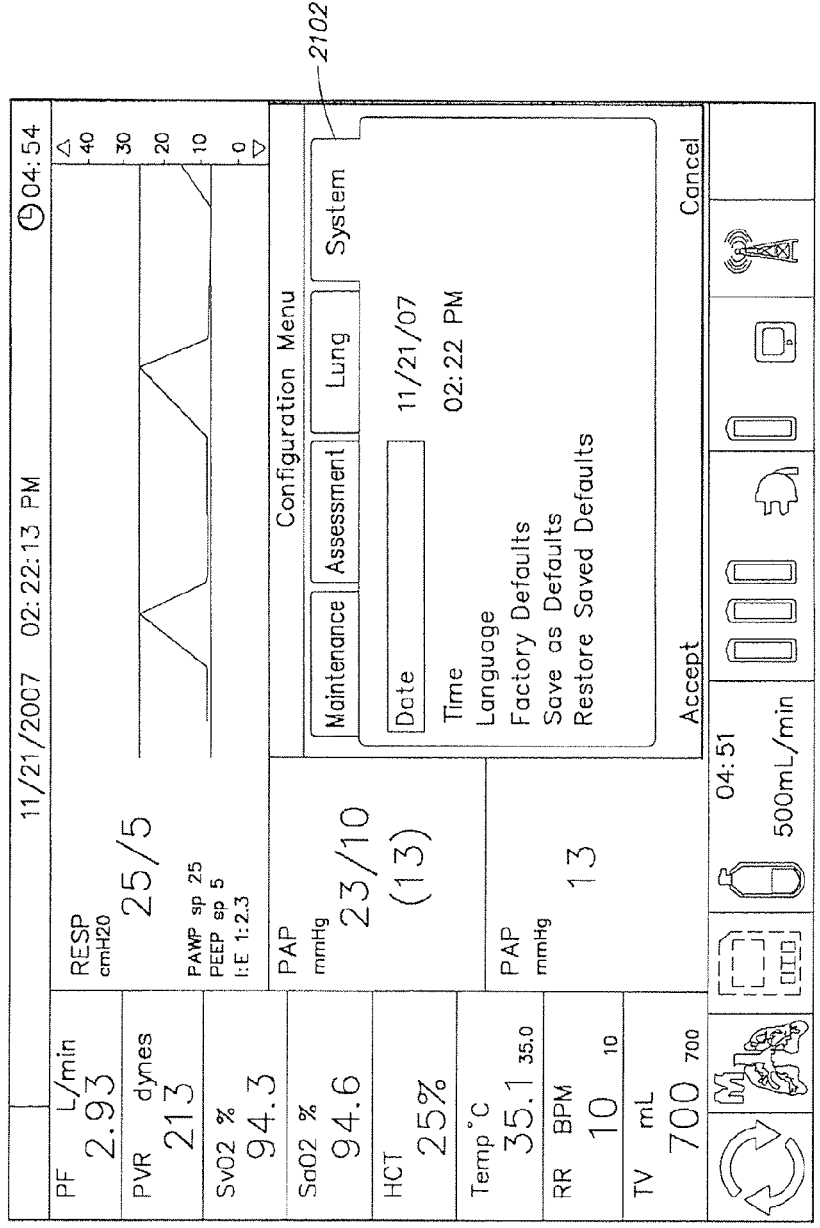
FIG. 21 is a screenshot of the monitor of the organ care system showing the configuration menu for the system tab, according to the described embodiment.

FIG. 20 shows lung tab 2002, which allows the user to set lung mode 2004 to maintenance or assessment, allows ventilator control 2006 to be switched on or off, and provides a link 2008 to lung setting submenu. FIG. 21 shows system tab 2102, which allows the user to set time and date, language, and perform other system actions. Other configuration tabs and associated menus can be added based on the needs of users.

Organ Care System Console Module

Figure 22:
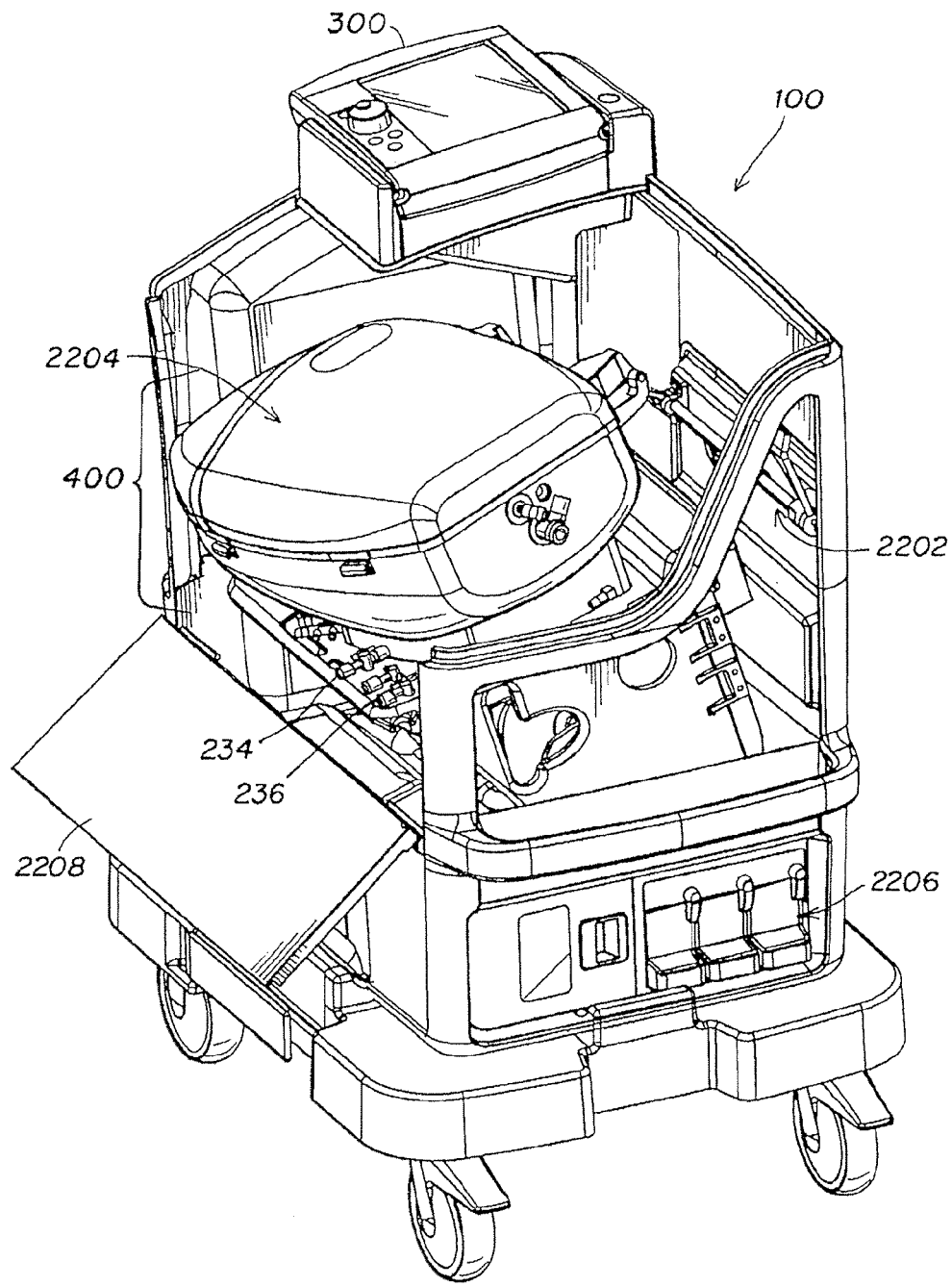
FIG. 22 is an illustration of the organ care system drawn from a 45-degree from the front view, according to the described embodiment.

FIG. 22 is an overall view of OCS console 100 showing the single use, disposable lung perfusion module in a semi-installed position. As broadly indicated in FIG. 22, single use disposable lung perfusion module is sized and shaped to fit into OCS console 100, and to couple with it. Overall, the unit has a similar form to the organ care system described in U.S. patent application Ser. No. 11/788,865. Removable lung perfusion module 400, is insertable into OCS console 100 by means of a pivoting mechanism that allows module 400 to slide into the organ console module from the front, as shown in FIG. 22, and then pivot towards the rear of the unit. Clasp mechanism 2202 secures lung perfusion module 400 in place. In alternative embodiments, other structures and interfaces of lung perfusion module 400 are used to couple the module with OCS 100. When secured in place, electrical and optical connections (not shown) provide power and communication between OCS console 100 and lung perfusion module 400. Details of the electrical and optical connections are described in U.S. patent application Ser. No. 11/246,013, filed on Oct. 7, 2005, the specification of which is incorporated by reference herein in its entirety. A key component of lung perfusion module 400 is organ chamber 2204, which is described in detail below. Battery compartments 2206 and maintenance gas cylinder 220 (not shown) are located in the base of the OCS console 100. OCS console 100 is protected by removable panels, such as front panels 2208. Just below lung perfusion module are perfusate sampling ports 234 and 236. Mounted on top of OCS console 100 is OCS monitor 300.

Figure 23:
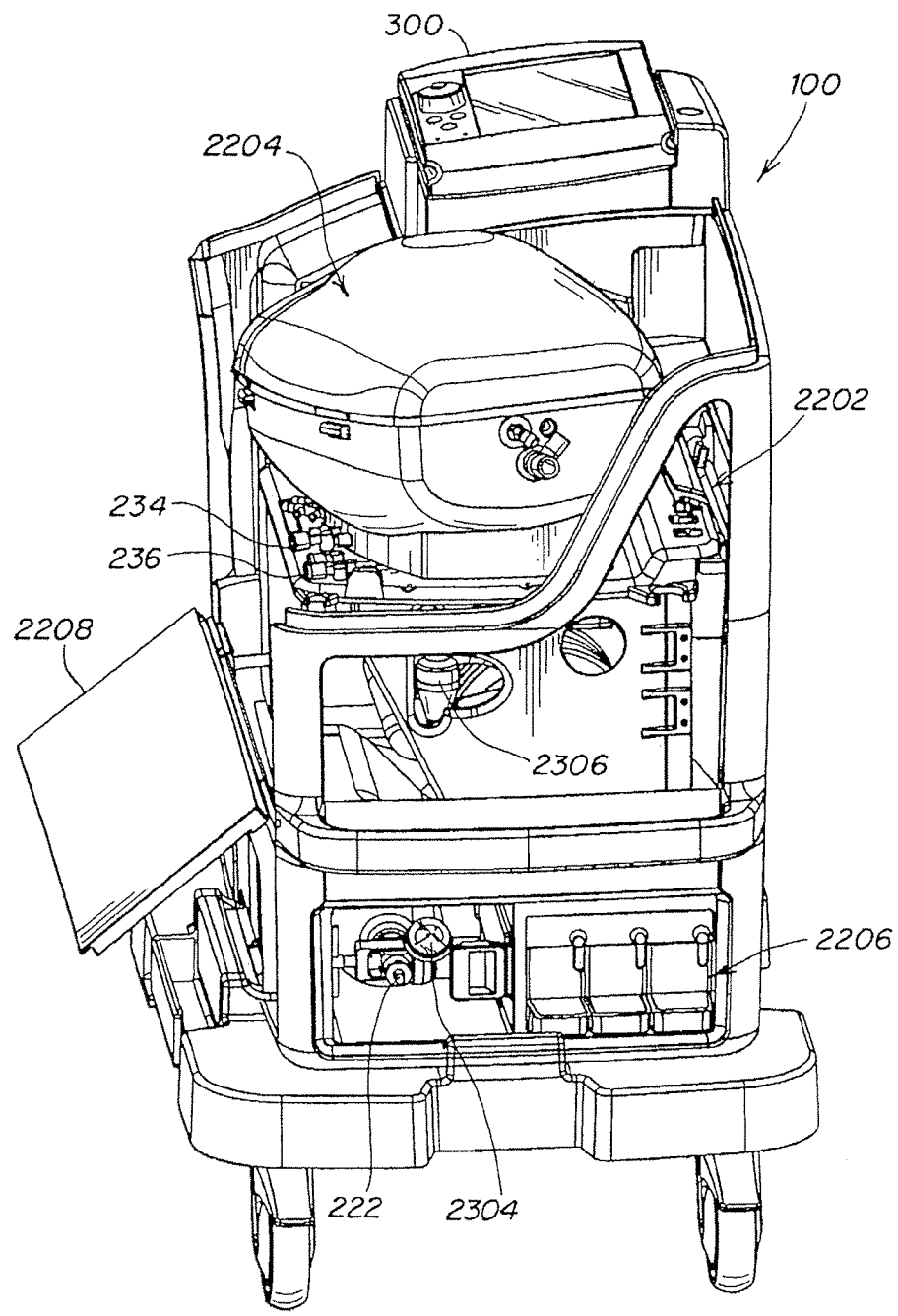
FIG. 23 is a side view illustration of the organ care system, according to the described embodiment.

FIG. 23 is a side view of OCS console 100. LA sampling port 234 and PA sampling port 236 provide means for removing perfusate samples, or for injecting chemicals into perfusion fluid 250. Maintenance gas tank regulator 222 and gauge 2304 are visible in OCS console 100 base. Also visible is one way inflow valve 2306, which is attached to the reservoir and connected to the dome of the perfusate pump.

Figure 24:
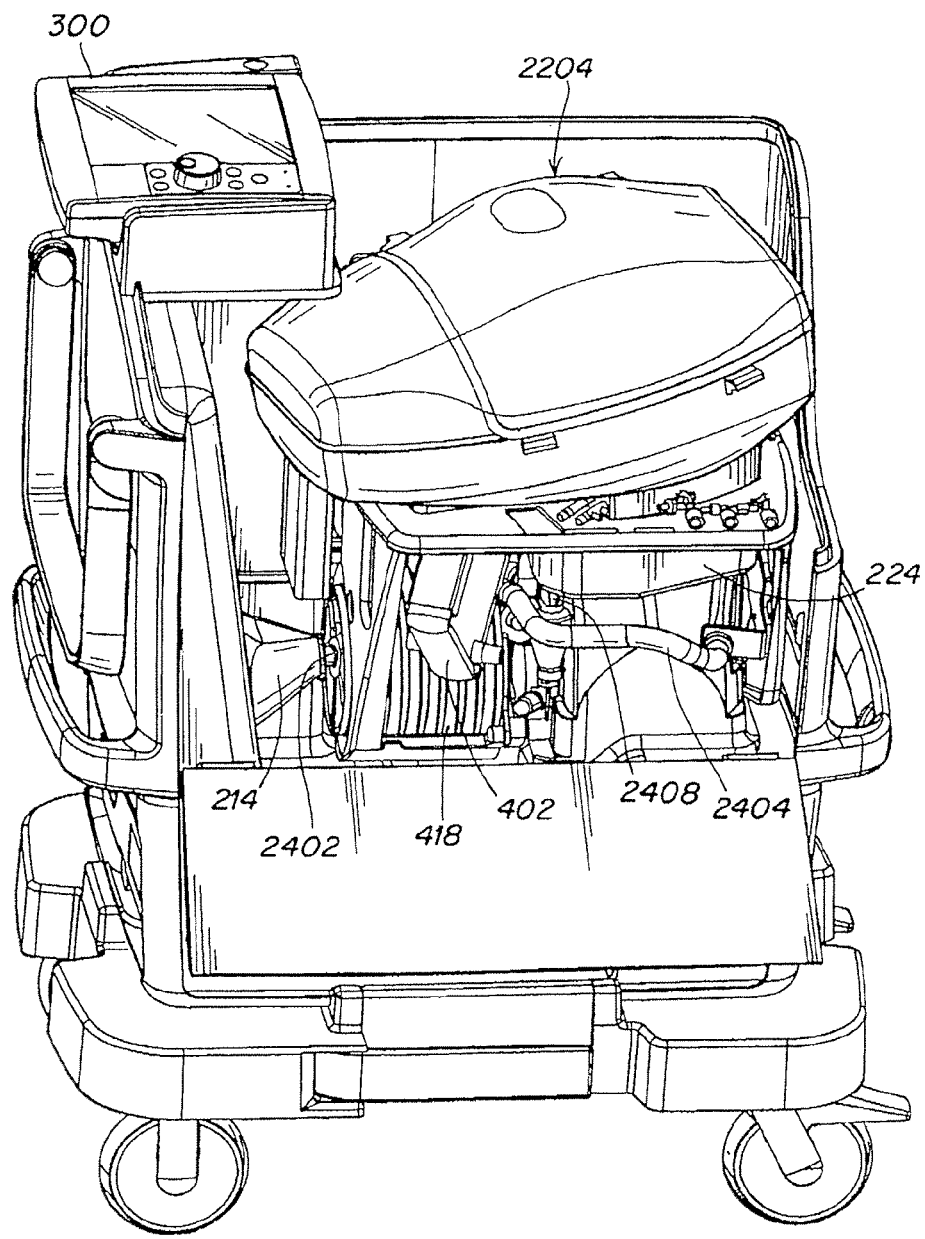
FIG. 24 is a front view illustration of the organ care system, according to the described embodiment.

Additional system components are visible in FIG. 24, which is a front view. Bellows 418 is located just above the OCS console module base, and is driven by mechanical actuator arm 2402 connected to ventilator unit 214 in lung console module 200. Mechanical motion of actuator arm 2402 causes bellows 418 to compress and expand, which drives the gas flow into and out of lungs 404 during a breathing cycle. Gas exchanger 402 is located above bellows 418. In the described embodiment, gas exchanger 402 is a Novalung oxygenator. Perfusate fluid line 2404 connects fluid pump 226 (not shown) and heater 230 (not shown). Just below organ chamber 2204, reservoir 224 collects perfusion fluid, and connects via drain 2408 to pump 226 for recirculation through the system.

Figure 25:
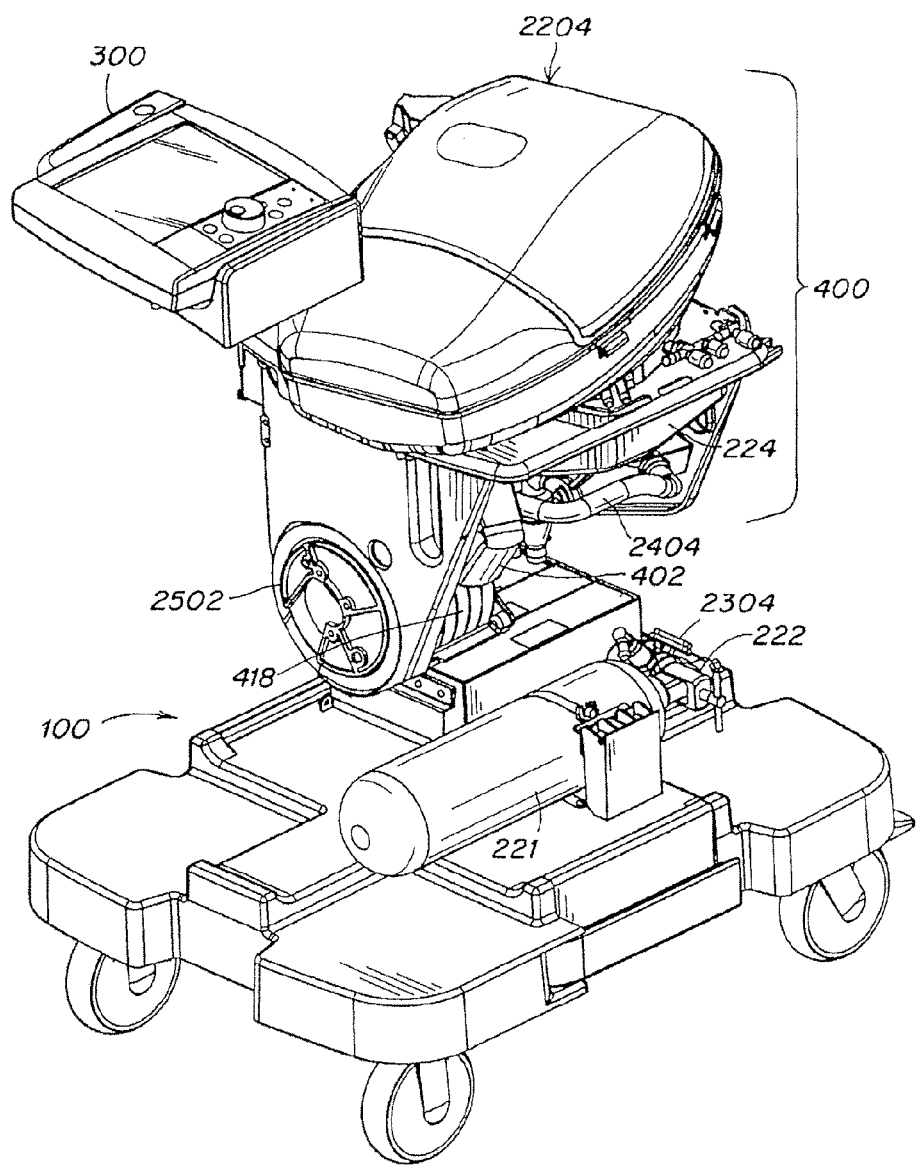
FIG. 25 is an illustration of the organ care system with the side panels removed, according to the described embodiment.

In FIG. 25, the walls of OCS console 100 have been omitted so as to reveal additional internal components of the system. Maintenance gas 220 is stored in a horizontally disposed cylinder, feeding maintenance gas 220 to the system when needed via regulator 222. Lung perfusion module 400 is shown in the installed vertical position. Adjacent to bellows 418 is bellows drive plate 2502, which mates with a flat disk at the end of linear actuator 2402 (not shown).

Figure 26:
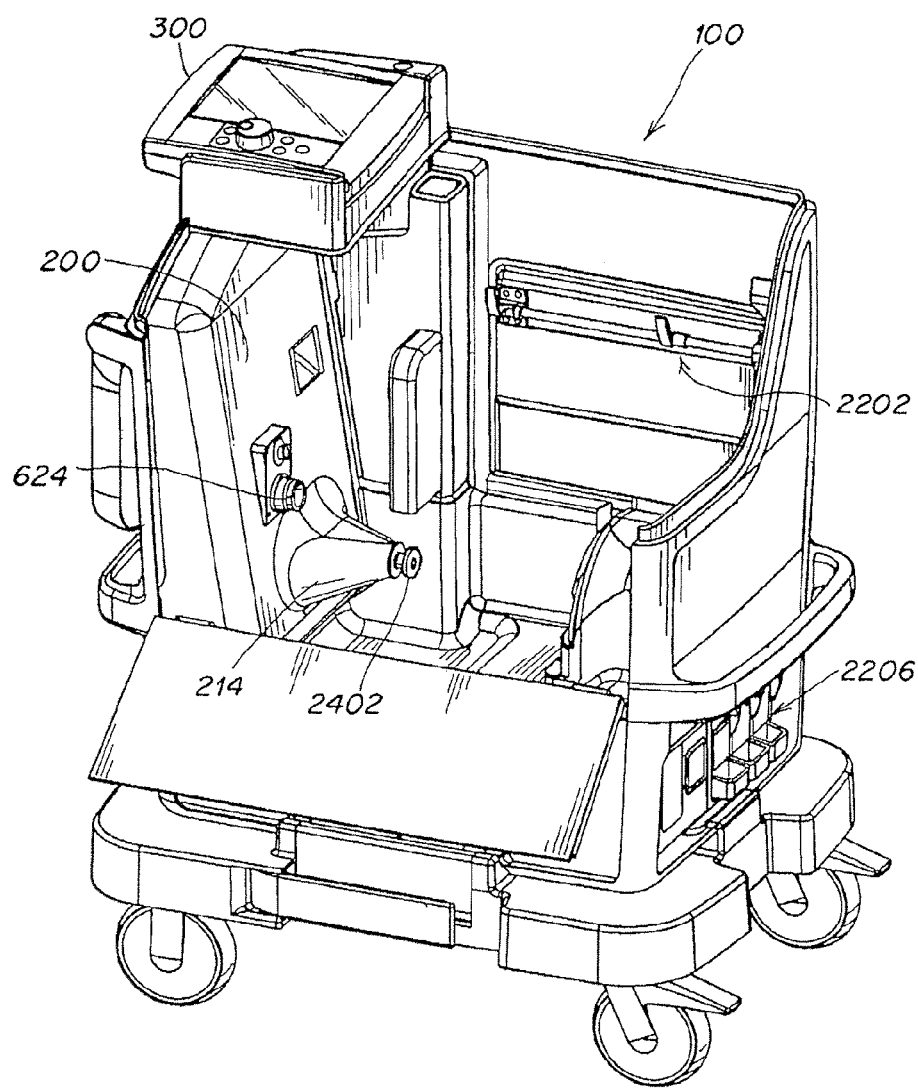
FIG. 26 is an illustration of the organ care system with the lung perfusion module removed, according to the described embodiment.

FIG. 26 is a view of OCS console 100 without disposable lung perfusion module 400. Visible are ventilator module 214 and mechanical actuator arm 2402. Other components (not shown) of lung console module 200 are housed within the module mounted along the left side wall of the OCS console 100. These components are shown in FIG. 1 within lung console module 200, and include console module controller 202, gas exchanger valve 204, airway pressure sensor 206, relief valve actuator 207, pneumatic control module 208, bellows valve actuator 210, trickle valve 212, ventilator 214, gas selector switch 216, and power converter 218. Pneumatic connector 624 provides rapid hook-up to matching lung perfusion module connector 626. This convenient connection provides gas connection to gas exchanger 402 and also to the gas loop between lungs 404 and bellows 418. Connectors 624 and 626 also provide pneumatic control connections between lung console module 200 and lung perfusion module 400 to control bellows valve 414, relief valve 412, and receive pressure data for air sensor 206.

Figure 27:
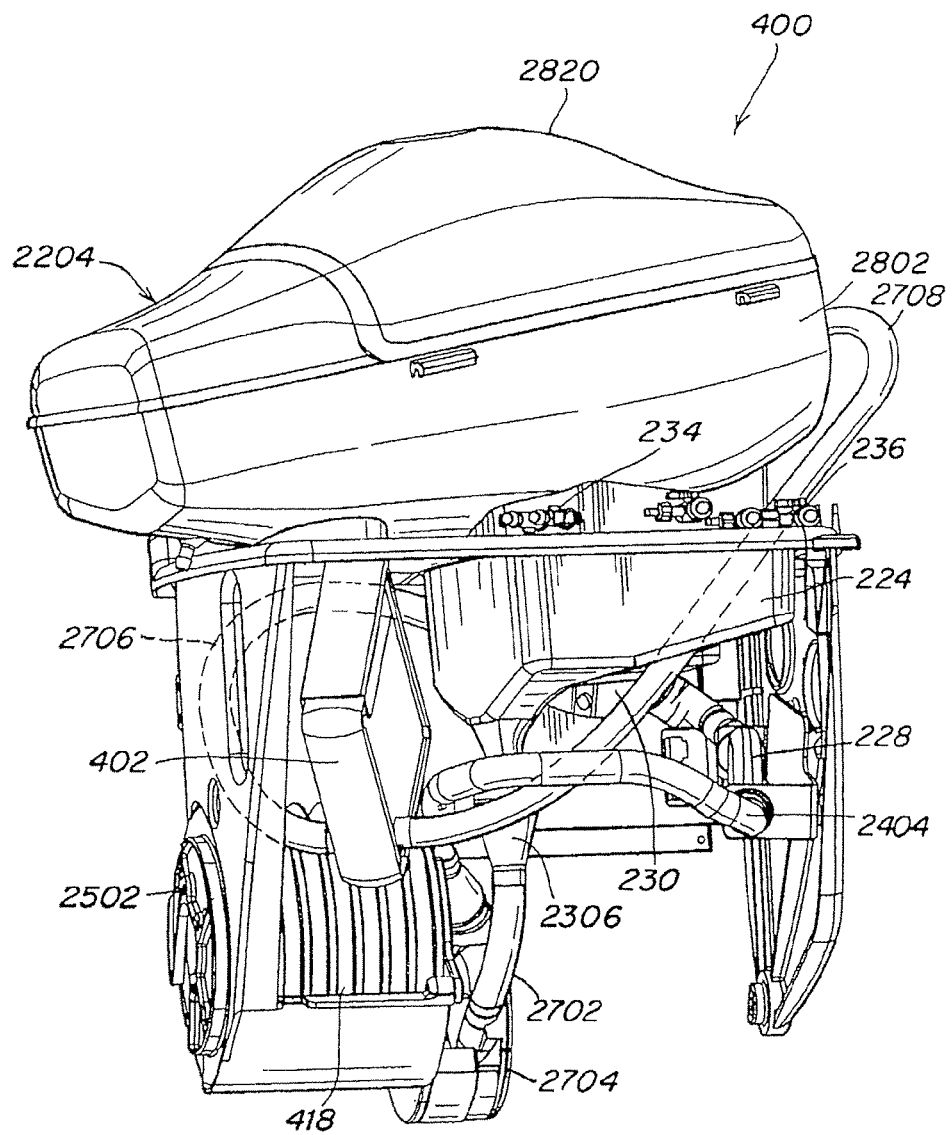
FIG. 27 is an illustration of the lung perfusion module, according to the described embodiment.

FIG. 27 is a front view of lung perfusion module 400. Organ chamber 2204 includes a removable lid 2820 and housing 2802. Sampling ports, including LA sampling port 234 and PA sampling port 236 are visible below organ chamber 2802. Gas exchanger 402, bellows 418, and bellows plate 2502 are also visible in the figure.

We now describe the circulation path of the perfusate, which was first described in connection with FIG. 2, in terms of the components of lung perfusion module 400. Mounted below organ chamber 2204 are perfusate reservoir 224, which stores perfusate 250. The perfusate exits through one-way inflow valve 2306, line 2702, and pump dome 2704 to pump 226 (not shown). The perfusate is pumped through perfusate fluid line 2404 through compliance chamber 228, and then to perfusate heater 230. After passing through heater 230, the perfusate passes through connecting line 2706 to gas exchanger 402. The perfusate exits gas exchanger 402 through connecting line 2708 to the interface with the pulmonary artery. After flowing through the lung and exiting via the pulmonary vein and the left atrium, the perfusate drains through from the base of organ chamber 2204, as described below. These drains feed the perfusate to reservoir 224, where the cycle begins again.

Figure 28:
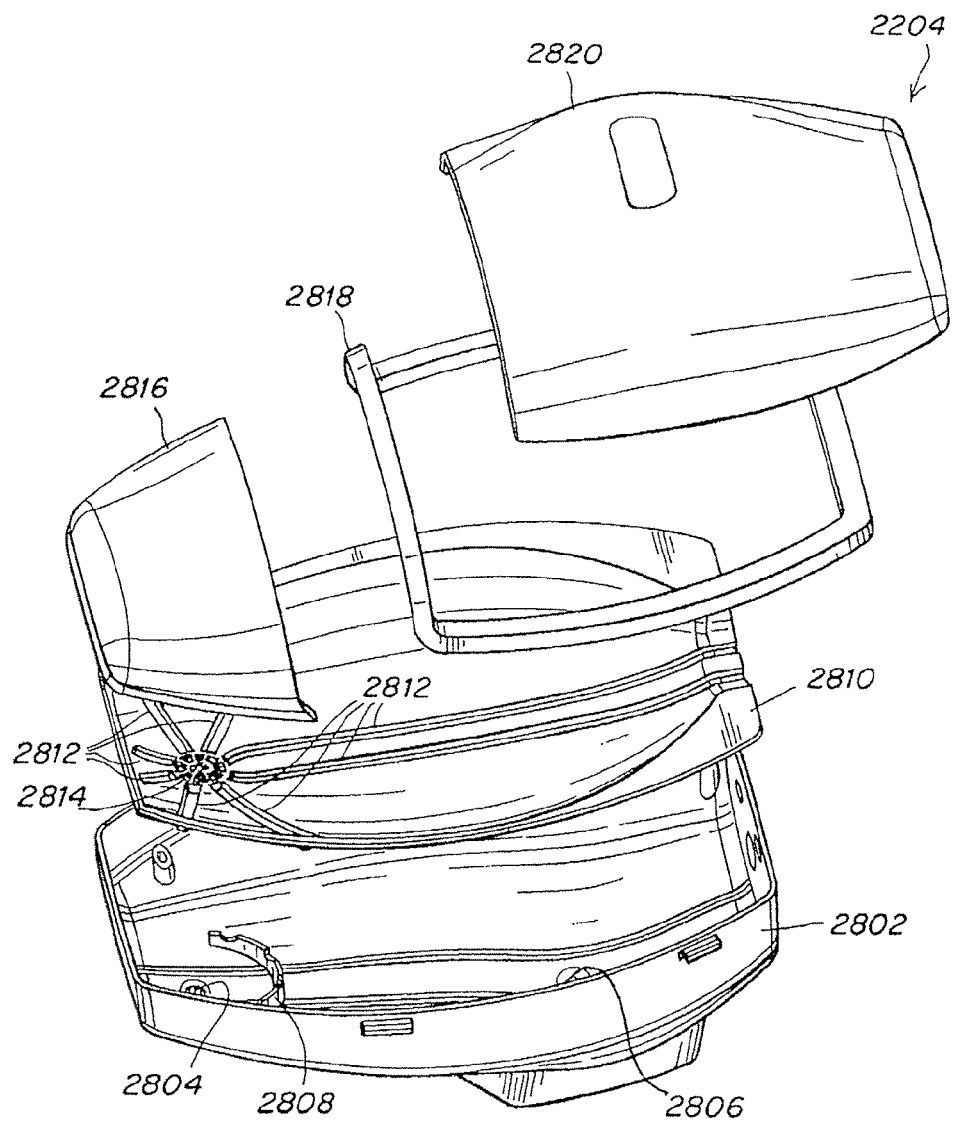
FIG. 28 is an exploded illustration of the lung chamber, according to the described embodiment.

Having described OCS console 100 and lung perfusion module 400, we now describe organ chamber 2204. FIG. 28 shows an exploded view of the components of organ chamber 2204. Base 2802 of chamber 2204 is shaped and positioned within lung perfusion module 400 to facilitate the drainage of the perfusion medium. Organ chamber 2204 has two drains, measurement drain 2804, and main drain 2806, which receives overflow from the measurement drain. Measurement drain 2804 drains perfusate at a rate of about 0.5 l/min, considerably less than perfusion fluid 250 flow rate through lungs 404 of between 1.5 l/min and 4 l/min. Measurement drain leads to oxygen probe 118, which measures $SaO_2$ values, and then leads on to reservoir 224. Main drain 2806 leads directly to reservoir 224 without oxygen measurement. Oxygen probe 118, which is a pulse oxymeter in the described embodiment, cannot obtain an accurate measurement of perfusate oxygen levels unless perfusion fluid 250 is substantially free of air bubbles. In order to achieve a bubble-free column of perfusate, base 2802 is shaped to collect perfusion fluid 250 draining from lungs 404 into a pool that collects above drain 2804. The perfusate pool allows air bubbles to dissipate before the perfusate enters drain 2804. The formation of a pool above drain 2804 is promoted by wall 2808, which partially blocks the flow of perfusate from measurement drain 2804 to main drain 2806 until the perfusate pool is large enough to ensure the dissipation of bubbles from the flow. Main drain 2806 is lower than measurement drain 2804, so once perfusate overflows the depression surrounding drain 2804, it flows around wall 2808, to drain from main drain 2806. In an alternate embodiment of the dual drain system, other systems are used to collect perfusion fluid into a pool that feeds the measurement drain. In some embodiments, the flow from the lungs is directed to a vessel, such as a small cup, which feeds the measurement drain. The cup fills with perfusion fluid, and excess blood overflows the cup and is directed to the main drain and thus to the reservoir pool. In this embodiment, the cup performs a function similar to that of wall 2808 in the embodiment described above by forming a small pool of perfusion fluid from which bubbles can dissipate before the perfusate flows into the measurement drain on its way to the oxygen sensor.

Lungs 404 are supported by support surface 2810. The surface is designed to support lungs 404 without applying undue pressure, while angling lungs 404 slightly downwards towards the lower lobes to promote easy drainage of the perfusate. Support surface includes drainage channels 2812 to collect and channel perfusate issuing from lungs 404, and to guide the perfusate towards drain 2814, which feeds perfusate directly to the blood pool for measurement drain 2804. To provide additional support for the lungs, lungs 404 are wrapped with a polyurethane wrap (not shown) when placed on support surface 2810. The polyurethane wrap anchors lungs 404, helps keep the lungs in a physiologic configuration, and prevents the bronchi from being kinked and limiting the total volume of inflation. The wrap provides a smooth surface for the exterior of the lung to interface with organ chamber 2204, reducing the risk of the chamber applying excessive pressure on any part of lungs 404, which might cause undesirable hemorrhaging. The polyurethane wrap is marked with a series of lines indicating how much volume is being wrapped. The desired volume of wrapped lung can be determined by an empirical relationship between lung size and the weight of the donor. The polyurethane wrap has a series of small holes for draining perfusate that collects around lungs 404. The perfusate is collected by drainage channels 2812 in support surface 2810, which channel the perfusate to drain 2814.

The top of organ chamber 2204 is covered with a sealable lid that includes front piece 2816, top piece 2820, inner lid with sterile drape (not shown), and sealing piece 2818 that seals front piece 2816 to top piece 2820. In an alternate embodiment, the organ chamber includes a double lid system similar to that disclosed in connection with the heart preservation chamber described in U.S. patent application Ser. No. 11/245,957, which is incorporated herein in its entirety. The double lid system includes an outer lid, an intermediate lid, a flexible membrane and sealing frames between the lids and the organ chamber walls. The membrane is preferably transparent, and permits a medical operator to touch/examine the lungs indirectly through the membrane, or apply an ultrasound probe to the lungs through the membrane, while maintaining the sterility of the chamber.

The outer lid opens and closes over the intermediate lid independently of the intermediate lid. Preferably the outer lid is rigid enough to protect lungs 404 from physical contact, indirect or direct. The outer lid and the chamber may be made from any suitable polymer plastic, for example polycarbonate.

Covering the organ chamber serves to minimize the exchange of gases between perfusion fluid 250 and ambient air, and helps ensure that the oxygen probes measure the desired oxygen values, i.e., values corresponding to perfusate exiting the lungs via the LA ($SaO_2$), and entering the lung via the PA ($SvO_2$). The closing of organ chamber 2204 also serves to reduce heat loss from lungs 404. Heat loss can be considerable because of the large surface area of the lungs. Heat loss can be an important issue during transport of the lungs when OCS 1000 may be placed into relatively low temperature environments, such as a vehicle, or the outdoors when moving OCS 1000 into and out of a vehicle. Furthermore, prior to transplantation, OCS 1000 may be temporarily placed in a hospital holding area or in an operating theater, both of which typically have temperatures in the range of 15-22 degrees C. At such ambient temperatures, it is important to reduce heat loss from organ chamber 2204 in order to allow heater 230 to maintain the desired perfusate (and lung) temperature of 35-37 degrees C. Sealing the lungs in the organ chamber 2204 also helps to maintain uniformity of the temperature through lungs 404.

Figure 29:
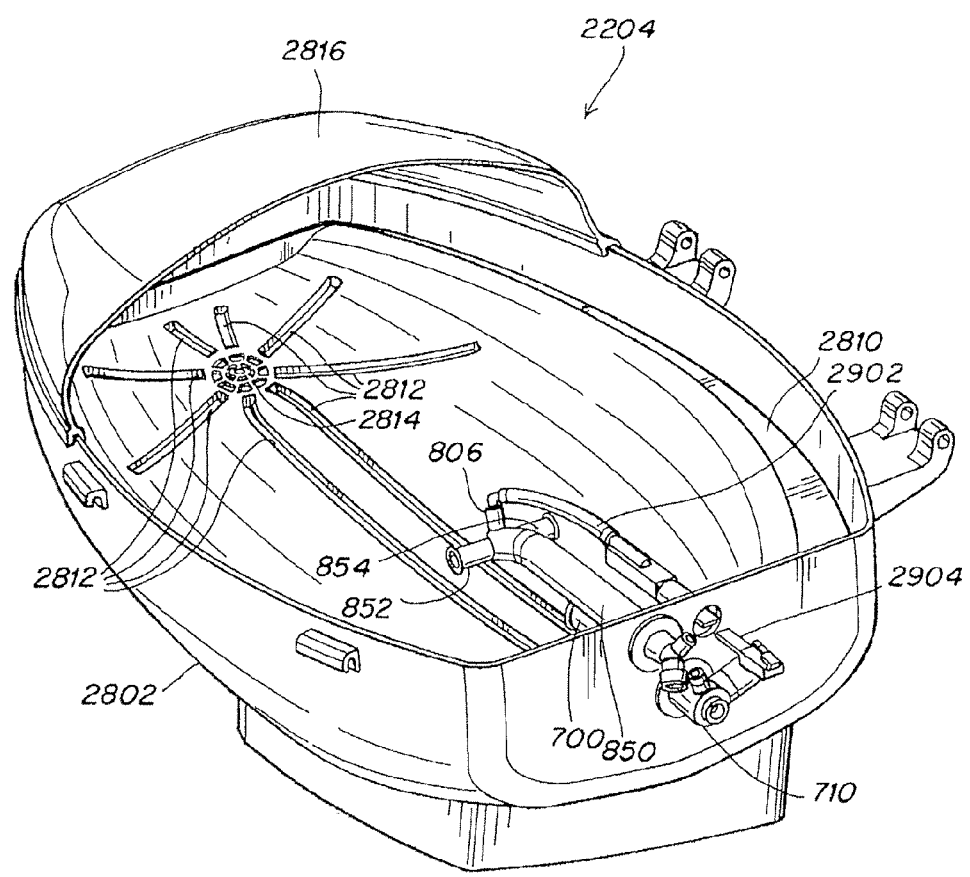
FIG. 29 is an illustration of the lung support surface, housing, and front piece of the lung chamber, according to the described embodiment.
Figure 30:
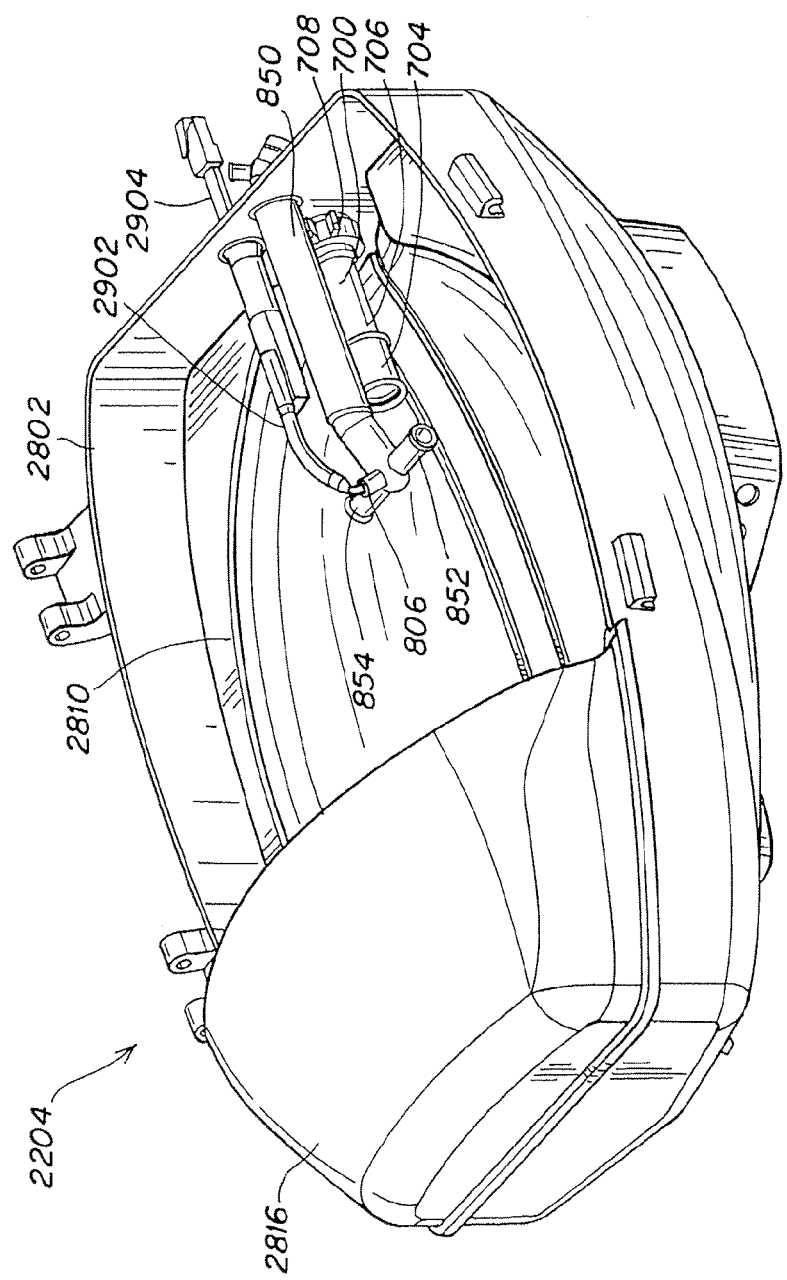
FIG. 30 is an illustration of the lung support surface, housing, and front piece of the lung chamber, showing the tracheal cannula and the PA cannula, according to the described embodiment.

FIG. 29 is a right side view of organ chamber 2204 with the cover removed so as to show support surface 2810. Perfusate drainage channels 2812 and drain 2814 carry perfusate to housing 2802. Also shown are tracheal cannula 700 and tracheal cannula connector 710 for connection to OCS 1000 gas loop. Above tracheal cannula 700 is PA cannula 850 with double connection tubes 852 and 854 at 90 degrees, as illustrated in FIG. 8. Remotely vented pressure sensor 115 (not shown) is connected to the perfusate flow at the point of entry from the PA cannula into lungs 404 by means of connector 806, pressure transducer conduit 2902, and pressure transducer cable 2904. In FIG. 30, which is a left side view of organ chamber 2804, tracheal cannula 700 is clearly displayed. Tracheal cannula 700 is secured to the wall of housing 2802 by means of locknut 708. Adjacent to locknut 708, flexible urethane tubing 706 projects into housing 2802 of organ chamber 2204, leading to silicone-covered connector 704, which connects to the trachea.

Use Models

An exemplary model for using the organ care system described above for lung transplantation is described next with reference to FIGS. 31 and 32.

The process of obtaining and preparing the lungs 404 for cannulation and transport begins by providing a suitable organ donor at step 3100. The organ donor is brought to a donor location, whereupon the process of receiving and preparing the donor lungs 404 for cannulation and transport proceeds down two intersecting pathways. The pathways principally involve preparing OCS 1000 to receive donor lungs 404 and then transporting lungs 404 via OCS 1000 to a recipient site. In particular, pathway 3102 includes exsanguinating the donor, arresting the donor's heart, and preparing lungs 404 for cannulation into OCS 1000. In particular, in the exsanguination step 3104, the donor's blood is removed and set aside so it can be used to perfuse lungs 404 during their maintenance on the OCS 1000. After the donor's blood is exsanguinated, the donor heart is injected in step 3106 with a cardioplegic solution to temporarily halt its beating in preparation for harvesting lungs 404.

After the donor's heart is arrested, a pneumoplegia solution is administered to the lungs at step 3108 before lungs 404 are explanted from the donor at step 3110 and prepared for loading onto OCS 1000 at step 3112.

Figure 31:
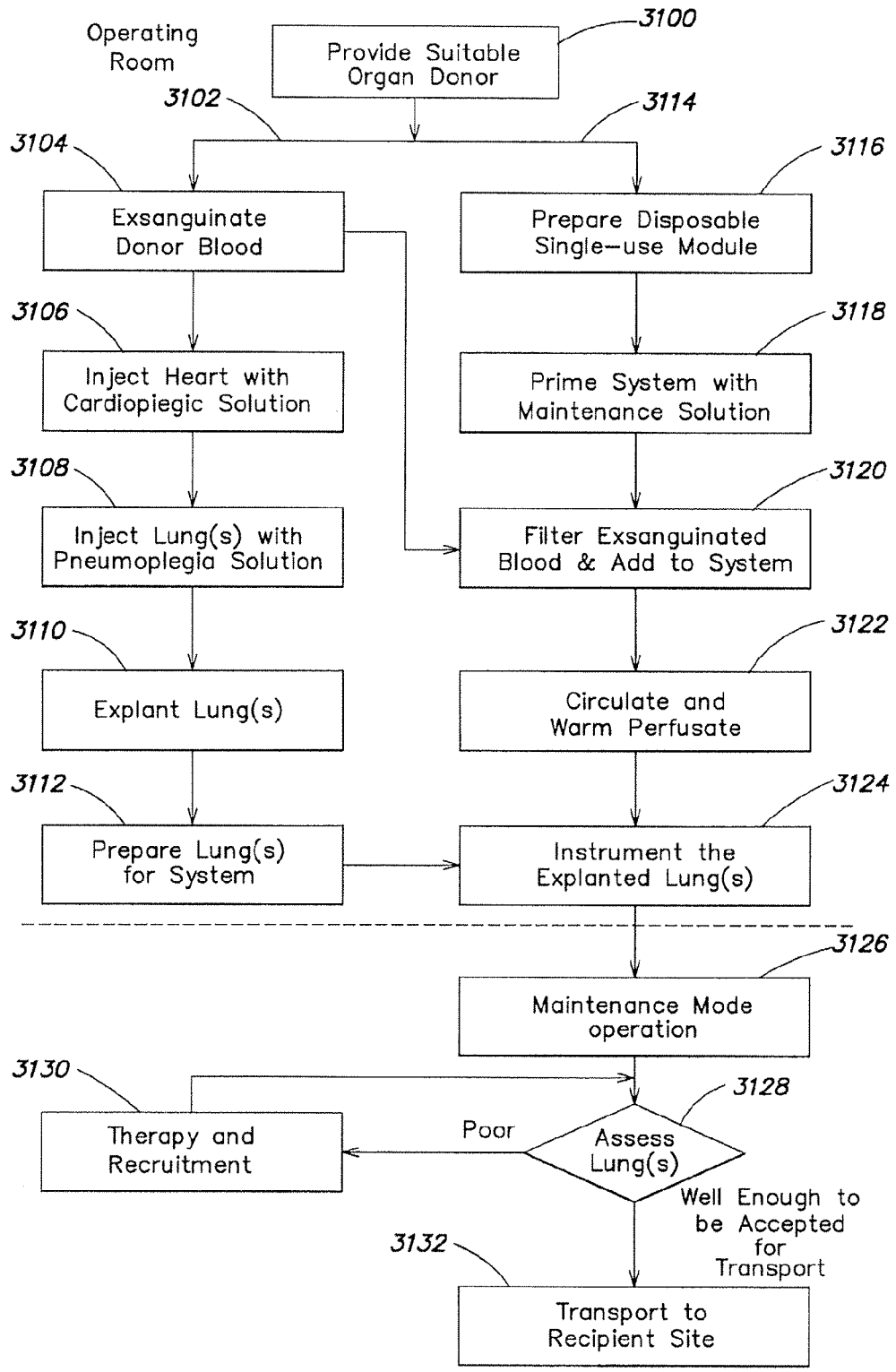
FIG. 31 is a flow diagram showing steps performed at the lung donor site prior to place the lungs into the organ care system, according to the described embodiment.

With continued reference to FIG. 31, after the lungs 404 are explanted from the donor's body, they are instrumented onto OCS 1000 at step 3124 by insertion into the lung chamber 2204 and cannulation at the appropriate perfusion fluid and gas loop interfaces as described above.

According to other illustrative embodiments, the lungs 404 can be transferred directly from the donor to OCS 1000 without the use of cardioplegia. In one particular implementation, the donor's lungs 404 are removed without the donor's heart being arrested and are subsequently instrumented into OCS 1000 for maintenance.

During the preparation of the lungs 1004 via path 3102, OCS 1000 is prepared through the steps of path 3114 so it is primed and waiting to receive lungs 404 for cannulation and transport as soon as the lungs 404 are prepared. In particular, OCS 1000 is prepared in pathway 3114 through a series of steps including providing single use lung perfusion module 400 (step 3116), priming OCS 1000 with a maintenance solution (step 3118), filtering the blood from the donor and adding it to reservoir 224 (step 3120), and circulating and warming the perfusate within OCS 1000 (step 3122). In certain embodiments, perfusion fluid 250 includes whole blood. In certain embodiments, perfusion fluid 250 is partially or completely depleted of leukocytes. In certain embodiments, perfusion fluid 250 is partially or completely depleted of platelets, or includes a blood plasma substitute and is packed with red blood cells. In certain embodiments, perfusion fluid additives include prostaglandin E, Prostacycline, dextran, isuprel, flolan and nitric oxide donors are added while epinephrine is removed. The additives may be generally selected from antimicrobials, vasodilators, and anti-inflammatory drugs. The additives may be delivered to the system 1000 via ports 234, 236 coupled to the reservoir 224, or via an interface in tracheal cannula 700 through a nebulizer or a bronchoscope.

At step 3126, OCS 1000 is selected to operate in maintenance mode. Maintenance mode is described in detail above. After reaching equilibrium in maintenance mode in step 3126, and before being accepted for transport to the donor site, instrumented lungs 404 are assessed in step 3128. The OCS user may select continuous assessment and/or sequential assessment, both of which have been described above.

Based on the results of the assessment conducted in step 3128, and on other monitored parameters of lungs 404, in some instances, it is desirable to provide therapy and recruitment to lungs 404 (step 3130). The pathology that occurs most frequently in donor lungs is collapse, or atelectasis. Use of OCS 1000 provides a number of methods of atelectasis management. First, lungs 404 may be re-inflated using sigh breathing, i.e., by causing lungs 404 to take breaths of varying tidal volume. For example, in one technique, lungs 404 are caused to inhale a first breath having a tidal volume of up to about 1000 ml., followed by two or more smaller breaths having tidal volumes as low as about 100 ml. A second method involves adjusting PEEP levels between values ranging from about 2 cm. $H_2O$ to 15 cm. $H_2O$. In a third method, over-inflated regions of lungs 404 are restrained with the polyurethane wrap that is used to provide support for lungs 404 when placed on support surface 2810. Such restraint allows the judicious application of gas loop pressure to re-inflate collapsed regions of the lungs. In a fourth recruitment approach, the I:E ratio is manipulated, which allows the amount of time spent at pressure plateau 658 (FIG. 6) to be increased, helping lung reinflation, without exceeding peak pressure 656 and PEEP levels 652. Fifth, simple manipulation of lungs 404 on support surface 2810 to change lung position can be an effective recruitment method. Sixth, lung secretions, and alveoli debris in the trachea are removed by suction using a bronchoscope. The bronchoscope is inserted into lungs 404 via a port in a connector between tracheal cannula 700 and gas circuit tubing of lung perfusion module 400. Seventh, surfactant inhalation therapy is performed by injecting surfactants, preferable in aerosol form, into the gas line during the inhalation phase of a breathing cycle.

Another pathology that is often found in donor lungs is localized edema, which can occur in a single or in multiple lobes. Edema can be remedied on OCS 1000 by manipulating PEEP levels, increasing oncotic pressure by ultrafiltration, and manipulation of perfusion fluid pressure by means of vasodilators and/or the flow rate of pump 226.

Pneumonia is also another common pathology of donor lungs, and can be addressed by direct injection of antimicrobial agents into perfusion fluid 250, and/or by inhalation of the agents through the ventilator system of lung perfusion module 400. Another pneumonia recruitment technique is broncho-alveolar lavage.

Bronchospasm, which occurs less frequently than the pathologies discussed above, is managed on OCS 1000 with inhaled broncholdilators. A bronchoscope is optionally used to help inject the bronchodilators into the lungs' airways. Another pathology is high PAP; this is managed by adding vasolidators to perfusion fluid 250.

In some instances, an operator may perform surgery on lungs 404 or provide therapeutic or other treatment, such as immunosuppressive treatments, chemotherapy, genetic testing or irradiation therapy.

In general, lungs 404 are placed in maintenance mode while recruitment is being performed. Assessment step 3128 and recruitment step 3130 may be repeated several times, and may last for a period of up to several hours if needed. The goal is to obtain an assessment of lungs 404 that indicates that the lungs are sufficiently healthy in order to be accepted for transport to the recipient site. Once this condition is satisfied, OCS 1000, with its instrumented lung 404, is loaded into a vehicle for transport to the recipient site.

Figure 32:
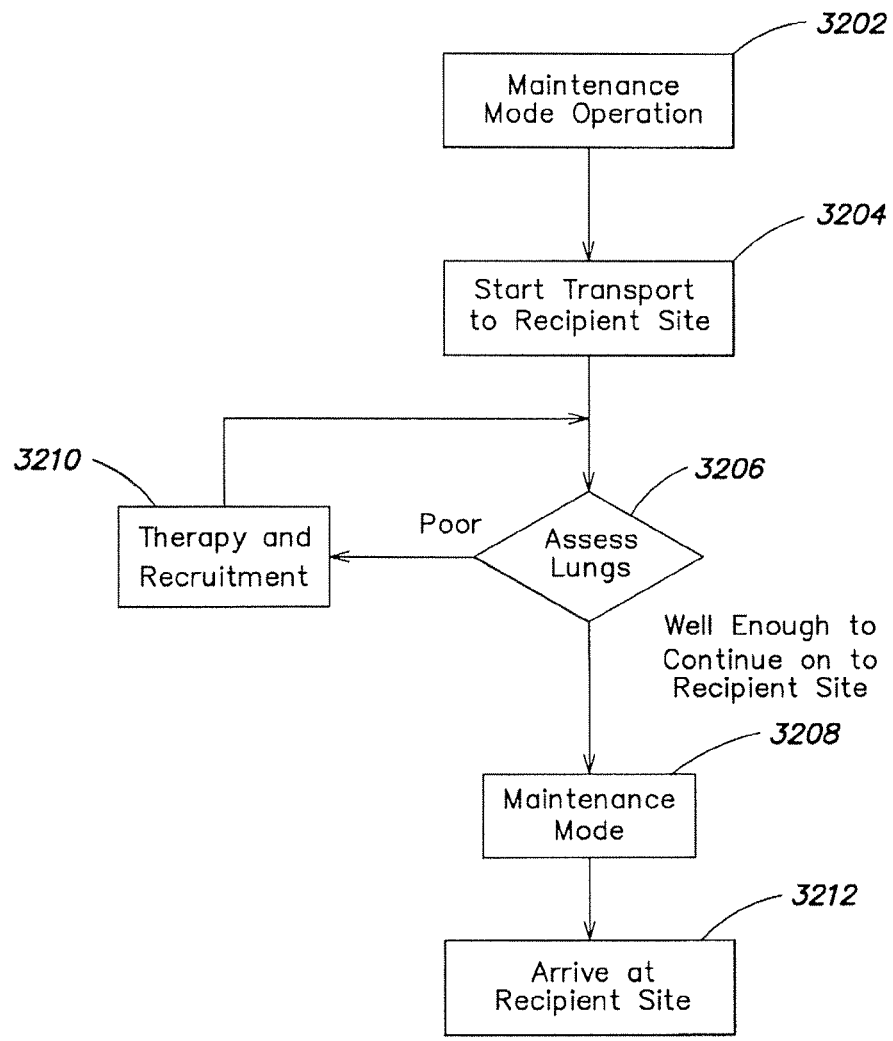
FIG. 32 is a flow diagram showing steps performed during transport of the lungs from the donor site to the recipient site, according to the described embodiment.

FIG. 32 illustrates an exemplary usage mode of OCS 1000 during transport from the donor site to the recipient site. Before being placed in the transport vehicle, OCS 1000 is placed into maintenance mode (step 3202). OCS 1000 is then placed in the vehicle and the journey is commenced (step 3204). After a time interval, the lungs are assessed (step 3206). The time interval before the first assessment depends on the condition of lungs 404 as determined at the donor site, on monitored parameters of lungs 404, and on the anticipated duration of the trip. In general, the poorer the condition of lungs 404, the sooner an assessment will be conducted. If assessment 3206 finds that lungs 404 are in poor condition, therapy and recruitment are performed (step 3210). After a period of recruitment, another assessment (step 3206) is performed. The cycle of assessment and recruitment continues until assessment step 3206 indicates that lungs 404 are above a certain health threshold, and then lungs 404 are returned to maintenance mode 3208. In some embodiments, no further assessment or recruitment takes place during transport. In other embodiments, additional assessment and, if necessary, recruitment steps are performed at intervals during transport. The decision as to whether to conduct further assessments is governed by the operator's overall assessment of the health of lungs 404, as well as by the availability of assessment gas in OCS 1000. Arrival at the recipient site (step 3212) completes the journey.

The choice of which form of assessment to perform is determined by both clinical and technical considerations. From a clinical perspective, perfusion fluid 250 saturation levels are closer to physiologic blood saturation levels in continuous assessment than in sequential assessment. On the other hand, perfusion fluid flow rates are only about one third of the physiologic level in continuous assessment, and are close to physiologic levels in sequential assessment. From a technical perspective, the choice of assessment method may be constrained by the amount of gas available in the OCS. During transport of lungs 404 from the donor site to the recipient site, OCS 1000 functions in a self-contained manner. In particular, it relies on its own internal supplies of maintenance gas and deoxygenation gas. In an illustrative configuration, OCS 1000 has a 200 liter supply of deoxygenation gas 500. In order to perform a single sequential assessment of the lung, approximately 40 liters of deoxygenation gas is required. However, if a lung is in poor health, with a compromised gas exchange capability, more than 40 liters of deoxygenation gas is required for a sequential assessment, since it will take a longer time for the perfusate oxygen levels to fall to the target levels in the deoxygenation phase. Thus, the deoxygenation tank capacity limits the number of sequential assessments in a trip to a maximum of five, and more generally, four or fewer, depending on the condition of lungs 404. On the other hand, performing continuous assessment does not require the achievement of any target deoxygenation level in perfusion fluid 250. Instead, the assessment is run for a fixed time interval, during which deoxygenation gas 500 is flowed through gas exchanger 402 at an average rate of about 10 liters/minute. In an illustrative example, continuous assessment is run for 2 minutes, consuming a total of about 20 liters of deoxygenation gas 500, i.e., about half that consumed in a sequential assessment. Thus, from a technical standpoint, continuous assessment may be preferable to sequential assessment. In a given trip, OCS 1000 has enough gas to permit a maximum of five sequential assessments or ten continuous assessments, or a combination according to the following equation: $40 s+20 c=200$, where s is the number of sequential assessments and c is the number of continuous assessments.

In order to obtain an accurate reading of the perfusate oxygen levels, the perfusate column measured by pulse oxymeters 116 and 118 should be free of gas bubbles. As described above, the dual drain system 2804 and 2806 and the perfusate pool above drain 2804 helps ensure that bubbles do not enter the perfusion line. However, motion of the vehicle transporting OCS 1000 may cause enough agitation to cause some bubbles to drain into the perfusate column. Therefore, in the described embodiment, the vehicle is parked in a level area while assessment is being performed. In other embodiments, lung chamber 2204, lung housing 2802 and the dual drain system are modified to make the system more resistant to motion, such as by confining the blood pool more securely, or by draining perfusate directly into tubes. Such modifications may permit accurate lungs assessments to be performed even while the transporting vehicle is moving.

Figure 33:
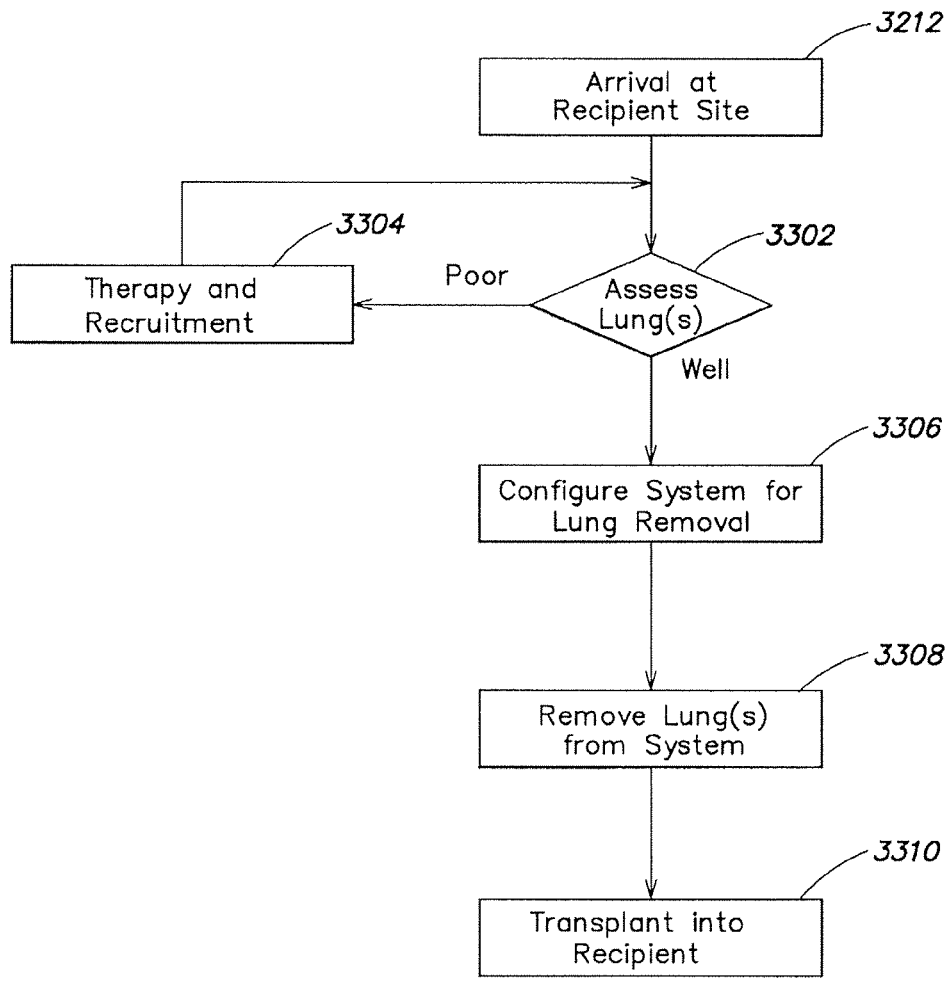
FIG. 33 is a flow diagram showing steps performed at the lung recipient site to remove the lungs from the organ care system and transplant them into the recipient, according to the described embodiment.

FIG. 33 provides an exemplary process for conducting additional tests on the lungs 404 while OCS 1000 is at the recipient site. OCS 1000 performs another assessment (step 3302) of lungs 404. An additional supply of deoxygenation gas may be available at the recipient site, which can supplement the OCS's supply of deoxygenation gas 500 that may have been depleted during transit from the donor site. If the condition of lungs 404 is poor, therapy and recruitment (step 3304) is performed. If, after a final assessment step, lungs 404 are assessed to be in a condition suitable for transplant, lungs 404 are prepared for implantation into the recipient. This includes configuring OCS 1000 for lung removal by pausing the pump 226 to stop the flow of perfusion fluid 250 (step 3306) and, optionally, administering a pneumoplegia solution to lungs 404. Next, in step 3308, lungs 404 are de-cannulated and removed from the lung chamber assembly 2204. In step 3310, lungs 404 are transplanted into the recipient patient by inserting them into the recipient's chest cavity and suturing the various pulmonary connections to their appropriate mating connections within the recipient. In certain embodiments, a portion of the recipient's left atrium may be excised and replaced with one or more of the donor's left atrial cuff to which the donor's pulmonary veins are attached. In other embodiments, only one of two lungs is removed while the remaining lung continues to be perfused and ventilated on the OCS.

It is to be understood that while the invention has been described in conjunction with the various illustrative embodiments, the forgoing description is intended to illustrate and not limit the scope of the invention, which is defined by the scope of the appended claims. For example, a variety of systems and/or methods may be implemented based on the disclosure and still fall within the scope of the invention. Other aspects, advantages, and modifications are within the scope of the following claims. All references cited herein are incorporated by reference in their entirety and made part of this application.

What is claimed is:

1. A lung chamber assembly comprising:
   a housing having a bottom surface defining a first housing drain, and walls,
      wherein the bottom surface defines a pooling region proximate to the first housing drain to collect perfusion fluid draining from a lung, and
      wherein the bottom surface defines an overflow region proximate to the pooling region to collect overflow perfusion fluid from the pooling region;
   a support surface for supporting a lung, the support surface defining a support surface drain for draining a perfusion fluid exiting the lung to the first housing drain;
   a flexible wrap configured to wrap around the lung and maintain the lung in a physiologic configuration, the flexible wrap comprising one or more holes for draining perfusate from the lung to the support surface;
   an openable lid that provides a sealable connection to the walls of the housing;
   a first perfusion interface for allowing a flow of the perfusion fluid into the lung;
   a ventilation interface that allows for ventilation of the lung by a ventilator device; and
   a second perfusion interface for allowing a flow of the perfusion fluid away from the lung.

2. The assembly of claim 1, wherein:
   the bottom surface of the housing defines a second housing drain;
   the first drain is a measurement drain that is in fluid communication with a sensor configured to sense a gas content of the perfusion fluid; and
   the second drain is a main drain that is in fluid communication with a reservoir.

3. The assembly of claim 2, wherein the pooling region is configured to collect perfusion that feeds the measurement drain, the measurement drain having a drainage flow rate less than a flow rate of the perfusion fluid away from the lung.

4. The assembly of claim 3, wherein a flow of perfusion fluid overflowing the pooling region flows toward the overflow region and main drain.

5. The assembly of claim 2, wherein the housing further comprises a wall extending from the bottom surface and partially surrounding the measurement drain, the wall partially blocking a flow of perfusion fluid from the measurement drain to the main drain, the wall promoting formation of a pool of perfusion fluid proximate the measurement drain.

6. The assembly of claim 1, wherein the first perfusion interface includes a pulmonary artery cannula, a proximal portion of the cannula being connected to a perfusion fluid circuit and a distal portion of the cannula being connected to a pulmonary artery of the lung.

7. The assembly of claim 6, wherein a wall of the housing defines an opening for sealably engaging an outer surface of the pulmonary cannula with the housing.

8. The assembly of claim 6, wherein the pulmonary artery cannula further includes a pressure transducer connector, the pressure transducer connector defining an opening into a lumen of the cannula near the distal end of the cannula.

9. The assembly of claim 8, wherein the pressure transducer connector provides a channel for a pressure transducer within the cannula to be remotely vented.

10. The assembly of claim 8, further including a pressure transducer positioned near a point of entry of the perfusion fluid into the pulmonary artery, the pressure transducer being connected to an external controller by a pressure transducer cable, the cable passing through the pressure transducer connector and a pressure transducer conduit.

11. The assembly of claim 10, wherein a wall of the housing defines an opening for sealably engaging an external surface of the pressure transducer conduit.

12. The assembly of claim 1, further comprising a second ventilation interface that includes a tracheal cannula having a distal insertion portion for insertion into a trachea of the lungs, a proximal connector portion for connecting to a gas circuit for ventilating the lung, and a locking mechanism adjacent to the connector portion.

13. The assembly of claim 12, wherein a wall of the housing defines an opening for sealably engaging the tracheal cannula locking mechanism with the housing.

14. The assembly of claim 12, wherein the tracheal insertion portion has a diameter of about 0.65 inches to 0.95 inches.

15. The assembly of claim 12, wherein the insertion portion is bounded at a distal end and a proximal end by a rib, the rib having a diameter about 0.2 greater than a diameter of the insertion portion.

16. The assembly of claim 1, wherein the second perfusion interface includes a left atrial cuff exposed to the lung chamber assembly for allowing the perfusion fluid to flow from the lung to support surface drain.

17. The assembly of claim 1, wherein the second perfusion interface includes a connection between a left atrial cuff and a cannula.

18. The assembly of claim 17, wherein the cannula is in fluid communication with a conduit that directs the perfusion fluid to a perfusion gas content sensor and to a reservoir.

19. The assembly of claim 17, wherein the cannula directs the perfusion fluid to the support surface drain.

20. The assembly of claim 17, wherein the cannula has a cage-like structure for achieving a low contact area between the cannula and the left atrial cuff.

21. The assembly of claim 17, wherein the cannula is configured to hold open the left trial cuff.

22. The assembly of claim 17, wherein the cannula further includes a lumen and a connector for connecting to a pressure transducer positioned inside the cannula.

23. A lung chamber assembly comprising:
a housing having a bottom surface including at least one housing drain, and walls;
a support surface for supporting a lung, the support surface defining a drain for draining a perfusion fluid exiting the lung to the first housing drain;
a flexible wrap configured to wrap around the lung and maintain the lung in a physiologic configuration, the flexible wrap comprising one or more holes for draining perfusate from the lung to the support surface;
an openable lid that provides a sealable connection to the walls of the housing;
a first perfusion interface for allowing a flow of the perfusion fluid into the lung;
a ventilation interface that allows ventilation of the lung by a ventilator; and
a second perfusion interface for allowing a flow of the perfusion fluid away from the lung;
wherein the first perfusion interface includes at least one connector portion, and at least one insertion tube attached to a distal end of the connector portion and disposed at an angle relative to the connection portion, and wherein the insertion tube is made of a bio inert material having a hardness between about 50 Shore A and 90 Shore A for suturing the insertion tube to a pulmonary artery.

* * * * *